US011618787B2

United States Patent
Ahmadi et al.

(10) Patent No.: US 11,618,787 B2
(45) Date of Patent: Apr. 4, 2023

(54) METHODS OF TREATING HIGH RISK MULTIPLE MYELOMA

(71) Applicant: Janssen Biotech, Inc., Horsham, PA (US)

(72) Inventors: Tahamtan Ahmadi, Rydal, PA (US); Christopher Chiu, Warren, NJ (US); Ming Qi, Phoenixville, PA (US); Amy Sasser, Doylestown, PA (US); Jordan Schecter, Livingston, NJ (US)

(73) Assignee: JANSSEN BIOTECH, INC., Horsham, PA (US)

( * ) Notice: Subject to any disclaimer, the term of this patent is extended or adjusted under 35 U.S.C. 154(b) by 0 days.

(21) Appl. No.: 16/177,239

(22) Filed: Oct. 31, 2018

(65) Prior Publication Data

US 2019/0127479 A1    May 2, 2019

Related U.S. Application Data

(60) Provisional application No. 62/579,234, filed on Oct. 31, 2017.

(51) Int. Cl.
| | |
|---|---|
| *C07K 16/28* | (2006.01) |
| *A61K 39/395* | (2006.01) |
| *A61P 35/00* | (2006.01) |
| *A61K 31/573* | (2006.01) |
| *A61K 31/495* | (2006.01) |
| *A61K 31/4439* | (2006.01) |
| *A61K 31/69* | (2006.01) |
| *A61K 9/00* | (2006.01) |
| *A61K 31/454* | (2006.01) |
| *A61K 39/00* | (2006.01) |

(52) U.S. Cl.
CPC ........ *C07K 16/2896* (2013.01); *A61K 9/0019* (2013.01); *A61K 31/4439* (2013.01); *A61K 31/454* (2013.01); *A61K 31/573* (2013.01); *A61K 31/69* (2013.01); *A61K 39/3955* (2013.01); *A61P 35/00* (2018.01); *A61K 31/495* (2013.01); *A61K 2039/54* (2013.01); *A61K 2039/545* (2013.01); *C07K 2317/34* (2013.01); *C07K 2317/56* (2013.01); *C07K 2317/565* (2013.01)

(58) Field of Classification Search
CPC ............ C07K 16/2896; C07K 2317/56; C07K 2317/565; A61K 2039/545
See application file for complete search history.

(56) References Cited

U.S. PATENT DOCUMENTS

| | | |
|---|---|---|
| 6,737,056 B1 | 5/2004 | Presta |
| 7,183,387 B1 | 2/2007 | Presta |
| 7,223,397 B1 | 5/2007 | Rosenblum et al. |
| 7,829,673 B2 | 11/2010 | DeWeers |
| 7,829,693 B2 | 11/2010 | Kreutzer et al. |
| 8,008,449 B2 | 8/2011 | Korman et al. |
| 8,088,896 B2 | 1/2012 | Tesar et al. |
| 8,153,765 B2 | 4/2012 | Park et al. |
| 8,318,154 B2 | 11/2012 | Frost et al. |
| 8,354,509 B2 | 1/2013 | Carven et al. |
| 8,431,380 B2 | 4/2013 | Bookbinder et al. |
| 9,040,050 B2 * | 5/2015 | Van De Winkel ...... A61P 35/00 424/141.1 |
| 9,603,927 B2 | 3/2017 | Doshi |
| 9,732,154 B2 | 8/2017 | Doshi |
| 10,385,135 B2 | 8/2019 | Janssen et al. |
| 10,556,961 B2 | 2/2020 | Doshi |
| 10,604,580 B2 | 3/2020 | Lokhorst |
| 10,668,149 B2 | 6/2020 | Doshi et al. |
| 10,766,965 B2 | 9/2020 | Chaulagain |
| 10,781,261 B2 | 9/2020 | Janssen et al. |
| 10,793,630 B2 | 10/2020 | Doshi et al. |
| 10,800,851 B2 | 10/2020 | Doshi |
| 11,021,543 B2 | 6/2021 | Ahmadi et al. |
| 11,566,079 B2 | 1/2023 | Jansson et al. |
| 2004/0141982 A1 | 7/2004 | Lust et al. |
| 2004/0268425 A1 | 12/2004 | Bookbinder et al. |
| 2006/0257397 A1 | 11/2006 | Throsby |
| 2007/0148178 A1 | 6/2007 | Fyfe et al. |
| 2008/0063642 A1 | 3/2008 | Adelman et al. |
| 2008/0166344 A1 | 7/2008 | Nakahara et al. |
| 2009/0076249 A1 | 3/2009 | Deweers et al. |
| 2009/0148449 A1 | 6/2009 | DeWeers |
| 2009/0304687 A1 | 12/2009 | Drachman |
| 2009/0304710 A1 | 12/2009 | Park et al. |
| 2010/0068136 A1 | 3/2010 | Hansen |

(Continued)

FOREIGN PATENT DOCUMENTS

| | | |
|---|---|---|
| AU | 2013203186 A1 | 5/2013 |
| CL | 2013001944 A1 | 9/2014 |

(Continued)

OTHER PUBLICATIONS

Berglund et al., Protein Science, 2008, 17:606-613.*

(Continued)

*Primary Examiner* — Hong Sang
(74) *Attorney, Agent, or Firm* — Hamilton, Brook, Smith & Reynolds, P.C.

(57) ABSTRACT

Disclosed are methods of treating a subject having high-risk multiple myeloma, methods of achieving negative minimal residual disease status in a subject having multiple myeloma, and methods of predicting a likelihood of, or decreasing a risk of, relapse and/or disease progression in a subject having multiple myeloma.

12 Claims, 25 Drawing Sheets

Specification includes a Sequence Listing.

(56) References Cited

U.S. PATENT DOCUMENTS

| | | |
|---|---|---|
| 2010/0074885 A1 | 3/2010 | Schiff et al. |
| 2010/0092489 A1 | 4/2010 | van de Winkel et al. |
| 2010/0285004 A1 | 11/2010 | Tesar et al. |
| 2011/0044997 A1 | 2/2011 | Adler et al. |
| 2011/0053247 A1 | 3/2011 | Baker |
| 2011/0066111 A1 | 3/2011 | Teschner et al. |
| 2011/0076273 A1 | 3/2011 | Adler et al. |
| 2011/0099647 A1 | 4/2011 | De Weers et al. |
| 2011/0293606 A1 | 12/2011 | Lejeune |
| 2011/0300157 A1 | 12/2011 | Devy et al. |
| 2012/0171153 A1 | 7/2012 | Frost et al. |
| 2012/0201827 A1 | 8/2012 | Elias |
| 2012/0219551 A1 | 8/2012 | Johnson et al. |
| 2012/0231008 A1 | 9/2012 | Guo et al. |
| 2012/0244110 A1 | 9/2012 | Chen et al. |
| 2012/0258081 A1 | 10/2012 | Corringham et al. |
| 2012/0259095 A1 | 10/2012 | Beliard et al. |
| 2012/0295864 A1 | 11/2012 | Taube et al. |
| 2013/0022588 A1 | 1/2013 | Yang et al. |
| 2013/0109593 A1 | 5/2013 | Hartmann et al. |
| 2013/0137134 A1 | 5/2013 | Mordechai et al. |
| 2013/0209355 A1 | 8/2013 | De Weers et al. |
| 2013/0302400 A1 | 11/2013 | Maneval et al. |
| 2013/0309250 A1 | 11/2013 | Cogswell et al. |
| 2013/0323247 A1 | 12/2013 | Zugmaier et al. |
| 2014/0051662 A1* | 2/2014 | Moussy ............... A61K 31/10 514/64 |
| 2014/0099254 A1 | 4/2014 | Chang et al. |
| 2014/0155584 A1 | 6/2014 | Elias et al. |
| 2014/0248238 A1 | 9/2014 | Wilson et al. |
| 2014/0271644 A1 | 9/2014 | Elias et al. |
| 2014/0309183 A1 | 10/2014 | Kerr |
| 2014/0314800 A1 | 10/2014 | Mathieu et al. |
| 2014/0356318 A1 | 12/2014 | Barken |
| 2015/0118251 A1 | 4/2015 | Deslandes |
| 2015/0125447 A1 | 5/2015 | Heider |
| 2015/0231235 A1* | 8/2015 | Van De Winkel ..... A61K 31/69 424/139.1 |
| 2015/0246123 A1 | 9/2015 | Doshi |
| 2015/0246975 A1 | 9/2015 | Doshi |
| 2015/0376276 A1 | 12/2015 | Lewis et al. |
| 2016/0009683 A1 | 1/2016 | Hansen et al. |
| 2016/0067205 A1 | 3/2016 | Lokhorst |
| 2016/0222106 A1 | 8/2016 | Doshi et al. |
| 2016/0367663 A1 | 12/2016 | Doshi et al. |
| 2016/0376373 A1 | 12/2016 | Ahmadi |
| 2017/0008966 A1 | 1/2017 | Chaulagain |
| 2017/0044265 A1 | 2/2017 | Ahmadi |
| 2017/0107295 A1 | 4/2017 | Lokhorst |
| 2017/0121414 A1 | 5/2017 | Jansson et al. |
| 2017/0121417 A1 | 5/2017 | Jansson et al. |
| 2017/0174780 A1 | 6/2017 | Doshi |
| 2017/0320961 A1 | 11/2017 | Doshi |
| 2018/0117150 A1* | 5/2018 | O'Dwyer ............... A61K 38/47 |
| 2019/0144557 A1 | 5/2019 | Ahmadi et al. |
| 2019/0233533 A1 | 8/2019 | Otten |
| 2019/0330363 A1 | 10/2019 | Janssen et al. |
| 2020/0002433 A1 | 1/2020 | Janssen et al. |
| 2020/0121588 A1 | 4/2020 | Campbell et al. |
| 2020/0223936 A1 | 7/2020 | Doshi et al. |
| 2020/0231697 A1 | 7/2020 | Jansson et al. |
| 2020/0268847 A1 | 8/2020 | Qi |
| 2020/0308284 A1 | 10/2020 | Bandekar et al. |
| 2020/0308296 A1 | 10/2020 | Bandekar et al. |
| 2020/0316197 A1 | 10/2020 | Bandekar et al. |
| 2020/0330593 A1 | 10/2020 | Bandekar et al. |
| 2020/0339701 A1 | 10/2020 | Jansson et al. |
| 2020/0392242 A1 | 12/2020 | Liu et al. |
| 2020/0397896 A1 | 12/2020 | Liu |
| 2020/0405854 A1 | 12/2020 | Liu et al. |
| 2020/0407459 A1 | 12/2020 | Chaulagain et al. |
| 2021/0047401 A1 | 2/2021 | Doshi et al. |
| 2021/0061920 A1 | 3/2021 | Doshi et al. |
| 2021/0095042 A1 | 4/2021 | Jansson et al. |
| 2021/0107991 A1 | 4/2021 | Jansson et al. |
| 2021/0403592 A1 | 12/2021 | Ahmadi et al. |
| 2022/0041745 A1 | 2/2022 | Bandekar et al. |
| 2022/0062415 A1 | 3/2022 | Xie et al. |
| 2022/0204638 A1 | 6/2022 | Liu et al. |
| 2022/0275090 A1 | 9/2022 | Alvarez Arias |

FOREIGN PATENT DOCUMENTS

| | | |
|---|---|---|
| CL | 2016002158 A1 | 7/2017 |
| EA | 009383 B1 | 12/2007 |
| EA | 015584 B1 | 10/2011 |
| EA | 201390993 | 12/2013 |
| EP | 2561868 A1 | 2/2013 |
| EP | 2567976 A2 | 3/2013 |
| EP | 2 459 167 B1 | 5/2013 |
| EP | 2 477 603 | 3/2016 |
| JP | 2002-534396 A | 10/2002 |
| JP | 2008-533977 A | 8/2008 |
| JP | 2009-511033 A | 3/2009 |
| JP | 2010-506582 A | 3/2010 |
| JP | 2014-509837 A | 4/2014 |
| NZ | 576122 | 9/2012 |
| WO | WO 89/08114 A1 | 9/1989 |
| WO | WO 92/01049 A2 | 1/1992 |
| WO | WO 94/17184 A1 | 8/1994 |
| WO | WO 96/16990 A1 | 6/1996 |
| WO | WO 98/16245 A1 | 4/1998 |
| WO | WO 98/16254 A1 | 4/1998 |
| WO | WO 98/50435 A1 | 11/1998 |
| WO | WO 99/62526 A2 | 12/1999 |
| WO | WO 00/06194 A2 | 2/2000 |
| WO | WO 00/40265 A1 | 7/2000 |
| WO | WO 2001/060803 A1 | 8/2001 |
| WO | WO 01/97844 A1 | 12/2001 |
| WO | WO 02/06347 A1 | 1/2002 |
| WO | WO 02/32288 A2 | 4/2002 |
| WO | WO 2003/106498 A2 | 12/2003 |
| WO | WO 2004/058288 A1 | 7/2004 |
| WO | WO 2004/078140 A2 | 9/2004 |
| WO | WO 2004/092160 A1 | 10/2004 |
| WO | WO 2005/042019 A1 | 5/2005 |
| WO | WO 2005/044855 A2 | 5/2005 |
| WO | WO 2005/063819 A2 | 7/2005 |
| WO | WO 2005/103083 A2 | 11/2005 |
| WO | WO 2006/088951 A2 | 8/2006 |
| WO | WO 2006/099875 A1 | 9/2006 |
| WO | WO 2006/125640 A2 | 11/2006 |
| WO | WO 2007/042309 A2 | 4/2007 |
| WO | WO 2008/037257 A2 | 4/2008 |
| WO | WO 2008/047242 A2 | 4/2008 |
| WO | WO 2008/073160 A2 | 6/2008 |
| WO | WO 2008/116103 A2 | 9/2008 |
| WO | WO 2008/121615 A2 | 10/2008 |
| WO | WO 2008/150530 A2 | 12/2008 |
| WO | WO 2009/062054 A1 | 5/2009 |
| WO | WO 2009/118142 A1 | 10/2009 |
| WO | WO 2009/128917 | 10/2009 |
| WO | WO 2010/052014 | 5/2010 |
| WO | WO 2010/061357 A1 | 6/2010 |
| WO | WO 2010/061358 A1 | 6/2010 |
| WO | WO 2010/061359 A1 | 6/2010 |
| WO | WO 2010/061360 A1 | 6/2010 |
| WO | WO 2011/012637 A2 | 2/2011 |
| WO | WO 2011/029892 A2 | 3/2011 |
| WO | WO 2011/109365 A2 | 9/2011 |
| WO | WO 2011/154453 A1 | 12/2011 |
| WO | WO 2012/041800 A1 | 4/2012 |
| WO | WO 2012/076663 A1 | 6/2012 |
| WO | WO 2012/092612 A1 | 7/2012 |
| WO | WO 2012/092616 A1 | 7/2012 |
| WO | WO 2013/059885 A2 | 5/2013 |
| WO | WO 2013/102144 A2 | 7/2013 |
| WO | WO 2013/164837 A1 | 11/2013 |
| WO | WO 2014/048921 A1 | 4/2014 |
| WO | WO 2014/068114 A1 | 5/2014 |
| WO | WO 2014/089416 A1 | 6/2014 |
| WO | WO 2014/142220 A1 | 9/2014 |
| WO | WO 2014/178820 A1 | 11/2014 |
| WO | WO 2015/009726 A2 | 1/2015 |

(56) References Cited

FOREIGN PATENT DOCUMENTS

| | | |
|---|---|---|
| WO | WO 2015/066450 A1 | 7/2015 |
| WO | WO 2015/121454 A1 | 8/2015 |
| WO | WO 2015/130728 A1 | 9/2015 |
| WO | WO 2015/130732 A2 | 9/2015 |
| WO | WO 2015/195555 A1 | 12/2015 |
| WO | WO 2015/195556 A1 | 12/2015 |
| WO | WO 2016/040294 A2 | 3/2016 |
| WO | WO 2016/089960 A1 | 6/2016 |
| WO | WO 2016/133903 A2 | 8/2016 |
| WO | WO 2016/187546 A1 | 11/2016 |
| WO | WO 2016/209921 A1 | 12/2016 |
| WO | WO 2016/210223 A1 | 12/2016 |
| WO | WO 2017/004266 A1 | 1/2017 |
| WO | WO 2017/079150 A1 | 5/2017 |
| WO | WO 2018/002181 A1 | 1/2018 |
| WO | WO 2019/089832 A1 | 5/2019 |
| WO | WO 2019/186273 A1 | 10/2019 |

OTHER PUBLICATIONS

Palumbo et al., N. Engl. J. Med., Aug. 25, 2016, 375: 754-766.*
Supplementary material of Palumbo et al., N. Engl. J. Med., Aug. 25, 2016, 375: 754-766, the protocol, total pp. 119.*
Sagaster et al., Leukemia, 2007, 21:164-168.*
"A Prospective Phase II of Daratumumab in Previously Treated Systemic Light Chain (AL) Amyloidosis", published online at (http://cms.cws.net/content/beta.myelomasociety.org/files/2017ash/Roussel,%20Murielle-ASH2017.pdf (2017).
Aarhust, et al., "ADP-ribosyl Cyclase and CD38 Catalyze the Synthesis of a Calcium mobilizing Metabolite from NADP+," The Journal of Biological Chemistry, 270(51): 30327-30333 (1995).
Adriouch et al., "Extracellular NAD+: a danger signal hindering regulatory T cells," Microbes and Infection, 14:1284-1292 (2012).
Agheli, A. et al., "A Rare Case of Primary Amyloidosis, Presenting with Severe Pulmonary Hypertension and Bilateral Pleural Effusion," Blood, vol. 106: p. 5100 (2005).
Arican, et al., "Philadelphia Chromosome (+) T-Cell Acute Lymphoblastic Leukemia After Renal Transplantation," Transplantation Proceedings, vol. 31; 3242-3243 (1999).
Armitage et al., "Long-Term Remission Durability and Functional Status of Patients Treated for Diffuse Histiocytic Lymphoma with the CHOP Regimen," J. Clin. Oncol. 2:898-902, (1984).
Arthur, "Innovations in subcutaneous infusions," J. Infus. Nurs. 38(3); 179-87; May/Jun. 2015.
Bachireddy, et al., "Haematologic Malignancies: at the Forefront of Immunotherapeutic Innovation," Nature Reviews Cancer, vol. 15, No. 4, pp. 201-215, Apr. 1, 2015 (Apr. 1, 2015).
Bahlis, N.J. et al., "Daratumumab, lenalidomide, and dexamethasone (DRd) vs lenalidomide and dexamethasone (Rd) in relapsed or refractory multiple myeloma (RRMM): Efficacy and safety updated (POLLUX)," Journal of Clinical Oncology, vol. 35; No. 15; 8025; Abstract (2017).
Blankestijn, et al., "Could daratumumab be used to treat severe allergy?," Journal of Allergy and Clinical Immunology, Elsevier, Amsterdam, NL, vol. 139, No. 5, p. 1677-1678, Jan. 19, 2017.
Brand, F-X. et al., "Prospect for Anti-HER2 Receptor Therapy in Breast Cancer," AntiCancer Research, vol. 26; 463-470 (2006).
Brown, et al., "Tolerance of single, but not multiple, amino acid replacements in antibody VH CDR 2: a means of minimizing B cell wastage from somatic hypermutation?" The Journal of Immunology, 156: 3285-3291 (1996).
Carter et al., "Identification and validation of cell surface antigens for antibody targeting in oncology," Endocrine-Related Cancer, vol. 11, pp. 659-687, (2004).
Chari et al., "Subcutaneous Delivery of Daratumumab in Patients with Relapsed or Refractory Multiple Myeloma (RRMM): PAVO, an Open-label, Multicenter, Dose Escalation Phase lb Study," American Society of Hematology, Clinical Trials.gov Identifier NCTO2519452, Dec. 2017.
Chari A. et al., "Subcutaneous delivery of daratumumab in patients (pts) with relapsed or refractory multiple myeloma (RRMM): PAVO, an openlabel, multicenter, dose escalation phase lb study," 2017 ASH Annual Meeting ANZMAP Multiple Myeloma Highlights, 2017.
Chaulagain, C.P., et al., "How we Treat Systemic Light-Chain Amyloidosis," Clinical Advances in Hematology & Oncology, vol. 13; No. 5; 315-324 (2015).
Chen, et al., "Selection and Analysis of an Optimized Anti-VEGF Antibody: Crystal Structure of an Affinity-matured Fab in Complex with Antigen," Journal of Molecular Biology, 293: 865-881 (1999).
Cheson et al., "Revised Response Criteria for Malignant Lymphoma," Journal of Clinical Oncology, vol. 25, No. 5, 579-586 (Feb. 10, 2007).
Chillemi, A. et al., "Anti-CD38 Antibody Therapy: Windows of Opportunity Yielded by the Functional Characteristics of the Target Molecule," Molecular Medicine, vol. 19; 99-108 (2013).
Chou, et al., "Drug Combination Studies and their Synergy Quantification Using the Chou-Talalay Method," Cancer Research, 70(2): 440-446 (2010).
ClinicalTrials.gov "Study of YM155 in Refractory Diffuse Large B-cell Lymphoma (DLBCL) Subjects," Interventional Studies, U.S. National Library of Medicine, https://clinicaltrials.gov/ct2/show/record/NCT00498914, First posted Jul. 11, 2007 [retrieved on Sep. 10, 2018].
Colman, "Effects of amino acid sequence changes on antibody-antigen interactions," A Structural View of Immune Recognition by Antibodies, Biomolecular Research Institute, 33-36, (1994).
Cotner, et al., "Human T Cell Proteins Recognized by Rabbit Heteroantisera and Monoclonal Antibodies," International Journal of Immunopharmaceuticals, 3(3): 255-268 (1981).
Davies, et al., "Affinity improvement of single antibody VH domains: residues in all three hypervariable regions affect antigen binding," Immunotechnology, 2: 169-179 (1996).
Davis, et al., "Transgenic mice as a source of fully human antibodies for the treatment of cancer," Cancer and Metastasis Reviews, 18: 421-425 (1999).
Deckert, et al., "SAR650984, A Novel Humanized CD38-Targeting Antibody, Demonstrates Potent Antitumor Activity in Models of Multiple Myeloma and Other CD38β Hematologic Malignancies," Clinical Cancer Research. vol. 20, No. 17, pp. 4574-4583 (2014).
Dennis, "Off by a Whisker," Nature, 442 (17): 749-741 (2006).
DePascalis, et al., "Grafting of 'Abbreviated' Complementarity-Determining Regions Containing Specificity-Determining Residues Essential for Ligand Contact to Engineer a Less Immunogenic Humanized Monoclonal Antibody," The Journal of Immunology, 169: 3076-3084 (2002).
De Weers, et al., "Daratumumab, a Novel Therapeutic Human CD38 Monoclonal Antibody, Induces Killing of Multiple Myeloma and Other Hematological Tumors," The Journal of Immunology, 186: 1840-1848 (Pre-published online Dec. 27, 2010).
De Weers, M. et al., "Humax-CD38, a New Human CD38 Monoclonal Antibody, Effectively Mediates Killing of Multiple Myeloma and Plasma Cell Leukemia Cells," abstract, Submitted for the 16th European Congress of Immunology—ECI2006, Paris, France, [Sep. 6-9, 2006].
De Weers et al., "HuMax-CD38, a new human CD38 monoclonal antibody, effectively mediates killing of multiple myeloma and plasma cell leukemia cells," The 23rd International Conference on Advances in the Application of Monoclonal Antibodies in Clinical Oncology, (Jun. 26-28, 2006), Royal Myconian Resort & Thalasso Spa Center, Mykonos, Greece (Abstract).
Dimopoulos, M.A. et al., "Daratumumab, Lenalidomide, and Dexamethasone for Multiple Myeloma," The New England Journal of Medicine, vol. 375; No. 14; 1319-1331 (2016).
Dimopoulos, M.A. et al., "Daratumumab plus lenalidomide and dexamethasone versus lenalidomide and dexamethasone in relapsed or refractory multiple myeloma: updated analysis of POLLUX," Haematologica, vol. 103; No. 12; 2088-2096 (2018).
Dos Santos, et al., Anti-Leukemic Activity of Daratumumab in Acute Myeloid Leukemia Cells and Patient-Derived Xenografts, Blood, vol. 124, Abstract 2312, (2014).

(56) References Cited

OTHER PUBLICATIONS

Doshi, et al., "Daratumumab Treatment in Combination with Chop or R-Chop Results in the Inhibition or Regression of Tumors in Preclinical Models of Non-Hodgkins Lymphoma," Haematologica, The Hematology Journal, 99(1): 138 (2014).
Ellis, et al., "Engineered Anti-CD38 Monoclonal Antibodies for Immunotherapy of Multiple Myeloma," The Journal of Immunology, 155: 925-937 (1995).
Eldfors, et al., "Landscape of Mutations in Relapsed Acute Myeloid Leukemia," vol. 124: No. 21, p. 2367; (2014).
Engert, et al., "A Phase-I Study of an Anti-CD25 Ricin A-Chain Immunotoxin (RFT5-SMPT-dgA) in Patients with Refractory Hodgkin's Lymphoma," Blood, 89(2): 403-410 (1997).
Ferrero, et al., Characterization and phylogenetic epitope mapping of CD38 ADPR cyclase in the cynomolgus macaque, BMC Immunology, 5(21): 1-13 (2004).
Field-Smith, "Bortezomid (Velcade™) in the treatment of multiple myeloma," Therapeutic and Clinical Risk Management, 2(3): 271-279 (2006).
Flavell, et al., "Therapy of human T-cell acute lymphoblastic leukaemia with a combination of anti-CD7 and anti-CD38-SAPORIN immunotoxins is significantly better than therapy with each individual immunotoxin," Br. J. Cancer, vol. 84, No. 4, pp. 571-578, (2001).
Franco, et al., "The transmembrane glycoprotein CD38 is a catalytically active transporter responsible for generation and influx of the second messenger cyclic ADP-ribose across membranes," FASEB Journal, 12: 1507-1520 (1998).
Fujimori, et al., "A Modeling Analysis of Monoclonal Antibody Percolation Though Tumors: A Binding-Site Barrier," Journal of Nucleic Medicine, 31: 1191-1198 (1990).
Funaro et al., "CD38 Functions Are Regulated Through an Internalization Step," Journal of Immunology, 160: 2238-2247 (1998).
Funaro, et al., "Human CD38: a versatile leukocyte molecule with emerging clinical prospectives," Fundamental and Clinical Immunology, 3(3): 101-113 (1995).
Funaro, et al., "Identification and characterization of an active soluble form of human CD38 in normal and pathological fluids," International Immunology, 8(11): 1643-1650 (1996).
Funaro, et al., "Involvement of the Multilineage CD38 Molecule in a Unique Pathway of Cell Activation and Proliferation," The Journal of Immunology, 145: 2390-2396 (1990).
Gallo, et al., "The human immunoglobulin loci introduced into mice: V(D) and J gene segment usage similar to that of adult humans," European Journal of Immunology, 30: 534-540 (2000).
Genmab "Humanx-CD38 Effective in Preclinical Studies," Genmab A/S, Stock Exchange Release 57/2005.
Genmab "Daratumumab Receives Breakthrough Therapy Designation from US Food and Drug Administration", Copenhagen, Denmark; May 1, 2013—Genmab A/S (OMX: GEN) disponible en: http://files.shareholder.com/downloads/AMDA-KPIBN/0x0x659093/64b187b8-830c-4252-acd6-8019b4199069/18%20Daratumumab%20breakthrough%20status_010513_uk.pdf, (May 1, 2013).
Genmab Announces Daratumumab and Ofatumumab Data to Be Presented at American Society of Hematology Annual Meeting (ASH), American Society of Hematology Annual Meeting and Exposition, San Francisco, California, Media Release 06; pp. 1-3 (Nov. 2014).
George, et al., "Differential Effects of Anti-β2-Glycoprotein I Antibodies on Endothelial Cells and on the Manifestations of Experimental Antiphospholipid Syndrome," Circulation, 97: 900-906 (1998).
Goldmacher, et al., "Anti-CD38-Blocked Ricin: An immunotoxin for the Treatment of Multiple Myeloma," The American Society of Hematology, 84(9): 3017-3025 (1994).
Goodwin, "Subcutaneous Daratumumab Potential Game Changer for Multiple Myeloma," Oncology Times, 2017 American Society of Hematology Annual Meeting, p. 49, (2017).
Gopalakrishnan, et al. "Daratumumab improves the anti-myeloma effect of newly emerging multidrug therapies," Blood and Lymphatic Cancer: Targets and Therapy, 3: 19-24 (2013).
Graeff, et al., "Enzymatic Synthesis and Characterizations of Cyclic GDp-ribose," The Journal of Biological Chemistry, 269(48): 30260-30267 (1994).
Green, "Antibody engineering via genetic engineering of the mouse: XenoMouse strains are a vehicle for the facile generation of therapeutic human monoclonal antibodies," Journal of Immunological Methods, 231: 11-23 (1999).
Green, et al., "Antigen-specific human monoclonal antibodies from mice engineered with hyman Ig heavy and light chain YACs," Nature Genetics, 7: 13-21 (1994).
Guse et al., "Regulation of calcium signaling in T lymphocytes by the second messenger cyclic ADP-ribose," Nature 398:70-73, (1999).
Haart, et al., "Sepantronium bromide (YM155) improves daratumumab-mediated cellular lysis of multiple myeloma cells by abrogation of bone marrow stromal cell-induced resistance," Haematologica, Letters to the Editor, vol. 101, No. 8, pp. e339-e343, (2016).
Hara-Yokoyama, "Alteration of enzymatic properties of cell-surface antigen CD38 by agonistic anti-CD38 antibodies that prolong B cell survival and induce activation," International Immunopharmacology, 8: 59-70 (2008).
Hartmann, Radioimmunotherapy of Nude Mice Bearing a Human Interleukin 2 Receptor α-expressing Lymphoma Utilizing the α-emitting Radionuclide-eonjugated Monoclonal Antibody 212Bi-anti-Tac, Cancer Research, 54: 4362-4370 (1994).
Henry, et al., "the use of basiliximab in solid organ transplantation," Expert Opinion Pharmacotherapy, 3(10): 1657-1663 (2002).
Holm, et al., "Functional mapping and single chain construction of the anti-cytokeratin 8 monoclonal antibody TSI," Molecular Immunology, 44: 1075-1084 (2017).
Hoshino, et al., "Mapping of the Catalytic and Epitopic Sites of Human CD38/NAD+ Glycohydrolase to a Functional Domain in the Carboxyl TerminusI," The Journal of Immunology, 158: 741-747 (1997).
Howard, et al., "Formation and Hydrolysis of Cyclic ADP-Ribose Catalyzed by lymphocyte Antigen CD38," Science, 262(5136): 1056-1059 (1993).
Hu, Y., et al., "Immunophenotypic analysis of abnormal plasma cell clones in bone marrow of primary systemic light chain amyloidosis patients," Chin Med J., vol. 127; No. 15; 2765-2770; Abstract only (2014).
Hu, Y. et al., "The Significance of Abnormal Plasma Cell Clone in Bone Marrow of Primary Systemic Light Chain Amyloidosis Patients," Blood, vol. 122; p. 5342 (2013).
Ikehata, et al., "Autoantibodies against CD38 (ADP-ribosyl Cyclase/Cyclic ADP-ribose Hydrolase) that Impair Glucose-induced Insulin Secretion in Noninsulin-dependent Diabetes Patients," Journal of Clinical Investigations, 102(2): 395-401 (1998).
Jackisch, et al., "Subcutaneous versus intravenous formulation of trastuzumab for HER2-positive early breast cancer: updated results from the phase III HannaH study," Annals of Oncology, vol. 26, pp. 320-325, (2015).
Jackson, et al., "Isolation of a cDNA Encoding the Human CD38 (T10) molecule, A Cell Surface Glycoprotein With an Unusual Discontinuous Pattern of Expression During Lymphocyte Differentiation," The Journal of Immunology, 144(7): 2811-2815 (1990).
Jagannath, et al. Treatment (tx) journeys in newly diagnosed multiple myeloma (NDMM) patients (pts): Results from the Connect MM Registry. Multiple Myeloma Update from the American Society of Clinical Oncology. (ASCO) 41st Annual meeting, (Jun. 4, 2018).
Jakob, et al., "Stage-dependent Expression of CD7, CD45RO, CD45RA and CD25 on CD4-positive Peripheral Blood T-lymphocytes in Cutaneous T-cell Lymphoma," Acta Derm Venerology, 76: 34-36 (1996).
Jakobovits, "the long-awaited magic bullets: therapeutic human monoclonal antibodies from transgenic mice", Expert Opinion on Investigational Drugs, 7(4): 607-614 (1998).
Jang, et al., "The structural basis for DNA binding by an anti-DNA autoantibody," Molecular Immunology, 35: 1207-1217 (1998).
Johnson, et al., "Primary plasma cell leukemia: morphologic, immunophenotypic, and cytogenetic features of 4 cases treated with chemotherapy and stem cell transplantation," Annals of Diagnostic Pathology, 10: 263-268 (2006).

(56) References Cited

OTHER PUBLICATIONS

Johnson & Johnson, Janssen to Demonstrate Breadth of Oncology Portfolio with 42 Clinical Data Presentation at the 2014 American Society of Hematology (ASH) Annual Meeting, San Francisco, California (Nov. 2014).
Jones, et al., "Depletion of CD25+ regulatory calls results in suppression of melanoma growth and induction of autoreactivity in mice," Cancer Immunity, 2: 1 (2002). Abstract.
Jones, et al., "Replacing the complementarity-determining regions in a human antibody with those from a mouse," Nature, 321: 522-525 (1986).
Kita et al., "Antitumor effects of YM155, a novel suppressant, against human aggressive non-Hodgkin Lymphoma," Leukemia Research, vol. 35, pp. 787-792, (2011).
Kita, A., et al., "Sepantronium Bromide (YM155) Enhances Response of Human B-Cell Non-Hodgkin Lymphoma to Rituximab," The Journal of Pharmacology and Experimental Therapeutics, vol. 343; No. 1; 178-183 (2012).
Konapleva, et al., "Ligation of Cell Surface CD38 Protein with Agonistic Monoclonal Antibody Induced a Cell Growth Signal in Myeloid Leukemia Cells," The Journal of Immunology, 161: 4702-4708 (1998).
Kong, S.Y., et al., "Daratumumab Directly Induces Human Multiple Myeloma Cell Death and Acts Synergistically with Conventional and Novel Anti-Myeloma Drugs," Blood, vol. 116; Abstract 3013 (2010).
Konopleva, et al., "CD38 in Hematopoietic Malignancies," Chemical Immunol. Basel Karger, 75: 189-206 (2000).
Kreitman, et al., Phase I Trial of Recombinant Immunotoxin Anti-Tac (Fv)-PE38 (LMB-2) in Patients with Hematologic Malignancies, Journal of Clinical Oncology, 18: 1622-1636 (2000).
Krejcik, J. et al., "Daratumumab depletes CD38+ immune regulatory cells, promotes T-cell expansion, and skews T-cell repertoire in multiple myeloma," Blood, vol. 128; No. 3; 384-394 (2016).
Krejcik, J. et al., Immunomodulatory Effects and Adaptive Immune Response to Daratumumab in Multiple Myeloma,: Blood, vol. 126; 3037; 7 pages (2015).
Kreuger, et al., "Successful in vivo blockade of CD25 (high-affinity interleukin 2 receptor) on T cells by administration of humanized anti-Tac antibody to patients with psoriasis," Journal of American Academy of Dermatology, 41(3): 448-458 (2000).
Kropff, et al., "Bortezomib in combination with dexamethoasone for relapsed multiple myeloma," Leukemia Research, 29: 587-590 (2005).
Kumar, S. et al., "Expression of CD52 on plasma cells in plasma cell proliferative disorders," Blood, vol. 102; No. 3; 1075-1077 (2003).
Kupiec-Weglinski, "CD25-Targeted Therapy Revisited," Transplantation, 69(3): 328-330 (2000).
Lakshman, A. et al., "Efficacy of daratumumab-based therapies in patients with relapsed, refractory multiple myeloma treated outside of clinical trials," Am J. Hematol., vol. 92; 1146-1155 (2017).
Lande, et al., "CD38 ligation plays a direct role in the induction of IL-1β, I-6, and IL-10 secretion in resting human monocytes," Cellular Immunology, 220: 30-38 (2002).
Laubach, J.P., "Daratumumab granted breakthrough drug status," Expert Opinion Investig. Drugs, vol. 23; No. 4; 445-452 (2014).
Laurie, et al., "The role of CD4+CD25+ immunoregulatory T cells in the induction of autoimmune gastritis," Immunology and Cell Biology, 80: 567-573 (2002).
Lazar, et al., "Transforming Growth Factor α: Mutation of Aspartic Acid 47 and Leucine 48 Results in Different Biological Activities," Molecular and Cellular Biology, 8(3): 1247-1252 (1988).
Leonard, et al., "Molecular cloning and expression of cDNAs for the human interleukin-2 receptor," Nature 311(18): 626-631 (1984).
Leveque "Subcutaneous Administration of Anticancer Agents" Anticancer Research, Departments of Pharmacy, University Hospital, Strasbourg, France, vol. 34, pp. 1579-1586 (2014).
Li, et al., "Creation of Patient Derived AML Xenografts Displaying Distinct Phenotypes and Genotypes," Blood, vol. 122: No. 21, p. 5018 (2013).

Lin, et al., "Structure-Function Relationships in Glucagon: Properties of Highly Purified Des-Hisl-, Monoiodi-, and [Des-Asn28, Thr29](homoserine lactone27)-glucagon," Biochemistry, 14(9): 1559-1563 (1975).
Lippincott-Schwartz, "Antibodies as cell Biological Tools," Current Protocols in Cell Biology, 16.0.1-16.0.2, (2002).
Liu et al., "Induction of Chemoresistance by All-Trans Retinoic Acid Via a Noncanonical Signaling in Multiple Myeloma Cells," PLOS ONE, vol. 9, No. 1, p. Article No. e85571, Jan. 2014.
Lonberg, et al., "Antigen-specific human antibodies from mice comprising four distinct genetic modifications," Nature: 308: 856-859 (1994).
Lu et al., "Issues Related to Targeted Delivery of Proteins & Peptides," The AAPS Journal, vol. 8, No. 3, Article 55, pp. E466-E478, Jul. 21, 2006.
MacCallum, et al., "Antibody-antigen Interactions: Contact Analysis and Binding Site Topography," Journal of Molecular Biology, 262, 732-745 (1998).
Malavasi, et al., "Human CD38: a glycoprotein in search of a function," Immunology Today, 15(3): 95-97 (1994).
Maloney, et al., "Antibody Therapy for Treatment of Multiple Myeloma," Semin Hematol. 36 (Suppl. 3): 30-33 (1999).
Matas-Cespedes, A. et al., "The human CD38 monoclonal antibody daratumumab shows anti-tumor activity and hampers leukemia-microenvironment interactions in chronic lympocytic leukemia," Clinical Cancer Research, vol. 23; No. 6; 1493-1505 (2017).
Mauri, C. and Menon, M., "The expanding family of regulatory B cells," International Immunology, vol. 27; No. 10; 479-486 (2015).
McCarthy, P.L., "Strategies for induction, autologous hematopoietic stem cell transplantation, consolidation, and maintenance for transplantation-eligible multiple myeloma patients", Hematology, vol. 2013, NI. 1, pp. 496-503 (Dec. 2013).
McKelvey, et al., "Hydroxyldaunomycian (Adriamycin) Combination Chemotherapy in Malignant Lymphoma," Cancer, vol. 38, No. 4, pp. 1485-1493 (Oct. 1976).
Mills, et al., Characterization of Monoclonal Antibodies that Inhibit CD38 ADp-ribosyl Cyclase Activity, LSSURP HLB Program, Department of Pharmacology, University of Minnesota, 2007.
Mikhael et al., "Cyclophosphamide-Bortezomib-Dexamethasone (CYBORD) Produces Rapid and Complete Hematological Response in Patients with AL Amyloidosis," Blood 119:4391-94 (Year: 2012).
Mohammad et al., "The Addition of Bryostatin 1 to Cyclophosphamide, Doxorubicin, Vincristine, and Prednisone (CHOP) Chemotherapy Improves Response in a CHOP-resistant Human Diffuse Large Cell Lymphoma Xenograft Model," Clinical Cancer Research, vol. 6, 4950-4956 (Dec. 2000).
Morrison, et al., "Chimeric human antibody molecules: Mouse antigen-binding domains with human constant region domains," Proceedings of the National Academy of Science USA, vol. 81; 6851-6855 (1984).
Mrowietz, "Treatment of Severe Psoriasis with Anti-CD25 Monoclonal Antibodies," Arch. Dermatology, 136: 675-676 (2000).
Mukherjee, et al., "Production and Characterization of Protective Human Antibodies against Shiga Toxin 1," Infection and Immunity, 70(10): 5896-5899 (2012).
Muyldermans, "Single domain camel antibodies: current status," Reviews in molecular Biotechnology, 74: 277-302 (2001).
Muyldermans, et al., "Recognition of antigens by single-domain antibody fragments: the superfluous luxury of paired domains," Trends in Biochemical Sciences, 26(4): 230-235 (2001).
Najjar et al., "Abstract P227: Accumulation of MDSC Subsets in Renal Cell Carcinoma Correlates with Grade and Progression Free Survival, and is Associated with Intratumoral Expression of IL-1β, IL-8 and CXCL5," Journal for Immunotherapy of Cancer, Nov. 6, 2014, vol. 2, p. 110-112.
Nijhof, et al.,"Modulation of CD 38 Expression Levels on Multiple Myeloma Tumor Cells by All-Trans Retinoic Acid Improves the Efficacy of the Anti-CD 38 Monoclonal Antibody Daratumumab," Blood, American Society of Hematology, US, vol. 124, No. 21, p. 2096, Dec. 6, 2014. (Abstract Only).
Nijhof, I.S. et al., Combination of the anti-CD38 monoclonal antibody daratumumab and all-trans retinoic acid (Abstract in Proceedings of the AACR Special Conference on Hematologic

(56) References Cited

OTHER PUBLICATIONS

Malignancies: Translating Discoveries to Novel Therapies). Clin Cancer Res, Sep. 20, 2014, vol. 21, No. 17 Suppl, pp. Abstract A12; Abstract.
Nijhof I.S. et al.: "Upregulation of CD38 expression on multiple myeloma cells by all-trans retinoic acid improves the efficacy of daratumumab", Leukemia, vol. 29, No. 10, ISSN 1476-5551, pp. 2039-2049 (2015).
Nijhof, I.S. et al., Preclinical Evidence for the Therapeutic Potential of CD38-Targeted Immuno-Chemotherapy in Multiple Myeloma Patients Refractory to Lenalidomide and Bortezomib. Clin Cancer Res., Nov. 14, 2014, vol. 21, No. 12, pp. 2802-2810.
Nikaido, et al., "Molecular cloning of cDNA encoding human interleukin-2 receptor," Nature, 311: 631-635 (1984).
Offidani et al., "An evidence-based review of ixazomib citrate and its potential in the treatment of newly diagnosed multiple myeloma," OncoTargets and Therapy, vol. 7, pp. 1793-1800, 2014.
Onizuka, et al., "Tumor Rejection by in Vivo Administration of Anti-CD25 (Interleukin-2 Receptor α Monoclonal Antibody," Cancer Research, 59: 3128-3133 (1999).
Orlowski, "The Ubiquitin Proteasome pathway from Bench to Bedside," American Society of Hematology, 220-225 (2005).
Ostberg, et al., "Human and humanized monoclonal antibodies: preclinical studies and clinical experience," Biochemical Society Transactions, 23: 1-6 (1995).
Padlan, et al., "Identification of specificity-determining resides in antibodies," FASEB Journal, 9: 135-139 (1995).
Palumbo, A. et al., "Daratumumab, Bortezomib, and Dexamethasone for Multiple Myeloma," The New England Journal of Medicine, vol. 375; No. 8; 754-766 (2016).
Parren et al., "HuMax-CD38, a new human CD38 monoclonal antibody, effectively mediates killing of multiple myeloma and plasma cell leukemia cells," American Society of Hematology 47th annual meeting, Atlanta, Georgia, USA, Dec. 10-13, 2005 (Abstract).
Parren, et al., HuMax-CD3 8, Myconos, Jun. 26, 2006.
Parren, et al., HuMax-CD38, Torino, Jun. 8-10, 2006.
Pascual, et al., "Anti-interleukin-2 receptor antibodies: basiliximab and daclizumab," Nephrology Dial. Transplant, 16: 1756-1760 (2001).
Patton, D.T. et al., "The P13K p110δ Regulates Expression of CD38 on Regulatory T Cells," PLOS one, vol. 6; No. 3; e17359; 8 pages (2011).
Paul, M.D., "Fundamental Immunology," Chapter 9, Raven Press, New York, 3rd ed., 292-295 (1993).
Peipp, et al., "Fully Human CD38 Antibodies Efficiently Trigger ADCC and CDC of Multiple Myeloma Cell Lines and Primary Tumor Cells (Poster)," Blood, vol. 106(11): 944A, 47th Annual Meeting of the American Society of Hematology, 2005; published (Nov. 16, 2005).
Peipp, et al., Fully Human CD38 Antibodies Efficiently Trigger ADCC and CDC of Multiple Myeloma and Plasma Cell Leukemia Cells (Poster 2) Conference proceedings, poster presentation at the 2005 Annual Meeting of the American Society of Hematology, (Dec. 12, 2005).
Peipp, et al., 47th Annual Meeting of the American Society of Hematology, Atlanta, GA, Dec. 10-13, 2005, (Meeting Abstract).
Peng, et al., "Oncolytic measles viruses displaying a single-chain antibody against CD38, a myeloma cell marker," Blood, 101, 2557-2562 (2003).
Phase 1/2 Dose Escalation and Efficacy Study of Anti-CD38 Monoclonal Antibody in Patients With Selected CD38+ Hematological Malignancies, First posted Mar. 10, 2010, ClinicalTrials.gov. identifier No. NCT01084252.
Prosniak, M. et al.: "Development of a Cocktail of Recombinant-Expressed Human Rabies Virus-Neutralizing Monoclonal Antibodies for Postexposure Prophylaxis of Rabies," The Journal of Infectious Diseases, vol. 187; 53-56 (2003).
Richardson, et al., "Daratumumab," Drugs of the Future, 38(8): 545-554 (2013).
Rituxan Hycela Label, "Highlights of prescribing information. RITUXAN HYCELA™ (rituximab and hyaluronidase human) injection, for subcutaneous use," 32 pages (Jun. 2017).
Sachchithanantham, S. et al., "Use of Plasma Cell Immunophenotype as Prognostic Markers in Patients with Systemic AL Amyloidosis," Blood, vol. 122; p. 3120 (2013).
Salar et al., "Comparison of Subcutaneous Versus Intravenous Administration of Rituximab as Maintenance Treatment for Follicular Lymphoma: Results From a Two-Stage, Phase IB Study," Journal of Clinical Oncology, vol. 32, No. 17, pp. 1782-1791, (Jul. 10, 2014).
Sanchez-Gonzalez et al., "Rituximab subcutaneous in B-Cell non-Hodgkin lymphoma: clinical experience in a single center," Leukemia & Lymphoma, vol. 59, No. 4, pp. 1019-1021 (2018).
San-Miguel, J. et al., "Efficacy by cytogenetic risk status for daratumumab in combination with lenalidomide and dexamethasone or bortezomib and dexamethasone in relapsed or refractory multiple myeloma," EHA22; EHA Learning Center; Abstract; 4 pages (2017).
San-Miguel, J., "New approaches to myeloma treatment in 2017," EHA Learning Center; Abstract; 4 pages (2017).
Schonland, S., et al., "Detection and Charaterization of Plasma Cell and B Cell Clones in Patients with Systemic Light Chain Amyloidosis Using Flow Cytometry," Blood, vol. 142, p. 2068 (2014).
Sher, T. et al., "First report of safety and efficacy of daratumumab in 2 cases of advanced immunoglobulin light chain amyloidosis," Blood, vol. 128; No. 15; 1987-1989 (2016).
Shields, et al., "High Resolution mapping of the binding site on human IgG1 for FcγRi, FcγRII, FcγRIII, and FcRn and design of IgG1 variants with improved binding to the FcγR," J. Biol, Chem., vol. 276, No. 9, pp. 6591-6604, (2001).
Shpilberg, et al., "Subcutaneous administration of rituximab (MabThera) and trastuzumab (Herceptin) using hyaluronidase," British Journal of Cancer, vol. 109, pp. 1556-1561, 2013.
Shubinsky, et al., "The CD38 Lymphocyte Differentiation Marker: New Insight into Its Ectoenzymatic Activity and Its Role as a Signal Transducer," Immunity, 7: 315-324 (1997).
Skeel, Handbook of Cancer Gliemotherapy, 3rd edition, Little, Brown & Co., pp. 330-350 (1991).
Sonneveld, P. and Annemiek Broijl, "Treatment of Relapsed and Refractory Multiple Myeloma," Review Article, Leaders in Hematology, review series, Haematologica, 101(4):396-406 (2016).
Spencer, A. et al., "Daratumumab plus bortezomib and dexamethasone versus bortezomib and dexamethasone in relapsed or refractory multiple myeloma: updated analysis of CASTOR," Haematologica, vol. 103; No. 12; 2079-2087 (2018).
Strome, S.E. et al., "A Mechanistic Perspective of Monoclonal Antibodies in Cancer Therapy Beyond Target-Related Effects," The Oncologist, vol. 12; 1084-1095 (2007).
Tabernero, et al., "Adult precursor B-ALL with BCR/ABL gene rearrangements displays a unique immunophenotype based on the pattern of CD10, CD34, CD13, and CD38 expression," Leukemia, vol. 15, No. 3, pp. 406-414, (2001).
Talmadge, J.E. and Gabrilovich, D.I, "History of myeloid-derived suppressor cells," Nature Reviews, vol. 13; 739-752 (2013).
Terhorst, et al., "Biochemical Studies of the Human Thymocyte Cell-Surface Antigens T6, T9 and T10," Cell, 23: 771-780 (1981).
Topalian, S.L., et al., "Immune Checkpoint Blockade: A Common Denominator Approach to Cancer Therapy," Cancer Cell, vol. 27; 450-461 (2015).
Usmani, et al., "Clinical efficacy of daratumumab monotherapy in patients with heavily pretreated relapsed or refractory multiple myeloma," Blood, vol. 128, No. 1, pp. 37-44, (May 23, 2016).
Usmani, S.Z. et al., "Efficacy of Daratumumab, Lenalidomide, and Dexamethasone Versus Lenalidomide and Dexamethasone in Relapsed or Refractory Multiple Myeloma Patients with 1 to 3 Prior Lines of Therapy: Updated Analysis of Pollux," Blood, vol. 128; No. 22; 1151; 10 pages (2016).
Vadjos, et al., "Comprehensive Functional Maps of the Antigen-binding Site of an Anti-ErbB2 Antibody Obtained with Shotgun Scanning Mutagenesis," Journal of Molecular Biology, 320: 415-428 (2002).
Van Bueren, et al., "Direct In Vitro Comparison of Daratumumab With Surrogate Analogs of Anti-CD38 Antibodies," New Evidence

(56) References Cited

OTHER PUBLICATIONS

Oncology Issue, Apr. 2015 [retrieved on Feb. 3, 2016] Retrieved from the Internet: URL: Http:///www.newevidence.com/oncology/direct-in-vitro-comparison-of-daratumumab-with-surrogate-analogs-of-anti-cd38-antibodies>.

Van de Donk et al., "Monoclonal antibodies targeting CD38 in hematological malignancies and beyond," Immunological Reviews, vol. 270, pp. 95-112, (2016).

Venner et al., "Cyclophosphamide, bortezomib, and dexamethasone therapy in AL amyloidosis is associated with high clonal response rates and prolonged progression-free survival," Blood, vol. 119, No. 9, pp. 4387-4390, (2012).

Vorre, et al., "Multiple Daratumumab Abstracts to be Presented at EHA," ArrayDiagnostica, Abstract Only (2014).

Wagner, V., et al., "Preclinical Efficacy of Sepantronium Bromide (YM155) in multiple myeloma is conferred by down regulation of Mcl-1," Oncotarget, 5(21): 10237-10250 (2014).

Wagner et al., Survivin in Multiple Myeloma: Prognostic and Therapeutic Implications, vol. 118, Article 137, 2011 (Abstract Only).

WCJ van de Donk, "A Phase 1 and Phase 2 Study of Daratumumab in Combination With All-Trans Retinoic Acid in Relapsed/Refractory Multiple Myeloma," Clinical Trials.gov Identification No. NCT02751255; (First posted Apr. 26, 2016).

Weisel, K.C. et al., "Efficacy of daratumumab in combination with lenalidomide plus dexamethasone (DRd) or bortezomib plus dexamethasone (RVd) in relapsed or refractory multiple myeloma (RRMM) based on cytogenetic risk status," Journal of Clinical Oncology, vol. 35; No. 15; 8006; Abstract (2017).

Ye et al, "Abstract P240: Treg Increases HepG2 Cell Growth by RANK-RANKL pathway." Journal for Immunotherapy of Cancer, vol. 2; Suppl 3; p. 240 (Nov. 6, 2014).

International Search Report and Written Opinion dated Feb. 12, 2019 for International Application No. PCT/US2018/058561, entitled "Methods of Treating High Risk Multiple Myeloma".

International Preliminary Report on Patentability dated May 8, 2018 for International Application No. PCT/US2016/59893, entitled "Subcutaneous Formulations of Anti-CD38 Antibodies and Their Uses".

International Search Report and Written Opinion dated Jan. 24, 2017 for International Application No. PCT/US2016/59893, entitled "Subcutaneous Formulations of Anti-CD38 Antibodies and Their Uses".

International Preliminary Report on Patentability dated Dec. 26, 2017 for International Application No. PCT/US2016/038702, entitled "Combination Therapies for Heme Malignancies With Anti-CD38 Antibodies and Survivin Inhibitors".

International Search Report and Written Opinion dated Nov. 29, 2016 for International Application No. PCT/US2016/038702, entitled "Combination Therapies for Heme Malignancies With Anti-CD38 Antibodies and Survivin Inhibitors".

International Preliminary Report on Patentability dated Mar. 14, 2017 for International Application No. PCT/US2015/048899, entitled "Combination Therapies With Anti-CD38 Antibodies".

International Search Report and Written Opinion dated Apr. 8, 2016 for International Application No. PCT/US2015/048899, entitled "Combination Therapies With Anti-CD38 Antibodies".

International Preliminary Report on Patentability dated Nov. 21, 2017 for International Application No. PCT/US2016/033544, entitled "Anti-CD38 Antibodies for Treatment of Light Chain Amyloidosis and Other CD38-Positive Hematological Malignancies".

International Search Report and Written Opinion dated Oct. 24, 2016 for International Application No. PCT/US2016/033544, entitled "Anti-CD38 Antibodies for Treatment of Light Chain Amyloidosis and Other CD38-Positive Hematological Malignancies".

International Preliminary Report on Patentability dated Jun. 6, 2016 for International Application No. PCT/US2015/063371, entitled "Anti-CD38 Antibodies for Treatment of Acute Myeloid Leukemia".

International Search Report and Written Opinion dated Feb. 19, 2016 for International Application No. PCT/US2015/063371, entitled "Anti-CD38 Antibodies for Treatment of Acute Myeloid Leukemia".

International Preliminary Report on Patentability dated Dec. 26, 2017 for International Application No. PCT/US2016/039165, entitled "Immune Modulation and Treatment of Solid Tumors With Antibodies That Specifically Bind CD38".

International Search Report and Written Opinion dated Oct. 14, 2016 for International Application No. PCT/US2016/039165, entitled "Immune Modulation and Treatment of Solid Tumors With Antibodies That Specifically Bind CD38".

International Preliminary Report on Patentability dated Sep. 6, 2016 for International Application No. PCT/US2015/017425, entitled "Anti-CD38 Antibodies for Treatment of Acute Lymphoblastic Leukemia".

International Search Report and Written Opinion dated Sep. 21, 2015 for International Application No. PCT/US2015/017425, entitled "Anti-CD38 Antibodies for Treatment of Acute Lymphoblastic Leukemia".

International Search Report and Written Opinion dated Sep. 25, 2017 for International Application No. PCT/EP2017/066063, entitled "Treatment Of IgE-Mediated Diseases With Antibodies That Specifically Bind CD38".

International Preliminary Report on Patentability dated Sep. 6, 2016 for International Application No. PCT/US2015/017420, entitled "Combination Therapies With Anti-CD38 Antibodies".

International Search Report and Written Opinion dated Jul. 8, 2015 for International Application No. PCT/US2015/017420, entitled "Combination Therapies With Anti-CD38 Antibodies".

Intellectual Property Office of Singapore Written Opinion dated Apr. 17, 2018 for Application No. 11201701867S, entitled "Combination Therapies with Anti-CD38 Antibodies".

Supplementary European Search Report dated Feb. 21, 2018 for European Application No. EP 15839752, entitled "Combination Therapies with Anti-CD38 Antibodies".

Non Final Office Action for U.S. Appl. No. 15/340,290 dated Nov. 20, 2017.

Final Office Action for U.S. Appl. No. 15/340,290 dated May 16, 2018.

Non Final Office Action for U.S. Appl. No. 15/340,290 dated Oct. 10, 2018.

Non Final Office Action for U.S. Appl. No. 15/366,474 dated Nov. 20, 2017.

Final Office Action for U.S. Appl. No. 15/366,474 dated May 16, 2018.

Applicant Initiated Interview for U.S. Appl. No. 15/366,474 dated Sep. 17, 2018.

Non Final Office Action for U.S. Appl. No. 15/366,474 dated Oct. 11, 2018.

Non Final Office Action for U.S. Appl. No. 15/189,577 dated Oct. 31, 2017.

Final Office Action for U.S. Appl. No. 15/189,577 dated Apr. 13, 2018.

Non Final Office Action for U.S. Appl. No. 15/189,577 dated Sep. 28, 2018.

Non Final Office Action for U.S. Appl. No. 14/847,428 dated Sep. 23, 2016.

Non Final Office Action for U.S. Appl. No. 15/386,391 dated Jun. 18, 2018.

Non Final Office Action for U.S. Appl. No. 15/160,476 dated Sep. 15, 2017.

Non Final Office Action for U.S. Appl. No. 15/160,476 dated Nov. 5, 2018.

Final Office Action for U.S. Appl. No. 15/160,476 dated Apr. 23, 2018.

Non Final Office Action for U.S. Appl. No. 14/956,890 dated Nov. 25, 2016.

Final Office Action for U.S. Appl. No. 14/956,890 dated Jul. 24, 2018.

Non Final Office Action for U.S. Appl. No. 15/340,214 dated May 16, 2018.

(56) References Cited

OTHER PUBLICATIONS

Non Final Office Action for U.S. Appl. No. 14/629,965 dated Dec. 21, 2015.
Final Office Action for U.S. Appl. No. 14/629,965 dated Apr. 29, 2016.
Notice of Allowance for U.S. Appl. No. 14/629,965 dated Apr. 13, 2017.
Non Final Office Action for U.S. Appl. No. 15/445,225 dated Jun. 29, 2018.
Final Office Action for U.S. Appl. No. 15/445,225 dated Dec. 17, 2018.
Non Final Office Action for U.S. Appl. No. 15/651,333 dated Sep. 27, 2018.
Final Office Action for U.S. Appl. No. 15/386,391 dated Dec. 28, 2018.
Final Office Action for U.S. Appl. No. 14/956,890 dated Jan. 14, 2019.
Notice of Allowance for U.S. Appl. No. 15/651,333 dated Feb. 21, 2019.
Notice of Allowance for U.S. Appl. No. 15/189,577 dated Mar. 5, 2019.
Final Office Action for U.S. Appl. No. 15/340,290 dated Mar. 11, 2019.
Notice of Allowance for U.S. Appl. No. 15/386,391 dated Mar. 29, 2019.
Notice of Allowance for U.S. Appl. No. 15/340,290 dated May 22, 2019.
Notice of Allowance for U.S. Appl. No. 15/651,333 dated May 31, 2019.
Abdi, J. et al., "Drug resistance in multiple myeloma: latest findings and new concepts on molecular mechanisms," Oncotarget, vol. 4; No. 12; 2186-2207 (2013).
Chaulagain, C.P. and Comenzo, R.L., "New Insights and Modern Treatment of AL Amyloidosis," Curr Hematol Malig Rep, vol. 8; 291-298 (2013).
Chiarugi, A. et al., "The NAD metabolome—a key determinant of cancel cell biology," Nature Reviews, vol. 12; 741-752 (2012).
Comenzo, R.L. et al., "Consensus guidelines for the conduct and reporting of clinical trials in systemic light-chain amyloidosis," Leukemia, vol. 26; 2317-2325 (2012).
Ettinger, R. et al., "Pathogenic mechanisms of IgE-mediated inflammation in self-destructive autoimmune responses," Autoimmunity, vol. 50; No. 1; 25-36 (2017).
Gupta, R. et al., "The Economic Impact of Childhood Food Allergy in the United States," JAMA Pediatrics, vol. 167; No. 11; 1026-1031 (2013).
Holgate, S.T., "New strategies with anti-IgE in allergic diseases," World Allergy Organization Journal, vol. 7; No. 17; 6 pages (2014).
Inaba, H. et al., "Acute lymphoblastic leukaemia," Lancet, vol. 381; 27 pages (2013).
Lepenies, B. and Jacobs, T., "The Role of Negative Costimulators During Parasitic Infections," Endocrine, Metabolic & Immune Disorders—Drug Targets, vol. 8; 279-288 (2008).
Manier, S. et al., "Bone Marrow Microenvironment in Multiple Myeloma Progession," Journal of Biomedicine and Biotechnology, vol. 2012; 5 pages (2012).
Merlini, G. and Bellotti, V., "Molecular Mechanisms of Amyloidosis," The New England Journal of Medicine, vol. 349; No. 6; 583-596 (2003).
Mills, E.N.C. et al., "The prevalence, cost and basis of food allergy across Europe," Allergy, vol. 62; 717-722 (2007).
Patel, J.P., "Prognostic Relevance of Integrated Genetic Profiling in Acute Myeloid Leukemia," The New England Journal of Medicine, vol. 366; No. 12; 1079-1089 (2012).
Sicherer, S.H. and Sampson, H.A., "Food allergy: Epidemiology, pathogenesis, diagnosis, and treatment," J. Allergy Clin Inmmunol, vol. 133; 291-307 (2014).
Swaika, A. et al., "Current state of anti-PD-L1 and anti-PD-1 agents in cancer therapy," Molecular Immunology, vol. 67; 4-17 (2015).

The Cancer Genome Atlas Research Network et al., "Genomic and Epigenomic Landscapes of Adult De Novo Acute Myeloid Leukemia," N. Engl. J. Med, vol. 368; No. 22; 2059-2074 (2013).
Wang, L. et al., "VISTA, a novel mouse Ig superfamily ligand that negatively regulates T cell responses," J. Exp. Med., vol. 208; No. 3; 577-592 (2011).
Wei, W. et al., "Roles and mechanisms of the CD38/cyclic adenosine diphosphate ribose/Ca2+ signaling pathway," World Journal of Biological Chemistry, vol. 5; No. 1; 58-67 (2014).
Final Office Action for U.S. Appl. No. 15/160,476 dated Jun. 14, 2019.
Notice of Allowance for U.S. Appl. No. 15/445,225 dated Jul. 29, 2019.
Notice of Allowance for U.S. Appl. No. 15/386,391 dated Jul. 30, 2019.
Non-Final Office Action for U.S. Appl. No. 14/956,890 dated Jul. 30, 2019.
Notice of Allowance for U.S. Appl. No. 15/189,577 dated Sep. 12, 2019.
Notice of Allowance for U.S. Appl. No. 15/651,333 dated Oct. 9, 2019.
ClinicalTrials.gov, "Daratumumab in Combination with ATRA (DARA/ATRA)," Identifier: NCT02751255; First posted: Apr. 26, 2016. (11 pages).
ClinicalTrials.gov, "A Study of Daratumumab with the Addition of Recombinant Human Hyaluronidase (rHuPH20) for the Treatment of Participants with Relapsed or Refractory Multiple Myeloma," Identifier: NCT02519452; First Posted: Aug. 11, 2015. (13 pages).
ClinicalTrials.gov, "A Study to Evaluate Subcutaneous Daratumumab in Combination with Standard Multiple Myeloma Treatment Regimens," Identifier: NCT03412565, First Posted: Jan. 26, 2018 (16 pages).
ClinicalTrials.gov, "A Phase 1 Study to Assess the Safety, Tolerability, and Pharmacokinetics of TAK-079 in Healthy Participants," Identifier: NCT02219256, Latest version posted: Mar. 22, 2017, (13 pages).
Dispenzieri, A. et al., "Treatment of Immunoglobulin Light Chain Amyloidosis: Mayo Stratification of Myeloma and Risk-Adapted Therapy (mSMART) Consensus Statement," Mayo Clin Proc., vol. 90; No. 8; 1054-1081 (2015).
Fujioka, Y. and Kurokawa, M., "Follicular lymphoma presenting with massive splenomegaly," International J Hematol, vol. 95; 3-4 (2012).
Kaufman, G.P. et al., "Daratumumab yields rapid and deep hematologic responses in patients with heavily pretreated AL amyloidosis," Blood, vol. 130; No. 7; 900-902 (2017).
Machida, H. et al., "Aggressive plasma cell leukemia with cleaved, multilobated and monocytoid nuclei," International Journal of Hematol., vol. 73; Suppl 1; 158; Abstract No. 411 (2001).
Mai, E. et al., "Phase III trial of bortezomib, cyclophosphamide and dexamethasone (VCD) versus bortezomib, doxorubicin and dexamethasone (Pad) in newly diagnosed myeloma," Leukemia, vol. 29; 1721-1729 (2015).
Park, S. et al., "Successful Treatment by Rituximab of an Ebv-Related Lymphoma after Autologous Transplantation for Angioimmunoblastic T-Cell Lymphoma," International Journal of Hematol., vol. 76; Suppl. 1; 118; Abstract No. P340 (2002).
Rai, S. et al., "Successful Allogeneic Hematopoietic Stem Cell Transplantation in a Young Patient with Richter Syndrome Presenting with Chronic Lymphocytic Leukemia and Diffuse Large B-Cell Lymphoma with Different Cell Origins," Intern Med, vol. 52; 273-276 (2013).
Saito, M. et al., "A Case of Retroperitoneal Extramedullary Plasmacytoma," Acta Urol. Jpn., vol. 49; 735-739 (2003).
Smithson, G. et al., "TAK-079 is a high affinity monoclonal antibody that effectively mediates CD38+ cell depletion," Journal of Immunol., vol. 198; Suppl. 1; 224.20; Abstract (2017).
Usmani, S.Z. et al., "Open-Label, Multicenter, Dose Escalation Phase Ib Study to Assess the Subcutaneous Delivery of Daratumumab in Patients (pts) with Relapsed or Refractory Multiple Myeloma," Blood, vol. 128; No. 22; 1149 (2016).

(56) References Cited

OTHER PUBLICATIONS

Usmani, S.Z. et al., "Subcutaneous delivery of daratumumab in relapsed or refractory multiple myeloma," Blood, vol. 134; No. 8; 668-677 (2019).
International Preliminary Report on Patentability dated Jan. 10, 2019 for International Application No. PCT/EP2017/066063, entitled "Treatment of IgE-Mediated Diseases With Antibodies That Specifically Bind CD38".
International Preliminary Report on Patentability dated May 14, 2020 for International Application No. PCT/US2018/058561, entitled "Methods of Treating High Risk Multiple Myeloma".
International Search Report and Written Opinion dated Apr. 24, 2020 for International Application No. PCT/US2019/056838, entitled "Method of Providing Subcutaneous Administration of Anti-CD38 Antibodies".
Notice of Allowance for U.S. Appl. No. 15/386,391 dated Nov. 18, 2019.
Notice of Allowance for U.S. Appl. No. 15/445,225 dated Dec. 4, 2019.
Notice of Allowance for U.S. Appl. No. 15/189,577 dated Dec. 19, 2019.
Non Final Office Action for U.S. Appl. No. 15/160,476 dated Dec. 20, 2019.
Final Office Action for U.S. Appl. No. 14/956,890 dated Jan. 7, 2020.
Non-Final Office Action for U.S. Appl. No. 15/798,670 dated Jan. 22, 2020.
English translation of Office Action for JP Application No. 2016-554350, dated Nov. 27, 2018.
Notice of Allowance for U.S. Appl. No. 15/445,225 dated Mar. 25, 2020.
Notice of Allowance for U.S. Appl. No. 15/189,577 dated Mar. 31, 2020.
Notice of Allowance for U.S. Appl. No. 15/160,476 dated May 4, 2020.
Notice of Allowance for U.S. Appl. No. 16/380,994 dated May 12, 2020.
Notice of Allowance for U.S. Appl. No. 16/460,754 dated May 18, 2020.
Notice of Allowance U.S. Appl. No. 15/445,225 dated Jul. 15, 2020.
Almagro, J.C. and Fransson, J., "Humanization of antibodies," Frontiers in Bioscience, vol. 13; 1619-1633 (2008).
Berglund, L. et al., "The epitope space of the human proteome," Protein Science, vol. 17; 606-613 (2008).
Data show daratumumab achieved a pronounced overall response rate as a single-agent with tolerable safety profile in heavily pre-treated multiple myeloma patients, Johnson & Johnson Press release[online](retrived on Jul. 27, 2020), May 30, 2015, retrieved from the Internet<URL:https://www.jnj.com/media-center/press-releases/Data-show-daratumumab-achieved-a-pronounced-overall-response-rate-as-a-single-agent-with-tolerable-safety-profile-in-heavily-pre-treated-multiple-myeloma-patients>; 4 pages.
De Haart, S.J. et al., "Accessory Cells of the Microenvironment Protect Multiple Myeloma from T-Cell Cytotoxicity through Cell Adhesion-Mediated Immune Resistance," Clinical Cancer Research, vol. 19; No. 20; 5591-5601 (2013).
DMC recommends termination of study into daratumumab with atezolizumab to treat NSCLC, European Pharmaceutic Manufacturer[online](retrieved on Jul. 26, 2020), May 30, 2018, retrieved from the Internet<URL:https://www.epmmagazine.com/news/dmc-recommends-termination-of-study-into-daratumumab/>; 3 pages.
Palumbo, A. et al., "Daratumumab, Bortezomib, and Dexamethasone for Multiple Myeloma," The New England Journal of Medicine, vol. 375; No. 8; 754-766; Suppl. Material: the protocol; total pp. 119 (2016).
Sagaster, V. et al., "Bortezomib in relapsed multiple myeloma: response rates and duration of response are independent of a chromosome 13q-deletion," Leukemia, vol. 21; 164-168 (2007).

Tzartos, S.J., et al., "Epitope Mapping by Antibody Competition," Methods in Molecular Biology, vol. 66; 55-66 (1996).
Notice of Allowance for U.S. Appl. No. 14/956,890 dated Jul. 29, 2020.
Non-Final Office Action for U.S. Appl. No. 15/798,670 dated Aug. 7, 2020.
Notice of Allowance for U.S. Appl. No. 16/3 80,994 dated Aug. 12, 2020.
Non-Final Office Action for U.S. Appl. No. 16/162,355 dated Aug. 13, 2020.
Notice of Allowance for U.S. Appl. No. 16/460,754 dated Sep. 10, 2020.
Final Office Action for U.S. Appl. No. 15/798,670 dated Dec. 16, 2020.
International Preliminary Report on Patentability dated Apr. 29, 2021 for International Application No. PCT/US2019/056838, entitled "Method of Providing Subcutaneous Administration of Anti-CD38 Antibodies".
Non-Final Office Action for U.S. Appl. No. 15/798,670 dated Apr. 2, 2021.
Notice of Allowance for U.S. Appl. No. 16/162,355 dated Apr. 9, 2021.
Bookbinder, L.H. et al., "A recombinant human enzyme for enhanced interstitial transport of therapeutics," Journal of Controlled Release, vol. 114; 230-241 (2006).
CAS Registry Results, dated Oct. 9, 2020, Registry No. 757971-58-7, "36-482-Hvaluronoglucosaminidase PH20 (human)," 6 pages.
Chari, A., et al., "Subcutaneous Daratumumab (DARA) in Patients (Pts) With Relapsed or Refractory Multiple Myeloma (RRMM): Part 2 Update of the Open-label, Multicenter, Dose-escalation Phase lb Study (PAVO)", Poster Presented at the Annual Meeting of the American Society of Clinical Oncology (ASCO); Jun. 1-5, 2018; Chicago, Illinois.
ClinicalTrials.gov, "An Investigational Immuno-Therapy Study to Determine the Safety and Effectiveness of Nivolumab and Daratumumab in Patients with Multiple Myeloma," Identifier: NCT01592370, Latest version posted: Jun. 18, 2021 (10 pages).
Colson, K., "Treatment-related symptom management in patients with multiple myeloma: a review," Support Care Cancer, vol. 23; 1431-1445 (2015).
Dimopoulos, M.A. et al., "Daratumumab plus pomalidomide and dexamethasone versus pomalidomide and dexamethasone alone in previously treated multipled myeloma (APOLLO_: an open-label, randomised, phase 3 trial," Lancet Oncol, vol. 22; 801-812 (2021).
Faiman, B. et al., "Steroid-Associated Side Effects in Patients with Multiple Myeloma: Consensus Statement of the IMF Nurse Leadership Board," Clinical Journal of Oncology Nursing, vol. 12; No. 3; 53-63 (2008).
Hydase, Highlights and Prescribing Information, FDA Label, 6 pages (2005).
Jaccard, A. et al., "Efficacy of bortezomib, cyclophosphamide and dexamethasone in treatment-naïve patients with high-risk cardiac AL amyloidosis (Mayo Clinic stage III)," Haematologica, vol. 99; No. 9; 1479-1485 (2014).
Janssen to Demonstrate Breadth of Oncology Portfolio with 41 Clinical Data Presentations at the 2014 American Society of Hematology (ASH) Annual Meeting [online], Nov. 6. 2014, Internet:<URL: https://www.jnj.com/media-center/press-releases/janssen-to-demonstrate-breadth-of-oncology-portfolio-with-41-clinical-data-presentations-at-the-2014-american-society-of-hematology-ash-annual-meeting>.
Lonial, S. et al., "Monoclonal antibodies in the treatment of multiple myeloma: current status and future perspectives," Leukemia, vol. 30; 526-535 (2016).
Mateos, M. et al., "Daratumumab plus Bortezomib, Melphalan, and Prednisone for Untreated Myeloma," N England J Med, vol. 378; 518-528 (2018).
Ohaegbulam K C et al.: "Human cancer immunotherapy with antibodies to the PD-1 and PD-L1 pathway", Trends in Molecular Medicine, vol. 21 (1): 24-33 (2015).
San-Miguel, J., et al., "Subcutaneous Daratumumab in Patients with Relapsed or Refractory Multiple Myeloma: Part 2 Update of the Open-label, Multicenter, Dose Escalation Phase lb Study (PAVO)",

(56) References Cited

OTHER PUBLICATIONS

Poster Presented at the 23rd European Hematology Association (EHA) Annual Congress; Jun. 14-17, 2018; Stockholm, Sweden.
Wasserman, R.L., "Overview of recombinant human hyaluronidase-facilitated subcutaneous infusion of IgG in primary immunodeficiencies," Immunotherapv, vol. 6; No. 5; 553-567 (2014).
Declaration of Professor Paul Anthony Dalby, in Opposition Proceedings against European Patent No. 3370770, 20 pages (Dated May 2022).
Declaration of Professor Christian Jackisch, in Opposition Proceedings against European Patent No. 3370770, 8 pages (Dated May 10, 2022).
Reply to Notice of Opposition, filed in European Patent No. 3 370 770 B1, entitled: "Subcutaneous Formulations of Anti-CD38 Antibodies and Their Uses," 416 pages, dated May 12, 2022.
Non-Final Office Action for U.S. Appl. No. 15/798,670 dated Feb. 4, 2022.
Non Final Office Action for U.S. Appl. No. 16/840,153 dated Mar. 22, 2022.
Applicant Initiated Interview Summary for U.S. Appl. No. 16/840,153 dated Apr. 6, 2022.
Final Office Action for U.S. Appl. No. 16/312,133 dated May 12, 2022.
Applicant Initiated Interview Summary for U.S. Appl. No. 16/840,153 dated Jun. 8, 2022.
Non Final Office Action for U.S. Appl. No. 16/830,585 dated Mar. 17, 2022.
Non Final Office Action for U.S. Appl. No. 16/830,585 dated Mar. 15, 2022.
Non Final Office Action for U.S. Appl. No. 16/830,763 dated Mar. 17, 2022.
Non Final Office Action for U.S. Appl. No. 16/830,909 dated Mar. 17, 2022.
Non Final Office Action for U.S. Appl. No. 16/741,542 dated Jul. 12, 2022.
Non Final Office Action for U.S. Appl. No. 16/797,301 dated Jul. 28, 2022.
History of Changes for Study: NCT02252172, "Study Comparing Daratumumab, Lenalidomide, and Dexamethasone With Lenalidomide and Dexamethasone in Participants With Previously Untreated Multiple Myeloma," U.S. National Library of Medicine, ClinicalTrials.gov Archive, pp. 1-24, (Oct. 17, 2017).
Bittner, B. et al., "Development of a Subcutaneous Formulation for Trastuzumab—Nonclinical and Clinical Bridging Approach to the Approved Intravenous Dosing Regimen," Arzneimittelforschung, vol. 62; 401-409 (2012).
Bittner, B. et al., "Non-Clinical Pharmacokinetic /Pharmacodynamic and Early Clinical Studies Supporting Development of a Novel Subcutaneous Formulation for the Monoclonal Antibody Rituximab," Drug Res., vol. 64; 569-575 (2014).
CHMP Assessment Report for Herceptin (trastuzumab), 70 pages (2013).
CHMP Assessment Report for Mabthera (rituximab), 103 pages (2014).
ClinicalTrials.gov, "Daratumumab (HuMax-CD38) Safety Study in Multiple Myeloma," Identifier: NCT00574288; Latest version posted: Apr. 27, 2018 (10 pages).
Darzalex, Highlights and Prescribing Information, FDA Label, 24 pages (2015).
Davies, A. et al., "Pharmacokinetics and safety of subcutaneous rituximab in follicular lymphoma (SABRINA): stage 1 analysis of a randomised phase 3 study," The Lancet, vol. 15; 343-352 (2014).
Frost, G.I., "Recombinant human hyaluronidase (rHuPH20): an enabling platform for subcutaneous drug and fluid administration," Expert Opinion Drug Deliv., vol. 4; No. 4; 427-440 (2007).
Goel, M. et al., "Plasticity within the Antigen-Combining Site May Manifest as Molecular Mimicry in the Humoral Immune Response," The Journal of Immunology, vol. 173; 7358-7367 (2004).
Haller, M.F., "Converting Intravenous Dosing to Subcutaneous Dosing," Pharmaceutical Technology, 118-132 (2007).

Halozyme, "Halozyme Therapeutics Reports Selection of First Product Candidate Under Janssen Collaboration," Press Release, 4 pages (2015).
Hamizi, S. et al., "Subcutaneous trastuzumab: development of a new formulation for treatment of HER2-positive early breast cancer," OncoTargets and Therapy, vol. 6; 89-94 (2013).
Herceptin, Highlights and Prescribing Information, FDA Label, 33 pages (1998).
Hylenex, Highlights and Prescribing Information, FDA Label, 9 pages (2005).
Jackisch, C. et al., "Subcutaneous Administration of Monoclonal Antibodies in Oncology," Geburtsh Frauenhelk, vol. 74; 343-349 (2014).
Janssen Initiates Rolling Submission of Biologic License Application (BLA) for daratumumab with U.S. FDA for the Treatment of Multiple Myeloma, News Release, 3 pages (2015).
Khagi, Y. and Mark, T., "Potential role of daratumumab in the treatment of multiple myeloma," Onco Targets and Therapy, 1095-1100 (2014).
Khan, T. and Salunke, D.M., "Adjustable Locks and Flexible Keys: Plasticity of Epitope-Paratope Interactions in Germline Antibodies," The Journal of Immunology, vol. 192; 5398-5405 (2014).
Lokhorst, H.M. et al., "Targeting CD38 with Daratumumab Monotherapy in Multiple Myeloma," The New England Journal of Medicine, vol. 373; 1207-1219 (2015).
Mariuzza, R.A. eet al., "The Structural Basis of Antigen-Antibody Recognition," Ann. Rev. Biophys. Biophys. Chem., vol. 16; 139-159 (1987).
Nahi, H. et al., "An open-label, dose escalation phase lb study of subcutaneous daratumumab with recombinant human hyaluronidase in patients with relapsed or refractory multiple myeloma (PAVO)," Journal of Clinical Oncology, vol. 34; No. 15; 4 pages (2016).
Ocio, E.M. et al., "New drugs and novel mechanisms of action in multiple myeloma in 2013: a report from the International Myeloma Working Group )IMWG)," Leukemia, vol. 28; 525-542 (2014).
Ortolani, C., "CD38: Antigen: Flow Cytometry of Hematological Malignancies," Blackwell Publishing, 1st Edition, 68-70 (2011).
Phase 3 Columbia study Investigating a Subcutaneous Formulation of DARZALEX (daratumumab) Showed Non-Inferiority to Intravenous Administration in Patients with Relapsed/Refractory Multiple Myeloma, Chicago, 7 pages (2019).
Phipps, C., et al., "Daratumumab and its potential in the treatment of multiple myeloma: overview of the preclinical and clinical development," Ther. Adv. Hematol., vol. 6; No. 3; 120-127 (2015).
Pivot, X. et al., "Patients' preferences for subcutaneous trastuzumab versus conventional intravenous infusion for the adjuvant treatment of HER2-positive early breast cancer: final analysis of 488 patients in the international, randomized, two-cohort PrefHer study," Annals of Oncology, vol. 25; 1979-1987 (2014).
Poosarla, V.G. et al., "Computational De Novo Design of Antibodies Binding to a Peptide With High Affinity," Biotechnology & Bioengineering, vol. 114; No. 6; 1331-1342 (2017).
Rader, C. et al., "A phage display approach for rapid antibody humanization: Designed combinatorial V gene libraries," Proc. Natl. Acad. Sci, vol. 95; 8910-8915 (1998).
Rosengren, S. et al., Clinical Immunogenicity of rHuPH20, a Hyaluronidase Enabling Subcutaneous Drug Administration, The AAPS Journal, vol. 17; No. 5; 1144-1156 (2015).
Ruberg, E-M. and FrieB, W., "Sensibel und stressanfallig," Pharmazeutische Zeitung, 156 JG, AUSG. 50; 15 pages (2011).
Rudikoff, S. et al., "Single amino acid substitution altering antigen-binding specificity," Proc. Natl. Acad., col. 79; 1979-1983 (1982).
Ryan, et al., "Potentiation of Anti-Myeloma Activity of Daratumumab with Combination of Cyclophosphamide, Lenalidomide or Bortezomib via a Tumor Secretory Response That Greatly Augments Macrophage-Induced ADCP," Annual Meeting at the Haematology Association of Ireland, Oct. 15, 2016; 20 pages.
Sondergeld, P. et al., "Monoclonal Antibodies in Myeloma," Clinical Advances in Hematology & Oncology, vol. 13; Issue 9; 599-609 (2015).
Wang, W. et al., "Antibody Structure, Instability, and Formulation," Journal of Pharmaceutical Sciences, vol. 96; 1-26 (2007).

(56) References Cited

OTHER PUBLICATIONS

Warne, N.W., "Development of high concentration protein biopharmaceuticals: The use of platform approaches in formulation development," European Journal of Pharmaceutics and Biopharmaceutics, vol. 78; 208-212 (2011).
WHO Drug Information, International Nonproprietary Names for Pharmaceutical Substances (INN), Proposed INN: List 101, vol. 23; No. 2; 64 pages (2009).
WHO Drug Information, International Nonproprietary Names for Pharmaceutical Substances (INN), Recommended INN: List 63, 40 pages (2010).
Wunderlich, M. et al., "AML cells are differentially sensitive to chemotherapy treatment in a human xenograft model," eBlood, vol. 121; No. 12; e90-e97 (2013).
Notice of Opposition Dated Oct. 20, 2021 by Opponent Konig Szynka Tilmann von Renesse, filed in European Patent No. 3 370 770 B1.
Notice of Opposition Dated Oct. 19, 2021 by Opponent Patent Boutique LLP, filed in European Patent No. 3 370 770 B1.
Notice of Opposition Dated Oct. 20, 2021 by Opponent Dr. Markus Breuer, filed in European Patent No. 3 370 770 B1.
Final Office Action for U.S. Appl. No. 15/798,670 dated Aug. 10, 2021.
Non-Final Office Action for U.S. Appl. No. 16/656,569 dated Aug. 26, 2021.
Non-Final Office Action for U.S. Appl. No. 16/312,133 dated Oct. 28, 2021.
ASH Clinical News, "Is Daratumumab Plus Lenalidomide-Dexamethasone a New Standard for Transplant-Ineligible Myeloma," Dated Jan. 1, 2019, Retrieved from Internet URL: https://www.ashclinicalnews.org/on-location/ash-annual-meeting/daratumumab-plus-lenalidomid; Retrieved Oct. 28, 2022 (2 pages).
Avet-Loiseau. H. et al., "Evaluation of Minimal Residual Disease (MRD) in Relapsed/Refractory Multiple Myeloma (RRMM) Patients Treated with Daratumumab in Combination with Lenalidomide Plus Dexamethasone or Bortezomib Plus Dexamethasone," Blood, vol. 128; No. 22; 246; 7 pages (2016).
Bauer, Fromming, Fuhrer, "Lehrbuch der Pharmazeutischen Technologie"8th Edition, Wissenschaftliche Verlagsgesellschaft Stuttgart, Chapter 9; 23 8-243 (2006).
Chaulagain, C.P. et al., "Pre-clinical translational studies of daratumumab in patients with myeloma or AL amyloidosis undergoing autologous hematopoietic stem cell transplantation (SCT)," Journal of Clinical Oncology, May 20, 2015, vol. 33, No. 15 suppl., pp. 8587-8587.
CureSearch for Children's Cancer, "Relapse of Recurrence," Retneved from Internet URL: https://curesearch.org/Relapse-or-Recurrence, 3 pages; Retrieved on Oct. 27, 2022.
Darzalex, Highlights and Prescribing Information, FDA Label, 32 pages (2018).
Dimopoulos, M.A. et al., "Daratumumab, Lenalidomide, and Dexamethasone for Multiple Myeloma," The New England Journal of Medicine, vol. 375; No. 14; 1319-1331 (2016); Suppl. Material: the protocol; total pages 111 (2016).
Drach, J. et al., "Retinoic Acid-induced Expression of CD38 Antigen in Myeloid Cells is Mediated through Retinoic Acid Receptor-$\alpha^1$," Cancer Research, vol. 54; 1746-1752 (1994).
Durie, B.G.M. et al.. "International Uniform Response Criteria for Multiple Myeloma," Leukemia, vol. 20; 1467-1473 (2006).
Facon, T. et al., "Phase 3 Randomized Study of Daratumumab Plus Lenalidomide and Dexamethasone (D-Rd) Versus Lenalidomide and Dexamethasone (Rd) in Patients with Newly Diagnosed Multiple Myeloma (NDMM) Ineligible for Transplant (MAIA)," Blood, vol. 132 (Suppl 1); 8 Pages (2018).
Gay, F. and Palumbo, A., "Management of Older Patients with Multiple Myeloma," Blood Reviews, vol. 25; 65-73 (2011).
Knowles, S.P. et al., "Safety of recombinant human hyaluronidase PH20 for subcutaneous drug delivery," Expert Opinion on Drug Delivery, vol. 18; No. 11; 1673-1685 (2021).
Kyle, R.A. and Rajkumar, S.V., "Criteria for diagnosis, staging, risk stratification and response assessment of multiple myeloma," Leukemia, vol. 23; 3-9 (2009).
Kyle, R.A. et al.. "Clinical Course and Prognosis of Smoldering (Asymptomatic) Multiple Myeloma," The New England Journal of Medicine, vol. 356; 2582-2590 (2007).
Kyle, R.A. et al., "Review of 1027 Patients with Newly Diagnosed Multiple Myeloma," May Clinic Proc., vol. 78; 21-33 (2003).
Lefranc, M. et al., "IMGT unique numbering for immunoglobulin and T cell receptor variable domains and Ig superfamily V-like domains," Developmental & Comparative Immunology, vol. 27; 55-77 (2003).
Mahajan, S. et al., "The evolution of stem-cell transplantation in multiple myeloma," Therapeutic Advances in Hematology, vol. 9; No. 5; 123-133 (2018).
McCudden, C. et al., "Monitoring multiple myeloma patients treated with daratumumab: teasing out monoclonal antibody interference," Clin Chem Lab Med. Vol. 54; No. 6: 1095-1104 (2016).
Palumbo, A. et al., "International Myeloma Working Group guidelines for the management of multiple myeloma patients ineligible for standard high-dose chemotherapy with autologous stem cell transplantation," Leukemia, vol. 23; 1716-1730 (2009).
Palumbo, A. and Anderson, K., "Multiple Myeloma," Tire New England Journal of Medicine, vol. 364; 1046-1060 (2011).
Rajkumar. S.V. et al., "Consensus recommendations for the uniform reporting of clinical trials: Report of the International Myeloma Workshop Consensus Panel 1," Blood, vol. 117; No. 18; 4691-4695 (2011).
Taussig, D.C. et al., "Anti-CD38 antibody-mediated clearance of human repopulating cells masks the heterogeneity of leukemia-initiating cells." Blood, vol. 112; No. 3; 568-575 (2008).
Usmani, S.Z. et al., "Final anaivsis of the phase III non-inferiority COLUMBA study of subcutaneous versus intravenous daratumumab in patients with relapsed or refractory multiple myeloma," Haematologica, vol. 107; 2408-2417 (2022).
Wasserman, R.L., "Progress in Gammaglobulin Therapy for Immunodeficiency: From Subcutaneous to Intravenous Infusions and Back Again," J. Clin. Immunol., vol. 32 ;1153-1164 (2012).
Wu, et al., An Analysis of the Sequences of the Variable Regions of Bence Jones Proteins and Myeloma Light Chains and Their Implications for Antibody Complementarity, Journal of Experimental Medicine, 132: 211-250 (1970).
Yamamoto, H. et al., "A mammalian homolog of the zebrafish transmembrane protein 2 (TMEM2) is the long-sought-after cell-surface hyaluronidase," J. Biol. Chem., vol. 292; No. 18; 7304-7313 (2017).
Zadnikova, P. et al., "Tire Degradation of Hyaluronan in tire skin," Biomolecules, vol. 12; 251, 17 pages (2022).
International Preliminary Report on Patentability for International Application No. PCT/IB2020/051484, dated Sep. 2, 2021.
International Search Report and Written Opinion for International Application No. PCT/IB2020/051484, dated Jul. 2, 2020.
Opponent's submission by Dr. Markus Breuer dated Oct. 4, 2022 filed in European Patent No. 3 370 770 B1.
Non Final Office Action for U.S. Appl. No. 16/840,153 dated Aug. 16, 2022.
Notice of Allowance for U.S. Appl. No. 16/840,153 dated Dec. 21, 2022.
Non-Final Office Action for U.S. Appl. No. 17/005,039 dated Dec. 9, 2022.
Notice of Allowance for U.S. Appl. No. 16/741,542 dated Nov. 2, 2022.
Notice of Allowance for U.S. Appl. No. 16/312,133 dated Sep. 2, 2022.
Final Office Action for U.S. Appl. No. 16/830,585 dated Oct. 26, 2022.
Final Office Action for U.S. Appl. No. 16/830,763 dated Oct. 24, 2022.
Final Office Action for U.S. Appl. No. 16/830,810 dated Oct. 25, 2022.
Final Office Action for U.S. Appl. No. 16/830,909 dated Oct. 26, 2022.

(56) References Cited

OTHER PUBLICATIONS

Chung, C.H., "Managing Premedications and the Risk for Reactions to Infusional Monoclonal Antibody Therapy," The Oncologist, vol. 13; 725-732 (2008).
ClinicalTrials.gov. "History of Changes for Study: NCT02519452: A Study of Daratumumab With the Addition of Recombinant Human Hyaluronidase (rHuPH20) for the Treatment of Participants with Relapsed or Refractory Multiple Myeloma," U.S. National Library of Medicine, ClinicalTrials.gov Archive, Dec. 3, 2020 (12 pages).
ClinicalTrials.gov. "A Study of Daratumumab with tire Addition of Recombinant Human Hyaluronidase (rHuPH20) for the Treatment of Participants with Relapsed or Refractory Multiple Myeloma," Identifier: NCT02519452; First Received: Aug. 6, 2015 (5 pages).
Common Terminology Criteria for Adverse Events (CTCAE), Version 4.03, U.S. Department of Health and Human Services, 4 pages (2010).
Complete Specification for Indian Application No. 4718/CHENP/2007; published on Jan. 11, 2008 (225 Pages).
Consolidated list of references from Opposition in parent patent EP No. 3370770, 4 pages; Feb. 24, 2022,.
Doessegger, L. and Banholzer, M.L., "Clinical development methodology for infusion-related reactions with monoclonal antibodies." Clinical & Translational Immunology, vol. 4; e39; 9 pages (2015).
European Medicines Agency, Summary of Product Characteristics for Rituximab; 153 pages; Oct. 30, 2009, https://www.ema.europa.eu/en/documents/product-information/mabthera-epar-product-information_en.pdf.
European Union Clinical Trials Register Clinical Trials Register, EudraCT No. 2014-002272-88; Title: "A Phase 3, Randomized, Controlled, Open-label Study of VELCADE (Bortezomlb) Melphalan-Prednisone (VMP) Compared to Daratumumab In Combination with VMP (D-VMP), In Subjects with Previously Untreated Multiple Myeloma who are Ineligible for High-dose Therapy," 6 pages (2015).
European Union Clinical Trials Register Clinical Trials Register, EudraCT No. 2014-002273-11; Title: "A Phase 3 Study Comparing Daratumumab, Lenalidomide, and Dexamethasone (DRd) vs Lenalidomide and Dexamethasone (Rd) In Subjects with Previously Untreated Multiple Myeloma who are Ineligible for High Dose Therapy," 7 pages (2015).
European Union Clinical Trials Register Clinical Trials Register, EudraCT No. 2013-005525-23; Title: "Phase 3 Study Comparing Daratumumab, Lenalidomide, and Dexamethasone (DRd) vs Lenalidomide and Dexamethasone (Rd) in Subjects with Relapsed or Refractory Multiple Myeloma," 7 pages (2014).
European Union Clinical Trials Register Clinical Trials Register, EudraCT No. 2014-000255-85; Title: "Phase 3 Study Comparing Daratumumab, Bortezomlb and Dexamethasone (DVd) vs Bortezomib and Dexamethasone (Vd) In Subjects With Relapsed or Refractory Multiple Myeloma," 6 pages (2014).
Highlights of Prescribing Information, Rituxan, 53 pages (1997).
Highlights of Prescribing Information, Rituxan (rituximab) injection, 44 pages (1997).
Janssen Submits Marketing Authorisation Application for Daratumumab for European Patients with Heavily Pre-treated Multiple Myeloma, Janssen-Cilag International NV; 7 pages (2015).
Jolies, S., "Hyaluronidase facilitated subcutaneous immunoglobulin in primary immunodeficiency," ImmunoTargets and Therapy, vol. 2; 125-133 (2013).
Kim, H. et al., "Overview of methods for comparing the efficacies of drugs in the absence of head-to-head clinical trial data," Br. J. Clin. Pharmacol., vol. 77; No. 1; 116-121 (2013).
Laubach, J.P et al., "The challenge of cross-trial comparisons using limited data," haematologica, vol. 99;e145; 2 pages (2014).
Lokhorst, H.M. et al., "Targeting CD38 with Daratumumab Monotherapy in Multiple Myeloma," The New England Journal of Medicine, vol. 373; 1207-1219 (2015); Supplemental Appendix.
Lonial, S. et al., "Phase II study of daratumumab (DARA) monotherapy in patients with greater than or equal to 3 lines of prior therapy or double refractory multiple myeloma (MM): 54767414MMY2002 (Sirius)," Journal of Clinical Oncology, vol. 33; No. 18 Suppl (2015).
Maury, M. et al., "Spray-drying of proteins: effects of sorbitol and trehalose on aggregation and FT-IR amide I spectrum of an immunoglobulin G," European Journal of Pharmaceutics and Biopharmaceutics, vol. 59; 251-261 (2005).
Moreau, P. et al., "Rituximab in CD20 positive multiple myeloma," Leukemia, vol. 21; 835-836 (2007).
Moreau, P. et al., "Practical Considerations for the Use of Daratumumab, a Novel CD38 Monoclonal Antibody, in Myeloma," Drugs, vol. 76; 853-867 (2016).
Patent Assignment Cover Sheet for U.S. Appl. No. 16/380,994, 6 pages; Sep. 11, 2019.
Pre-Grant Notice of Opposition filed in Indian Application No. 201617029109, by Indian Pharmaceutical Alliance, dated Feb. 24, 2022 (30 pages).
Preliminary Opinion of the Opposition Division, as cited in EP Opposition against EP Patent No. 3370770; 13 pages; dated Aug. 8, 2022.
Raj, T.A. et al., "Vincristine sulfate liposomal injection for acute lymphoblastic leukemia," International Journal of Nanomedicine, vol. 8; 4361-4369 (2013).
Rituxan (tituximab), Highlights of prescribing information. Rituxan (IV administered Rituximab; 35 pages (1997).
Solal-Deligny, P., "Rituximab by subcutaneous route," Expert Rev. Hematol., vol. 8; No. 2; 147-153 (2015).
Strickley, R.G. and Lambert, W.J., "A review of formulations of commercially available antibodies," Journal of Pharmaceutical Sciences, vol. 110; 2590-2608 (2021).
Zagouri, F. et al., "Emerging antibodies for the treatment of multiple myeloma," Expert Opinion on Emerging Drugs, vol. 21; No. 2; 225-237 (2016).
Zojer, N. et al., "Rituximab treatment provides No. clinical benefit in patients with pretreated advanced multiple myeloma," Leukemia & Lymphoma, vol. 47; No. 6; 1103-1109 (2006).
Declaration of Professor Adrian Llewellyn Harris, in Opposition Proceedings against European Patent No. 3370770, 109 pages (Dated Dec. 20, 2022).
Declaration of Dr. Richard Senderoff, in Opposition Proceedings against European Patent No. 3370770, 28 pages (Dated Dec. 20, 2022).
Declaration of Professor Dr. Andreas Zimmer, in Opposition Proceedings against European Patent No. 3370770, 5 pages (Dated Jan. 9, 2023).
Second Declaration of Professor Christian Jackisch, in Opposition Proceedings against European Patent No. 3370770, 8 pages (Dated Jan. 6, 2023).
Notice of Opposition Dated Dec. 22, 2022 by Opponent Dr. Hans Ulrich Domes, filed in European Patent No. 3 827 845 B1; 44 Pages.
Notice of Opposition Dated Dec. 27, 2022 by Opponent Konig Szynka Tilmann von Renesse, filed in European Patent No. 3 827 845 B1; 49 Pages.
Notice of Opposition Dated Dec. 28, 2022 by Opponent Michalski Huttermann & Partner, filed in European Patent No. 3 827 845 B1; 44 Pages.
Notice of Opposition dated Dec. 29, 2022 by Opponent Patent Boutique LLP, filed in European Patent No. 3 827 845 B1; 49 Pages.
Notice of Opposition Dated Dec. 21, 2022 by Opponent Xbrane Biopharma AB, filed in European Patent No. 3 827 845 B1; 68 Pages.
Opponent's submission by Konig Szynka Tilmann von Renesse dated Jan. 11, 2023, filed in European Patent No. 3 370 770 B1; 27 Pages.
Opponent's submission by Dr. Markus Breuer dated Jan. 13, 2023, filed in European Patent No. 3 370 770 B1; 11 Pages.
Opponent's submission by Patent Boutique LLP dated Jan. 12, 2023, filed in European Patent No. 3 370 770 B1; 56 Pages.
Reply to Notice of Opposition, filed in European Patent No. 3 370 770 B1, entitled: "Subcutaneous Formulations of Anti-CD38 Antibodies And Their Uses," 19 pages, dated Jan. 13, 2023.

\* cited by examiner

SEQUENCE LISTING

<160> NUMBER OF SEQ ID NOS: 21

<210> SEQ ID NO 1
<211> LENGTH: 300
<212> TYPE: PRT
<213> ORGANISM: Homo sapiens
<220> FEATURE:
<223> OTHER INFORMATION: Human CD38 aa

<400> SEQUENCE: 1

```
Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
            20                  25                  30

Leu Ile Leu Val Val Val Leu Ala Val Val Val Pro Arg Trp Arg Gln
        35                  40                  45

Gln Trp Ser Gly Pro Gly Thr Thr Lys Arg Phe Pro Glu Thr Val Leu
    50                  55                  60

Ala Arg Cys Val Lys Tyr Thr Glu Ile His Pro Glu Met Arg His Val
65                  70                  75                  80

Asp Cys Gln Ser Val Trp Asp Ala Phe Lys Gly Ala Phe Ile Ser Lys
                85                  90                  95

His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile
        115                 120                 125

Lys Asp Leu Ala His Gln Phe Thr Gln Val Gln Arg Asp Met Phe Thr
    130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Ala Ala Cys Asp Val Val His Val Met Leu
        195                 200                 205

Asn Gly Ser Arg Ser Lys Ile Phe Asp Lys Asn Ser Thr Phe Gly Ser
    210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
```

```
                    245                 250                 255
Pro Thr Ile Lys Glu Leu Glu Ser Ile Ile Ser Lys Arg Asn Ile Gln
                260                 265                 270

Phe Ser Cys Lys Asn Ile Tyr Arg Pro Asp Lys Phe Leu Gln Cys Val
            275                 280                 285

Lys Asn Pro Glu Asp Ser Ser Cys Thr Ser Glu Ile
290                 295                 300

<210> SEQ ID NO 2
<211> LENGTH: 14
<212> TYPE: PRT
<213> ORGANISM: Homo Sapiens
<220> FEATURE:
<223> OTHER INFORMATION: Human CD38 region 1 aa

<400> SEQUENCE: 2

Ser Lys Arg Asn Ile Gln Phe Ser Cys Lys Asn Ile Tyr Arg
1               5                   10

<210> SEQ ID NO 3
<211> LENGTH: 14
<212> TYPE: PRT
<213> ORGANISM: Homo Sapiens
<220> FEATURE:
<223> OTHER INFORMATION: Human CD38 region 2 aa

<400> SEQUENCE: 3

Glu Lys Val Gln Thr Leu Glu Ala Trp Val Ile His Gly Gly
1               5                   10

<210> SEQ ID NO 4
<211> LENGTH: 122
<212> TYPE: PRT
<213> ORGANISM: Artificial
<220> FEATURE:
<223> OTHER INFORMATION: Daratumumab VH

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Asp Lys Ile Leu Trp Phe Gly Glu Pro Val Phe Asp Tyr Trp
            100                 105                 110

Gly Gln Gly Thr Leu Val Thr Val Ser Ser
        115                 120

<210> SEQ ID NO 5
<211> LENGTH: 107
<212> TYPE: PRT
<213> ORGANISM: Artificial
<220> FEATURE:
<223> OTHER INFORMATION: Daratumumab VL
```

-continued

<400> SEQUENCE: 5

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105

<210> SEQ ID NO 6
<211> LENGTH: 5
<212> TYPE: PRT
<213> ORGANISM: Artificial
<220> FEATURE:
<223> OTHER INFORMATION: Daratumumab HCDR1

<400> SEQUENCE: 6

Ser Phe Ala Met Ser
1               5

<210> SEQ ID NO 7
<211> LENGTH: 17
<212> TYPE: PRT
<213> ORGANISM: Artificial
<220> FEATURE:
<223> OTHER INFORMATION: Daratumumab HCDR2

<400> SEQUENCE: 7

Ala Ile Ser Gly Ser Gly Gly Thr Tyr Tyr Ala Asp Ser Val Lys
1               5                   10                  15

Gly

<210> SEQ ID NO 8
<211> LENGTH: 13
<212> TYPE: PRT
<213> ORGANISM: Artificial
<220> FEATURE:
<223> OTHER INFORMATION: Daratumumab HCDR3

<400> SEQUENCE: 8

Asp Lys Ile Leu Trp Phe Gly Glu Pro Val Phe Asp Tyr
1               5                   10

<210> SEQ ID NO 9
<211> LENGTH: 11
<212> TYPE: PRT
<213> ORGANISM: Artificial
<220> FEATURE:
<223> OTHER INFORMATION: Daratumumab LCDR1

<400> SEQUENCE: 9

Arg Ala Ser Gln Ser Val Ser Ser Tyr Leu Ala
1               5                   10

<210> SEQ ID NO 10

```
<211> LENGTH: 7
<212> TYPE: PRT
<213> ORGANISM: Artificial
<220> FEATURE:
<223> OTHER INFORMATION: Daratumumab LCDR2

<400> SEQUENCE: 10

Asp Ala Ser Asn Arg Ala Thr
1               5

<210> SEQ ID NO 11
<211> LENGTH: 10
<212> TYPE: PRT
<213> ORGANISM: Artificial
<220> FEATURE:
<223> OTHER INFORMATION: Daratumumab LCDR3

<400> SEQUENCE: 11

Gln Gln Arg Ser Asn Trp Pro Pro Thr Phe
1               5                   10

<210> SEQ ID NO 12
<211> LENGTH: 452
<212> TYPE: PRT
<213> ORGANISM: Artificial
<220> FEATURE:
<223> OTHER INFORMATION: Daratumumab HC

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Asp Lys Ile Leu Trp Phe Gly Glu Pro Val Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240
```

```
Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 13
<211> LENGTH: 214
<212> TYPE: PRT
<213> ORGANISM: Artificial
<220> FEATURE:
<223> OTHER INFORMATION: Daratumumab LC

<400> SEQUENCE: 13

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 14
<211> LENGTH: 122
<212> TYPE: PRT
<213> ORGANISM: Artificial
<220> FEATURE:
<223> OTHER INFORMATION: mAb003 VH

<400> SEQUENCE: 14

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Phe Ser Trp Val Arg Gln Ala Pro Gly Gln Gly Leu Glu Trp Met
        35                  40                  45

Gly Arg Val Ile Pro Phe Leu Gly Ile Ala Asn Ser Ala Gln Lys Phe
    50                  55                  60

Gln Gly Arg Val Thr Ile Thr Ala Asp Lys Ser Thr Ser Thr Ala Tyr
65                  70                  75                  80

Met Asp Leu Ser Ser Leu Arg Ser Glu Asp Thr Ala Val Tyr Tyr Cys
                85                  90                  95

Ala Arg Asp Asp Ile Ala Ala Leu Gly Pro Phe Asp Tyr Trp Gly Gln
            100                 105                 110

Gly Thr Leu Val Thr Val Ser Ser Ala Ser
        115                 120

<210> SEQ ID NO 15
<211> LENGTH: 107
<212> TYPE: PRT
<213> ORGANISM: Artificial
<220> FEATURE:
<223> OTHER INFORMATION: mAb003 VL

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                85                  90                  95

Thr Phe Gly Gln Gly Thr Lys Val Glu Ile Lys
            100                 105

```
<210> SEQ ID NO 16
<211> LENGTH: 122
<212> TYPE: PRT
<213> ORGANISM: Artificial
<220> FEATURE:
<223> OTHER INFORMATION: mAb024 VH

<400> SEQUENCE: 16

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45

Gly Ile Ile Tyr Pro His Asp Ser Asp Ala Arg Tyr Ser Pro Ser Phe
    50                  55                  60

Gln Gly Gln Val Thr Phe Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Val Gly Trp Gly Ser Arg Tyr Trp Tyr Phe Asp Leu Trp
            100                 105                 110

Gly Arg Gly Thr Leu Val Thr Val Ser Ser
        115                 120

<210> SEQ ID NO 17
<211> LENGTH: 107
<212> TYPE: PRT
<213> ORGANISM: Artificial
<220> FEATURE:
<223> OTHER INFORMATION: mAb024 VL

<400> SEQUENCE: 17

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Gly Leu Leu Ile
        35                  40                  45

Tyr Asp Ala Ser Asn Arg Ala Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 18
<211> LENGTH: 120
<212> TYPE: PRT
<213> ORGANISM: Artificial
<220> FEATURE:
<223> OTHER INFORMATION: MOR-202 VH

<400> SEQUENCE: 18

Gln Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
            20                  25                  30

Tyr Met Asn Trp Val Arg Gln Ala Pro Gly Lys Gly Leu Glu Trp Val
            35                  40                  45

Ser Gly Ile Ser Gly Asp Pro Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Pro Leu Val Tyr Thr Gly Phe Ala Tyr Trp Gly Gln
            100                 105                 110

Gly Thr Leu Val Thr Val Ser Ser
        115                 120

<210> SEQ ID NO 19
<211> LENGTH: 109
<212> TYPE: PRT
<213> ORGANISM: Artificial
<220> FEATURE:
<223> OTHER INFORMATION: MOR-202 VL

<400> SEQUENCE: 19

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Arg His Tyr Tyr Val
            20                  25                  30

Tyr Trp Tyr Gln Gln Lys Pro Gly Gln Ala Pro Val Leu Val Ile Tyr
            35                  40                  45

Gly Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Thr Gly Gly Ala Ser Leu
                85                  90                  95

Val Phe Gly Gly Gly Thr Lys Leu Thr Val Leu Gly Gln
            100                 105

<210> SEQ ID NO 20
<211> LENGTH: 120
<212> TYPE: PRT
<213> ORGANISM: Artificial Sequence
<220> FEATURE:
<223> OTHER INFORMATION: Isatuximab VH

<400> SEQUENCE: 20

Gln Val Gln Leu Val Gln Ser Gly Ala Glu Val Ala Lys Pro Gly Thr
1               5                   10                  15

Ser Val Lys Leu Ser Cys Lys Ala Ser Gly Tyr Thr Phe Thr Asp Tyr
            20                  25                  30

Trp Met Gln Trp Val Lys Gln Arg Pro Gly Gln Gly Leu Glu Trp Ile
            35                  40                  45

Gly Thr Ile Tyr Pro Gly Asp Gly Asp Thr Gly Tyr Ala Gln Lys Phe
    50                  55                  60

Gln Gly Lys Ala Thr Leu Thr Ala Asp Lys Ser Ser Lys Thr Val Tyr
65                  70                  75                  80

Met His Leu Ser Ser Leu Ala Ser Glu Asp Ser Ala Val Tyr Tyr Cys
                85                  90                  95
```

```
Ala Arg Gly Asp Tyr Tyr Gly Ser Asn Ser Leu Asp Tyr Trp Gly Gln
            100                 105                 110

Gly Thr Ser Val Thr Val Ser Ser
        115             120

<210> SEQ ID NO 21
<211> LENGTH: 107
<212> TYPE: PRT
<213> ORGANISM: Artificial
<220> FEATURE:
<223> OTHER INFORMATION: Isatuximab VL

<400> SEQUENCE: 21

Asp Ile Val Met Thr Gln Ser His Leu Ser Met Ser Thr Ser Leu Gly
1               5                   10                  15

Asp Pro Val Ser Ile Thr Cys Lys Ala Ser Gln Asp Val Ser Thr Val
            20                  25                  30

Val Ala Trp Tyr Gln Gln Lys Pro Gly Gln Ser Pro Arg Arg Leu Ile
        35                  40                  45

Tyr Ser Ala Ser Tyr Arg Tyr Ile Gly Val Pro Asp Arg Phe Thr Gly
50                  55                  60

Ser Gly Ala Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Pro Pro Tyr
            85                  90                  95

Thr Phe Gly Gly Gly Thr Lys Leu Glu Ile Lys
            100                 105
```

METHODS OF TREATING HIGH RISK MULTIPLE MYELOMA

RELATED APPLICATION

This application claims the benefit of U.S. Provisional Application No. 62/579,234, filed on Oct. 31, 2017, which is incorporated herein by reference in its entirety.

INCORPORATION BY REFERENCE OF MATERIAL IN ASCII TEXT FILE

This application incorporates by reference the Sequence Listing contained in the following ASCII text file being submitted concurrently herewith:
  a) File name: 01482024001_SEQUENCELISTING.txt; created Oct. 31, 2018, 20 KB in size.

FIELD

Disclosed are methods of treating a subject having high-risk multiple myeloma, methods of achieving negative minimal residual disease status in a subject having multiple myeloma, and methods of predicting a likelihood of, or decreasing a risk of, relapse and/or disease progression in a subject having multiple myeloma.

BACKGROUND

Multiple Myeloma (MM) is a B cell malignancy characterized by the latent accumulation of secretory plasma cells in bone marrow with a low proliferative index and an extended life span. The disease ultimately attacks bones and bone marrow, resulting in multiple tumors and lesions throughout the skeletal system. Approximately 1% of all cancers, and slightly more than 10% of all hematologic malignancies, can be attributed to MM. Incidence of MM increases in the aging population, with the median age at time of diagnosis being about 61 years.

Currently available therapies for MM include chemotherapy regimens, stem cell transplantation, THALOMID® (thalidomide), REVLIMID® (lenalidomide), POMA-LYST® (pomalidomide), VELCADE® (bortezomib), NINLARO® (ixazomib), KYPROLIS® (carfilzomib), FARA-DYK® (panobinostat), AREDIA® (pamidronate), ZOMETA® (zoledronic acid) and DARZALEX® (daratumumab). Current treatment protocols, which include a combination of chemotherapeutic agents such as vincristine, carmustine (BCNU), melphalan (Alkeran®), cyclophosphamide, doxorubicin (Adriamycin), and prednisone or dexamethasone, yield a complete remission rate of only about 5%, and median survival is approximately 36-48 months from the time of diagnosis. Recent advances using high dose chemotherapy followed by autologous bone marrow or peripheral blood mononuclear cell transplantation have increased the complete remission rate and remission duration. Nevertheless, overall survival has only been slightly prolonged, and no evidence for a cure has been obtained as yet. Ultimately, it is thought that all MM patients will relapse, even under maintenance therapy with interferon-alpha (IFN-α) alone or in combination with steroids.

Efficacy of the available drug treatment regimens for MM is limited by the low cell proliferation rate and development of drug resistance in up to 90% of patients. Chromosomal translocations, oncogene mutations, dysregulated signaling pathways such as anti-apoptotic and survival pathways, and bone marrow (BM) niche have been implicated to contribute to drug resistance in MM (for review, see Abdi et al., *Oncotarget* 4:2186-2207, 2013). The BM niche is implicated in proliferation, survival, differentiation, migration, and drug resistance of the malignant plasma cells (Manier et al., *J Biomed Biotechnol* 2012; published online 2012 Oct. 3, doi:_10.1155/_2012/_157496).

SUMMARY

Disclosed herein are methods of treating a subject having high-risk multiple myeloma, comprising administering to the subject a therapeutically effective amount of an anti-CD38 antibody, a corticosteroid, and a non-corticosteroid chemotherapeutic agent for a time sufficient to treat the high-risk multiple myeloma.

Methods of achieving negative minimal residual disease status in a subject having multiple myeloma are also provided, the methods comprising administering to the subject a therapeutically effective amount of an anti-CD38 antibody, a corticosteroid, and a non-corticosteroid chemotherapeutic agent for a time sufficient to achieve negative minimal residual disease status.

Also provided are methods of predicting a likelihood of relapse and/or disease progression in a subject having multiple myeloma comprising measuring a minimal residual disease status in the subject, wherein the subject has received a therapeutically effective amount of an anti-CD38 antibody, a corticosteroid, and a non-corticosteroid chemotherapeutic agent, wherein a positive minimal residual disease status is indicative of a likelihood of relapse and/or disease progression.

Further disclosed are methods of decreasing a risk of relapse and/or disease progression in a subject having multiple myeloma comprising administering to the subject a therapeutically effective amount of an anti-CD38 antibody, a corticosteroid, and a non-corticosteroid chemotherapeutic agent to achieve a negative minimal residual disease status, wherein the negative residual disease status decreases the risk of relapse and/or disease progression.

BRIEF DESCRIPTION OF THE DRAWINGS

The summary, as well as the following detailed description, is further understood when read in conjunction with the appended drawings. For the purpose of illustrating the disclosed methods, there are shown in the drawings exemplary embodiments of the methods; however, the methods are not limited to the specific embodiments disclosed. The drawings are not necessarily to scale, emphasis instead being placed upon illustrating embodiments. In the drawings.

DETAILED DESCRIPTION

Figure 1:
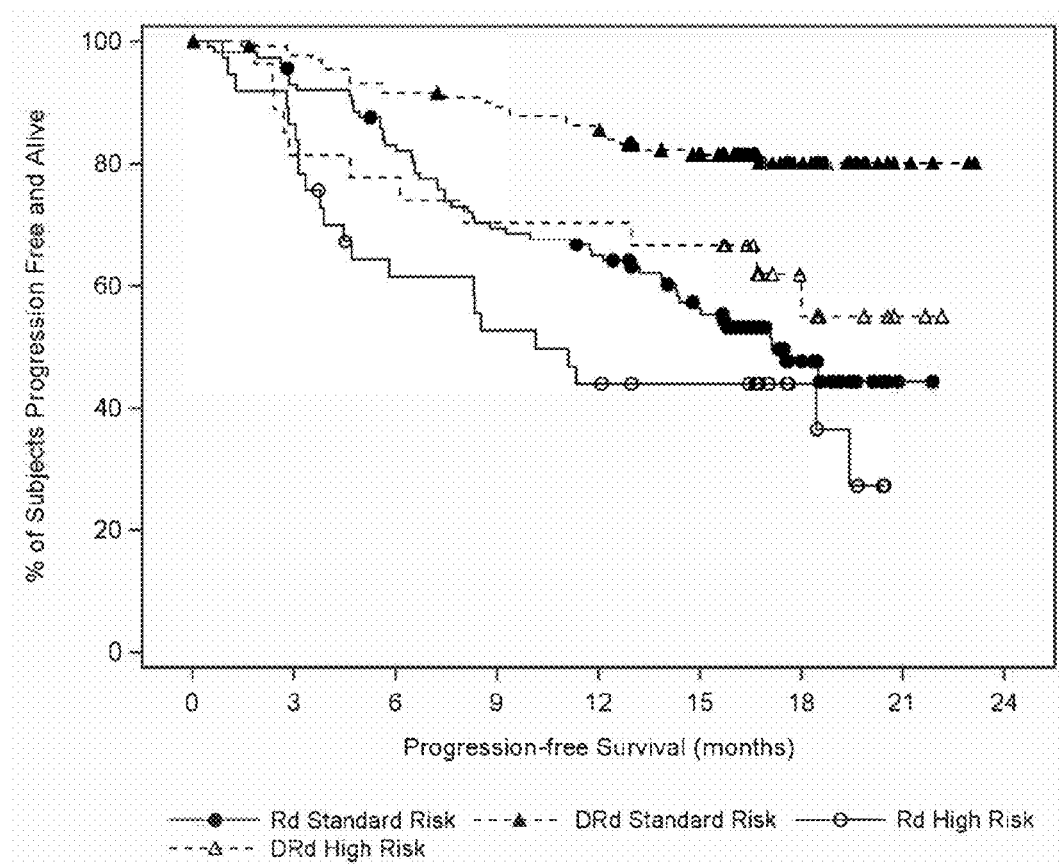
FIG. 1 illustrates a graph showing percentage (%) of multiple myeloma subjects progression free and alive by cytogenetic risk status in the POLLUX (MMY3003) trial. DRd: daratumumab in combination with lenalinomide and dexamethasone; Rd: lenalinomide and dexamethasone. High Risk: subject has at least one of the following chromosomal abnormalities: t(4;14)(p16;q32); t(14;16)(q32;q23); or del17p. Standard Risk: subject has documented absence of any of the aforementioned chromosomal abnormalities.

The disclosed methods may be understood more readily by reference to the following detailed description taken in connection with the accompanying figures, which form a part of this disclosure. It is to be understood that the disclosed methods are not limited to the specific methods described and/or shown herein, and that the terminology used herein is for the purpose of describing particular embodiments by way of example only and is not intended to be limiting of the claimed methods.

Unless specifically stated otherwise, any description as to a possible mechanism or mode of action or reason for improvement is meant to be illustrative only, and the disclosed methods are not to be constrained by the correctness or incorrectness of any such suggested mechanism or mode of action or reason for improvement.

Where a range of numerical values is recited or established herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value. It is not intended that the scope of the invention be limited to the specific values recited when defining a range. All ranges are inclusive and combinable.

When values are expressed as approximations, by use of the antecedent "about," it will be understood that the particular value forms another embodiment. Reference to a particular numerical value includes at least that particular value, unless the context clearly dictates otherwise.

It is to be appreciated that certain features of the disclosed methods which are, for clarity, described herein in the context of separate embodiments, may also be provided in combination in a single embodiment. Conversely, various features of the disclosed methods that are, for brevity, described in the context of a single embodiment, may also be provided separately or in any subcombination.

As used herein, the singular forms "a," "an," and "the" include the plural.

Various terms relating to aspects of the description are used throughout the specification and claims. Such terms are to be given their ordinary meaning in the art unless otherwise indicated. Other specifically defined terms are to be construed in a manner consistent with the definitions provided herein.

As used herein, "about" when used in reference to numerical ranges, cutoffs, or specific values is used to indicate that the recited values may vary by up to as much as 10% from the listed value. As many of the numerical values used herein are experimentally determined, it should be understood by those skilled in the art that such determinations can, and often times will, vary among different experiments. The values used herein should not be considered unduly limiting by virtue of this inherent variation. Thus, the term "about" is used to encompass variations of ±10% or less, variations of ±5% or less, variations of ±1% or less, variations of ±0.5% or less, or variations of ±0.1% or less from the specified value.

The term "comprising" is intended to include examples encompassed by the terms "consisting essentially of" and "consisting of"; similarly, the term "consisting essentially of" is intended to include examples encompassed by the term "consisting of."

"CD38" refers to the human CD38 protein (UniProtKB accession no. P28907) (synonyms: ADP-ribosyl cyclase 1, cADPr hydrolase 1, cyclic ADP-ribose hydrolase 1). Human CD38 has an amino acid sequence as shown in SEQ ID NO: 1. CD38 is a single pass type II transmembrane protein with amino acid residues 1-21 representing the cytosolic domain, amino acid residues 22-42 representing the transmembrane domain, and residues 43-300 representing the extracellular domain. Anti-CD38 antibodies are described, for example, in Int'l Pat. Pub. No. WO2008/037257, Int'l Pat. Pub. No. WO2008/047242 and Int'l Pat. Pub. No. WO2007/042309.

The term "antibody," and like terms is meant in a broad sense and includes immunoglobulin molecules including, monoclonal antibodies (such as murine, human, human-adapted, humanized, and chimeric monoclonal antibodies), antibody fragments, bispecific or multispecific antibodies, dimeric, tetrameric or multimeric antibodies, and single chain antibodies.

Immunoglobulins can be assigned to five major classes, namely IgA, IgD, IgE, IgG, and IgM, depending on the heavy chain constant domain amino acid sequence. IgA and IgG are further sub-classified as the isotypes IgA1, IgA2, IgG1, IgG2, IgG3, and IgG4. Antibody light chains of any vertebrate species can be assigned to one of two clearly distinct types, namely kappa (κ) and lambda (λ), based on the amino acid sequences of their constant domains.

"Antibody fragment" refers to a portion of an immunoglobulin molecule that retains the antigen binding properties of the parental full length antibody. Exemplary antibody fragments are heavy chain complementarity determining regions (HCDR) 1, 2, and/or 3, light chain complementarity determining regions (LCDR) 1, 2, and/or 3, a heavy chain variable region (VH), or a light chain variable region (VL). Antibody fragments include: a Fab fragment, a monovalent fragment consisting of the VL, VH, constant light (CL), and (constant heavy 1) CH1 domains; a F(ab)$_2$ fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; and a domain antibody (dAb) fragment (Ward et al., *Nature* 341:544-546, 1989), which consists of a VH domain or a VL domain. VH and VL domains can be engineered and linked together via a synthetic linker to form various types of single chain antibody designs where the VH/VL domains pair intramolecularly, or intermolecularly in those cases when the VH and VL domains are expressed by separate single chain antibody constructs, to form a monovalent antigen binding site, such as single chain Fv (scFv) or diabody; described for example in Int'l Pat. Pub. Nos. WO1998/44001, WO1988/01649, WO1994/13804, and WO1992/01047. These antibody fragments are obtained using techniques well known to those of skill in the art, and the fragments are screened for utility in the same manner as are full length antibodies.

The phrase "isolated antibody" refers to an antibody or antibody fragment that is substantially free of other antibodies having different antigenic specificities (e.g., an isolated anti-CD38 antibody is substantially free of antibodies that specifically bind antigens other than human CD38). An isolated anti-CD38 antibody, however, can have cross-reactivity to other antigens, such as orthologs of human CD38, such as *Macaca fascicularis* (cynomolgus) CD38. Moreover, an isolated antibody may be substantially free of other cellular material and/or chemicals.

An antibody variable region consists of a "framework" region interrupted by three "antigen binding sites." The antigen binding sites are defined using various terms: (i) Complementarity Determining Regions (CDRs), three in the VH (HCDR1, HCDR2, HCDR3), and three in the VL (LCDR1, LCDR2, LCDR3) are based on sequence variability (Wu and Kabat, JExpMed 132:211-50, 1970; Kabat et al. Sequences of Proteins of Immunological Interest, 5th Ed. Public Health Service, National Institutes of Health, Bethesda, Md., 1991); and (ii) "Hypervariable regions" ("HVR" or "HV"), three in the VH (H1, H2, H3) and three in the VL (L1, L2, L3) refer to the regions of the antibody variable domains which are hypervariable in structure as defined by Chothia and Lesk (Chothia and Lesk, Mot Blot 196:901-17, 1987). Other terms include "IMGT-CDRs" (Lefranc et al., Dev Comparat Immunol 27:55-77, 2003) and "Specificity Determining Residue Usage" (SDRU) (Almagro, Mot Recognit 17:132-43, 2004). The International ImMunoGeneTics (IMGT) database (www_imgt_org) provides a standardized numbering and definition of antigen-binding sites. The correspondence between CDRs, HVs and IMGT delineations is described in Lefranc et al., Dev Comparat Immunol 27:55-77, 2003.

"Framework" or "framework sequences" are the remaining sequences of a variable region other than those defined to be antigen binding sites. Because the antigen binding sites can be defined by various terms as described above, the exact amino acid sequence of a framework depends on how the antigen-binding site was defined.

"Humanized antibody" refers to an antibody in which the antigen binding sites are derived from non-human species and the framework regions are derived from human immunoglobulin sequences. Humanized antibodies may include substitutions in the framework regions so that the framework may not be an exact copy of expressed human immunoglobulin or germline gene sequences. If the antibody contains a constant region, the constant region is also derived from sequences of human origin. "Derived from," as used in the context of humanized antibodies, means that the region in question is at least 80% homologous in sequence to the corresponding region of the immunoglobulin from the species in which it is based.

"Human-adapted" antibodies or "human framework adapted (HFA)" antibodies refers to humanized antibodies adapted according to methods described in U.S. Pat. Publ. No. US2009/0118127. Human-adapted antibodies are humanized by selecting the acceptor human frameworks based on the maximum CDR and FR similarities, length compatibilities and sequence similarities of CDR1 and CDR2 loops and a portion of light chain CDR3 loops.

"Human antibody" refers to an antibody having heavy and light chain variable regions in which both the framework and the antigen binding sites are derived from sequences of human origin. If the antibody contains a constant region, the constant region also is derived from sequences of human origin. A human antibody comprises heavy or light chain variable regions that are "derived from" sequences of human origin if the variable regions of the antibody are obtained from a system that uses human germline immunoglobulin or rearranged immunoglobulin genes. Such systems include human immunoglobulin gene libraries displayed on phage, and transgenic non-human animals such as mice carrying human immunoglobulin loci as described herein. "Human antibody" may contain amino acid differences when compared to the human germline or rearranged immunoglobulin sequences due to, for example, naturally occurring somatic mutations or intentional introduction of substitutions in the framework or antigen binding sites. Typically, a "human antibody" is at least about 80%, 81%, 82%, 83%, 84%, 85%, 86%, 87%, 88%, 89%, 90%, 91%, 92%, 93%, 94%, 95%, 96%, 97%, 98%, 99%, or 100% identical in amino acid sequence to an amino acid sequence encoded by a human germline or rearranged immunoglobulin gene. In some cases, a "human antibody" may contain consensus framework sequences derived from human framework sequence analyses, for example as described in Knappik et al., *J Mol Biol* 296:57-86, 2000, or synthetic HCDR3 incorporated into human immunoglobulin gene libraries displayed on phage, as described in, for example, Shi et al., *J Mol Biol* 397:385-96, 2010 and Int'l Pat. Pub. No. WO2009/085462.

Antibodies in which antigen binding sites are derived from a non-human species are not included in the definition of "human antibody".

Isolated humanized antibodies may be synthetic. Human antibodies, while derived from human immunoglobulin sequences, may be generated using systems such as phage display incorporating synthetic CDRs and/or synthetic frameworks, or can be subjected to in vitro mutagenesis to improve antibody properties, resulting in antibodies that do not naturally exist within the human antibody germline repertoire in vivo.

"Recombinant antibody" includes all antibodies that are prepared, expressed, created, or isolated by recombinant means, such as: antibodies isolated from an animal (e.g., a mouse) that is transgenic or transchromosomal for human immunoglobulin genes or a hybridoma prepared therefrom (described further below); antibodies isolated from a host cell transformed to express the antibody; antibodies isolated from a recombinant, combinatorial antibody library; and antibodies prepared, expressed, created, or isolated by any other means that involve splicing of human immunoglobulin gene sequences to other DNA sequences, or antibodies that are generated in vitro using Fab arm exchange.

"Monoclonal antibody" refers to a preparation of antibody molecules of a single molecular composition. A monoclonal antibody composition displays a single binding specificity and affinity for a particular epitope, or in a case of a bispecific monoclonal antibody, a dual binding specificity to two distinct epitopes. Monoclonal antibody therefore refers to an antibody population with single amino acid composition in each heavy and each light chain, except for possible well-known alterations such as removal of C-terminal lysine from the antibody heavy chain. Monoclonal antibodies may have heterogeneous glycosylation within the antibody population. Monoclonal antibody may be monospecific or multispecific, or monovalent, bivalent or multivalent. A bispecific antibody is included in the term monoclonal antibody.

"Epitope" refers to a portion of an antigen to which an antibody specifically binds. Epitopes usually consist of chemically active (such as polar, non-polar, or hydrophobic) surface groupings of moieties such as amino acids or polysaccharide side chains and can have specific three-dimensional structural characteristics, as well as specific charge characteristics. An epitope can be composed of contiguous and/or discontiguous amino acids that form a conformational spatial unit. For a discontiguous epitope, amino acids from differing portions of the linear sequence of the antigen come in close proximity in 3-dimensional space through the folding of the protein molecule.

"Variant" refers to a polypeptide or a polynucleotide that differs from a reference polypeptide or a reference polynucleotide by one or more modifications for example, substitutions, insertions, or deletions.

"In combination with" means that two or more therapeutics can be administered to a subject together in a mixture, concurrently as single agents, or sequentially as single agents in any order.

"Treat," "treatment," and like terms refer to both therapeutic treatment and prophylactic or preventative measures, and includes reducing the severity and/or frequency of symptoms, eliminating symptoms and/or the underlying cause of the symptoms, reducing the frequency or likelihood of symptoms and/or their underlying cause, improving or remediating damage caused, directly or indirectly, by multiple myeloma. Treatment also includes prolonging survival as compared to the expected survival of a subject not receiving treatment. Subjects to be treated include those that have the condition or disorder as well as those prone to have the condition or disorder or those in which the condition or disorder is to be prevented.

"Therapeutically effective amount" refers to an amount of the disclosed combination therapy effective, at dosages and for periods of time necessary, to achieve a desired treatment. A therapeutically effective amount may vary according to factors such as the disease state, age, sex, and weight of the subject, and the ability of the combination therapy to elicit a desired response in the subject. Exemplary indicators of a therapeutically effect amount include, for example, improved well-being of the patient, reduction of a tumor burden, arrested or slowed growth of a tumor, and/or absence of metastasis of cancer cells to other locations in the body.

"Inhibit growth" (e.g., referring to cells, such as tumor cells) refers to a measurable decrease in in vitro or in vivo cell growth upon contact with the combination therapy when compared to the growth of the same cells in the absence of the combination therapy. Inhibition of growth of a cell in vitro or in vivo may be at least about 10%, about 20%, about 30%, about 40%, about 50%, about 60%, about 70%, about 80%, about 90%, about 99%, or about 100%. Inhibition of cell growth can occur by a variety of mechanisms, for example by antibody-mediated ADCC, ADCP and/or CDC, apoptosis, necrosis, or by inhibition of cell proliferation.

"Subject" includes any human or nonhuman animal. "Nonhuman animal" includes all vertebrates, e.g., mammals and non-mammals, such as nonhuman primates, sheep, dogs, cats, horses, cows, chickens, amphibians, reptiles, etc. The terms "subject" and "patient" can be used interchangeably herein.

The following abbreviations are used throughout the disclosure: bone marrow aspirates (BMA); complete response (CR); daratumumab, bortezomib, and dexamethasone (DVd); daratumumab, lenalinomide, and dexamethasone (DRd); International Myeloma Working Group (IMWG); International Staging System (ISS); minimal residual disease (MRD); multiple myeloma (MM); partial response (PR); progression-free survival (PFS); overall response rate (ORR); overall survival (OS); lenalinomide and dexamethasone (Rd); stringent complete response (sCR); time to disease progression (TTP); bortezomib and dexamethasone (Vd); very good partial response (VGPR); antibody-dependent cellular cytotoxicity (ADCC), antibody-dependent cellular phagocytosis (ADCP), bortezomib (Bort); complement-dependent cytotoxicity (CDC), complementarity determining region (CDR), constant light (CL), (constant heavy 1) CH1 domains, daratumumab (DARA); heavy chain CDR (HCDR), heavy chain variable region (VH), lenalidomide (LEN); light chain CDR (LCDR), light chain variable region (VL); patients (pts).

Methods of Treating a Subject Having High-Risk Multiple-Myeloma

Disclosed herein are methods of treating a subject having high-risk multiple myeloma, comprising administering to the subject a therapeutically effective amount of an anti-CD38 antibody, a corticosteroid, and a non-corticosteroid chemotherapeutic agent for a time sufficient to treat the high-risk multiple myeloma.

Any anti-CD38 antibody may be used in the disclosed methods. For example, the variable regions of the anti-CD38 antibodies may be obtained from existing anti-CD38 antibodies and optionally cloned as full length antibodies using standard methods. Exemplary antibody variable regions that bind CD38 that may be used are described in Int'l Pat. Pub.

Nos. WO2005/103083, WO2006/125640, WO2007/042309, WO2008/047242, WO2012/092612, WO2006/099875, and WO2011/154453A1.

The anti-CD38 antibody can bind to a region of human CD38 comprising SKRNIQFSCKNIYR (SEQ ID NO: 2) and a region of human CD38 comprising EKVQTLEAWVIHGG (SEQ ID NO: 3). An anti-CD38 antibody binds to a region of human CD38 comprising SEQ ID NO: 2 and a region of human CD38 comprising SEQ ID NO: 3 when the antibody binds at least 1, 2, 3, 4, 5, 6, 7, 8, 9, 10, 11, 12, 13, or 14 residues within SEQ ID NO: 2 and at least 1, 2, 3, 4, 5, 6, 7, 8, 9, 10, 11, 12, 13, or 14 residues within SEQ ID NO: 3. In some embodiments, the anti-CD38 antibody binds at least one amino acid in a region of human CD38 comprising SEQ ID NO: 2 and at least one amino acid in a region of human CD38 comprising SEQ ID NO: 3. In some embodiments, the anti-CD38 antibody binds at least two amino acids in a region of human CD38 comprising SEQ ID NO: 2 and at least two amino acids in a region of human CD38 comprising SEQ ID NO: 3. In some embodiments, the anti-CD38 antibody binds at least three amino acids in a region of human CD38 comprising SEQ ID NO: 2 and at least three amino acids in a region of human CD38 comprising SEQ ID NO: 3. Antibodies binding to a region of human CD38 comprising SEQ ID NO: 2 and a region of human CD38 comprising SEQ ID NO: 3 may be generated, for example, by immunizing mice with peptides having amino acid sequences comprising SEQ ID NOs: 2 and 3 using standard methods and as described herein, and characterizing the obtained antibodies for binding to the peptides using, for example, ELISA or mutagenesis studies.

An exemplary anti-CD38 antibody that binds to a region of human CD38 comprising SEQ ID NO: 2 and a region of human CD38 comprising SEQ ID NO: 3 is DARZALEX™ (daratumumab), which comprises:
- a heavy chain amino acid sequence of SEQ ID NO: 12 and light chain amino acid sequence of SEQ ID NO: 13;
- a heavy chain variable region (VH) of SEQ ID NO: 4 and a light chain variable region (VL) of SEQ ID NO: 5; and
- a heavy chain complementarity determining region (CDR) 1, a heavy chain CDR2, and a heavy chain CDR3 of SEQ ID NOs: 6, 7, and 8, respectively, and a light chain complementarity determining region (CDR) 1, a light chain CDR2, and a light chain CDR3 of SEQ ID NOs: 9, 10, and 11, respectively.

The anti-CD38 antibody can comprise a heavy chain CDR1 comprising the amino acid sequence of SEQ ID NO: 6, a heavy chain CDR2 comprising the amino acid sequence of SEQ ID NO: 7, a heavy chain CDR3 comprising the amino acid sequence of SEQ ID NO: 8, a light chain CDR1 comprising the amino acid sequence of SEQ ID NO: 9, a light chain CDR2 comprising the amino acid sequence of SEQ ID NO: 10, and a light chain CDR3 comprising the amino acid sequence of SEQ ID NO: 11. The anti-CD38 antibody can comprise a VH comprising an amino acid sequence that is 95%, 96%, 97%, 98%, 99%, or 100% identical to that of SEQ ID NO: 4 and a VL comprising an amino acid sequence that is 95%, 96%, 97%, 98%, 99%, or 100% identical to that of SEQ ID NO: 5. In some embodiments, the anti-CD38 antibody can comprise a VH comprising the amino acid sequence of SEQ ID NO: 4 and a VL comprising the amino acid sequence of SEQ ID NO: 5. The anti-CD38 antibody can comprise a heavy chain comprising the amino acid sequence of SEQ ID NO: 12 and a light chain comprising the amino acid sequence of SEQ ID NO: 13.

The anti-CD38 antibody can comprise a heavy chain CDR1, a heavy chain CDR2, and a heavy chain CDR3 of a VH comprising the amino acid sequence of SEQ ID NO: 14, and a light chain CDR1, a light chain CDR2, and a light chain CDR3 of a VL comprising the amino acid sequence of SEQ ID NO:15. The anti-CD38 antibody can comprise a VH comprising an amino acid sequence that is 95%, 96%, 97%, 98%, 99%, or 100% identical to that of SEQ ID NO: 15 and a VL comprising an amino acid sequence that is 95%, 96%, 97%, 98%, 99%, or 100% identical to that of SEQ ID NO: 15. In some embodiments, the anti-CD38 antibody can comprise a VH comprising the amino acid sequence of SEQ ID NO: 14 and a VL comprising the amino acid sequence of SEQ ID NOs:15. In some embodiments, for example, the anti-CD38 antibody can comprise mAb003 (described in U.S. Pat. No. 7,829,693, incorporated herein by reference).

The anti-CD38 antibody can comprise a heavy chain CDR1, a heavy chain CDR2, and a heavy chain CDR3 of a VH comprising the amino acid sequence of SEQ ID NO: 16, and a light chain CDR1, a light chain CDR2, and a light chain CDR3 of a VL comprising the amino acid sequence of SEQ ID NO: 17. The anti-CD38 antibody can comprise a VH comprising an amino acid sequence that is 95%, 96%, 97%, 98%, 99%, or 100% identical to that of SEQ ID NO: 16 and a VL comprising an amino acid sequence that is 95%, 96%, 97%, 98%, 99%, or 100% identical to that of SEQ ID NO: 17. In some embodiments, the anti-CD38 antibody can comprise a VH comprising the amino acid sequence of SEQ ID NO: 16 and a VL comprising the amino acid sequence of SEQ ID NO: 17. In some embodiments, for example, the anti-CD38 antibody can comprise mAb024 (described in U.S. Pat. No. 7,829,693, incorporated herein by reference).

The anti-CD38 antibody can comprise a heavy chain CDR1, a heavy chain CDR2, and a heavy chain CDR3 of a VH comprising the amino acid sequence of SEQ ID NO: 18, and a light chain CDR1, a light chain CDR2, and a light chain CDR3 of a VL comprising the amino acid sequence of SEQ ID NO: 19. The anti-CD38 antibody can comprise a VH comprising an amino acid sequence that is 95%, 96%, 97%, 98%, 99%, or 100% identical to that of SEQ ID NO: 18 and a VL comprising an amino acid sequence that is 95%, 96%, 97%, 98%, 99%, or 100% identical to that of SEQ ID NO: 19. In some embodiments, the anti-CD38 antibody can comprise a VH comprising the amino acid sequence of SEQ ID NO: 18 and a VL comprising the amino acid sequence of SEQ ID NO: 19. In some embodiments, for example, the anti-CD38 antibody can comprise MOR-202 (MOR-03087) (described in U.S. Pat. No. 8,088,896, incorporated herein by reference).

The anti-CD38 antibody can comprise a heavy chain CDR1, a heavy chain CDR2, and a heavy chain CDR3 of a VH comprising the amino acid sequence of SEQ ID NO: 20, and a light chain CDR1, a light chain CDR2, and a light chain CDR3 of a VL comprising the amino acid sequence of SEQ ID NO: 21. The anti-CD38 antibody can comprise a VH comprising an amino acid sequence that is 95%, 96%, 97%, 98%, 99%, or 100% identical to that of SEQ ID NO: 20 and a VL comprising an amino acid sequence that is 95%, 96%, 97%, 98%, 99%, or 100% identical to that of SEQ ID NO: 21. In some embodiments, the anti-CD38 antibody can comprise a VH comprising the amino acid sequence of SEQ ID NO: 20 and a VL comprising the amino acid sequence of SEQ ID NO: 21. In some embodiments, for example, the anti-CD38 antibody can comprise isatuximab (described in U.S. Pat. No. 8,153,765, incorporated herein by reference). In some aspects, the VH and the VL of isatuximab may be expressed as IgG1/κ.

Antibodies that are substantially identical to those disclosed herein may be used in the disclosed methods. The term "substantially identical" means that the antibody heavy chain or light chain amino acid sequences are identical, or have "insubstantial differences," compared to the antibody disclosed herein. Insubstantial differences are substitutions of 1, 2, 3, 4, 5, 6, 7, 8, 9, 10, 11, 12, 13, 14, or 15 amino acids in an antibody heavy chain or light chain that do not adversely affect antibody properties. Antibody sequences can be compared, for example, by pairwise alignments using the default settings of the AlignX module of Vector NTI v.9.0.0 (Invitrogen, Carlsbad, Calif.). The protein sequences of the disclosed antibodies can be used as a query sequence to perform a search against public or patent databases to, for example, identify related sequences. Exemplary programs used to perform such searches are the)(BLAST or BLASTP programs (www_ncbi_nlm/nih_gov), or the GenomeQuest™ (GenomeQuest, Westborough, Mass.) suite using the default settings. Antibodies that are substantially identical to the disclosed antibodies can be generated, for example, by making conservative modifications to the amino acid sequences of the disclosed antibodies. "Conservative modifications" refer to amino acid modifications that do not significantly affect or alter the binding characteristics of the antibody containing the amino acid sequences. Conservative modifications include amino acid substitutions, additions, and deletions. "Conservative substitutions" are those in which the amino acid is replaced with an amino acid residue having a similar side chain. The families of amino acid residues having similar side chains are well defined and include amino acids with acidic side chains (e.g., aspartic acid, glutamic acid), basic side chains (e.g., lysine, arginine, histidine), nonpolar side chains (e.g., alanine, valine, leucine, isoleucine, proline, phenylalanine, methionine), uncharged polar side chains (e.g., glycine, asparagine, glutamine, cysteine, serine, threonine, tyrosine, tryptophan), aromatic side chains (e.g., phenylalanine, tryptophan, histidine, tyrosine), aliphatic side chains (e.g., glycine, alanine, valine, leucine, isoleucine, serine, threonine), an amide (e.g., asparagine, glutamine), beta-branched side chains (e.g., threonine, valine, isoleucine), and sulfur-containing side chains (cysteine, methionine). Furthermore, any native residue in the polypeptide may also be substituted with alanine, as has been previously described for alanine scanning mutagenesis (MacLennan et al., (1988) Acta Physiol Scand Suppl 643:55-67; Sasaki et al., (1988) Adv Biophys 35:1-24). Exemplary substitutions that can be made to the anti-CD38 antibodies used in the disclosed methods include, for example, conservative substitutions with an amino acid having similar charge, hydrophobic, or stereochemical characteristics. Conservative substitutions may also be made to improve antibody properties, including stability or affinity, or to improve antibody effector functions. 1, 2, 3, 4, 5, 6, 7, 8, 9, 10, 11, 12, 13, 14, or 15 amino acid substitutions may be made, for example, to the heavy and/or the light chain of the anti-CD38 antibody. Furthermore, any native residue in the heavy and/or light chain may also be substituted with alanine, as has been previously described for alanine scanning mutagenesis (MacLennan et al., Acta Physiol Scand Suppl 643:55-67, 1998; Sasaki et al., Adv Biophys 35:1-24, 1998). Suitable amino acid substitutions may be determined by those skilled in the art at the time such substitutions are desired. Amino acid substitutions may be performed, for example, by PCR mutagenesis (as disclosed in U.S. Pat. No. 4,683,195). Libraries of variants may be generated using well-known methods; for example using random (NNK) or non-random codons (for example DVK codons) which encode 11 amino acids (Ala, Cys, Asp, Glu, Gly, Lys, Asn, Arg, Ser, Tyr, Trp) and screening the libraries for variants with desired properties. The generated variants may be tested for their binding to CD38 and their ability to induce ADCC using methods described herein.

The anti-CD38 antibody can be of the IgG1, IgG2, IgG3, or IgG4 isotype. In some embodiments, the anti-CD38 antibody is of the IgG1 isotype. In some embodiments, the anti-CD38 antibody is of the IgG2 isotype. In some embodiments, the anti-CD38 antibody is of the IgG3 isotype. In some embodiments, the anti-CD38 antibody is of the IgG4 isotype.

Anti-CD38 antibodies used in the disclosed methods may also be selected de novo from, for example, a phage display library, where the phage is engineered to express human immunoglobulins or portions thereof such as Fabs, single chain antibodies (scFv), or unpaired or paired antibody variable regions (Knappik et al., J Mol Biol 296:57-86, 2000; Krebs et al., J Immunol Meth 254:67-84, 2001; Vaughan et al., Nature Biotechnology 14:309-314, 1996; Sheets et al., PITAS (USA) 95:6157-6162, 1998; Hoogenboom and Winter, J Mol Biol 227:381, 1991; Marks et al., J Mol Biol 222:581, 1991). CD38 binding variable domains may be isolated, for example, from phage display libraries expressing antibody heavy and light chain variable regions as fusion proteins with bacteriophage pIX coat protein as described in Shi et al (2010) J Mol. Biol. 397:385-96 and Int'l Pat. Pub. No. WO2009/085462. The antibody libraries may be screened for binding to human CD38 extracellular domain and the obtained positive clones may be further characterized and the Fabs isolated from the clone lysates, and subsequently cloned as full length antibodies. Such phage display methods for isolating human antibodies are established in the art. See for example: U.S. Pat. Nos. 5,223,409; 5,403,484; 5,571,698; 5,427,908; 5,580,717; 5,969,108; 6,172,197; 5,885,793; 6,521,404; 6,544,731; 6,555,313; 6,582,915; and 6,593,081.

In some embodiments, the anti-CD38 antibody competes for binding to CD38 with a reference antibody comprising:
a) a heavy chain CDR1 comprising the amino acid sequence of SEQ ID NO: 6, a heavy chain CDR2 comprising the amino acid sequence of SEQ ID NO: 7, a heavy chain CDR3 comprising the amino acid sequence of SEQ ID NO: 8, a light chain CDR1 comprising the amino acid sequence of SEQ ID NO: 9, a light chain CDR2 comprising the amino acid sequence of SEQ ID NO: 10, and a light chain CDR3 comprising an amino acid sequence of SEQ ID NO: 11;
b) a VH comprising the amino acid sequence of SEQ ID NO: 4 and a VL comprising the amino acid sequence of SEQ ID NO: 5;
c) a heavy chain comprising the amino acid sequence of SEQ ID NO: 12 and a light chain comprising the amino acid sequence of SEQ ID NO: 13;
d) DARZALEX™ (daratumumab);
e) a heavy chain CDR1, a heavy chain CDR2, and a heavy chain CDR3 of a VH comprising the amino acid sequence of SEQ ID NO: 14, and a light chain CDR1, a light chain CDR2, and a light chain CDR3 of a VL comprising the amino acid sequence of SEQ ID NO: 15;
f) a VH comprising the amino acid sequence of SEQ ID NO: 14 and a VL comprising the amino acid sequence of SEQ ID NO: 15;
g) mAb003;
h) a heavy chain CDR1, a heavy chain CDR2, and a heavy chain CDR3 of a VH comprising the amino acid sequence of SEQ ID NO: 16, and a light chain CDR1, a light chain CDR2, and a light chain CDR3 of a VL comprising the amino acid sequence of SEQ ID NO: 17;
i) a VH comprising the amino acid sequence of SEQ ID NO: 16 and a VL comprising the amino acid sequence of SEQ ID NO: 17;
j) mAb024;
k) a heavy chain CDR1, a heavy chain CDR2, and a heavy chain CDR3 of a VH comprising the amino acid sequence of SEQ ID NO: 18, and a light chain CDR1, a light chain CDR2, and a light chain CDR3 of a VL comprising the amino acid sequence of SEQ ID NO: 19;
l) a VH comprising the amino acid sequence of SEQ ID NO: 18 and a VL comprising the amino acid sequence of SEQ ID NO: 19;
m) MOR-202 (MOR-03087);
n) a heavy chain CDR1, a heavy chain CDR2, and a heavy chain CDR3 of a VH comprising the amino acid sequence of SEQ ID NO: 20, and a light chain CDR1, a light chain CDR2, and a light chain CDR3 of a VL comprising the amino acid sequence of SEQ ID NO: 21;
o) a VH comprising the amino acid sequence of SEQ ID NO: 20 and a VL comprising the amino acid sequence of SEQ ID NO: 21;
p) isatuximab; or
q) any combination of a) to p).

Antibodies may be evaluated for their competition with a reference antibody (such as references antibodies a) to q) above) for binding to CD38 using well known in vitro methods. In an exemplary method, CHO cells recombinantly expressing CD38 may be incubated with unlabeled reference antibody for 15 min at 4° C., followed by incubation with an excess of fluorescently labeled test antibody for 45 min at 4° C. After washing in PBS/BSA, fluorescence may be measured by flow cytometry using standard methods. In another exemplary method, an extracellular portion of human CD38 may be coated on the surface of an ELISA plate. Excess unlabeled reference antibody may be added for about 15 minutes and subsequently biotinylated test antibodies may be added. After washes in PBS/Tween, binding of the test biotinylated antibody may be detected using horseradish peroxidase (HRP)-conjugated streptavidin and the signal detected using standard methods. In the competition assays, the reference antibody may be labeled and the test antibody may be unlabeled. The test antibody competes with the reference antibody when the reference antibody inhibits binding of the test antibody, or the test antibody inhibits binding of the reference antibody, by at least about 90%, 95%, or 100%. The epitope of the test antibody may further be defined, for example, by peptide mapping or hydrogen/deuterium protection assays using known methods, or by crystal structure determination.

The anti-CD38 antibody can induce killing of CD38-expressing cells by antibody-dependent cellular cytotoxicity (ADCC), antibody-dependent cellular phagocytosis (ADCP), complement-dependent cytotoxicity (CDC), or apoptosis. In some embodiments, the anti-CD38 antibody induces killing of CD38-expressing cells by ADCC. In some embodiments, the anti-CD38 antibody induces killing of CD38-expressing cells by ADCP. In some embodiments, the anti-CD38 antibody induces killing of CD38-expressing cells by CDC. In some embodiments, the anti-CD38 antibody induces killing of CD38-expressing cells by apoptosis. In some embodiments, the anti-CD38 antibody induces killing of CD38-expressing cells by any combination of ADCC, ADCP, CDC, and apoptosis.

"Antibody-dependent cellular cytotoxicity," "antibody-dependent cell-mediated cytotoxicity" or "ADCC" is a mechanism for inducing cell death that depends upon the interaction of antibody-coated target cells with effector cells possessing lytic activity, such as natural killer (NK) cells, monocytes, macrophages, and neutrophils via Fc gamma receptors (FcγR) expressed on effector cells. For example, NK cells express FcγRIIIa, whereas monocytes express FcγRI, FcγRII, and FcγRIIIa. Death of the antibody-coated target cell, such as CD38-expressing MM cell, occurs as a result of effector cell activity through the secretion of membrane pore-forming proteins and proteases. To assess ADCC activity of an anti-CD38 antibody, the antibody may be added to CD38-expressing cells in combination with immune effector cells, which may be activated by the antigen/antibody complexes resulting in cytolysis of the target cell. Cytolysis may be detected by the release of a label (e.g., radioactive substrates, fluorescent dyes, or natural intracellular proteins) from the lysed cells. Exemplary effector cells for such assays include peripheral blood mononuclear cells (PBMC) and NK cells. Multiple myeloma cell lines or primary MM cells that express CD38 may be used as target cells. In an exemplary assay, MM cell lines engineered to express luciferase are incubated with anti-CD38 antibodies. Freshly isolated PBMC effector cells are added at a target:effector cell ratio of 40:1. 4 hours after addition of PBMC, luciferin is added and the resulting bioluminescent signal emitted from surviving MM cells can be determined within 20 minutes using a luminometer (SpectraMax, Molecular Devices), and the percentage ADCC of MM cells can calculated using the formula: % ADCC=1−(mean bioluminescent signal in the absence of PBMCs/mean bioluminescent signal in the presence of PBMCs)×100%. Anti-CD38 antibodies used in the disclosed methods can induce ADCC by about 20%, 25%, 30%, 35%, 40%, 45%, 50%, 55%, 60%, 65%, 70%, 80%, 90%, or 100%.

"Complement-dependent cytotoxicity," or "CDC," refers to a mechanism for inducing cell death in which an Fc effector domain of a target-bound antibody binds and activates complement component C1q, which in turn activates the complement cascade leading to target cell death. Activation of complement may also result in deposition of complement components on the target cell surface that facilitate ADCC by binding complement receptors (e.g., CR3) on leukocytes. In an exemplary assay, primary BM-MNC cells isolated from a patient with a B-cell malignancy may be treated with an anti-CD38 antibody and complement derived from 10% pooled human serum for 1 hour at a concentration of 0.3-10 µg/ml, and the survival of primary CD38$^+$ MM cells may be determined by flow cytometry using techniques described in van der Veer et al., *Haematologica* 96:284-290, 2011; van der Veer et al., *Blood Cancer J* 1(10):e41, 2011. The percentage of MM cell lysis may be determined relative to an isotype control as described herein. Anti-CD38 antibodies used in the disclosed methods may induce CDC by about 20%, 25%, 30%, 35%, 40%, 45%, 50%, 55%, 60%, 65%, 70%, 75%, 80%, 85%, 90%, 95%, or 100%.

"Antibody-dependent cellular phagocytosis," or "ADCP," refers to a mechanism of elimination of antibody-coated target cells by internalization by phagocytic cells, such as macrophages or dendritic cells. ADCP may be evaluated by using monocyte-derived macrophages as effector cells and Daudi cells (ATCC® CCL-213™) or B cell leukemia or lymphoma tumor cells expressing CD38 as target cells engineered to express GFP or other labeled molecules. Effector:target cell ratio may be, for example, 4:1. Effector cells may be incubated with target cells for 4 hours with or without anti-CD38 antibody. After incubation, cells may be detached using accutase. Macrophages may be identified with anti-CD11b and anti-CD14 antibodies coupled to a fluorescent label, and percent phagocytosis may be determined based on % GFP fluorescence in the CD11$^+$CD14$^+$ macrophages using standard methods. Anti-CD38 antibodies used in the disclosed methods may induce ADCP by about 20%, 25%, 30%, 35%, 40%, 45%, 50%, 55%, 60%, 65%, 70%, 75%, 80%, 85%, 90%, 95% or 100%.

The Fc portion of the anti-CD38 antibody may mediate antibody effector functions such as antibody-dependent cell-mediated cytotoxicity (ADCC), antibody-dependent cellular phagocytosis (ADCP), or complement dependent cytotoxicity (CDC). Such functions may be mediated by binding of an Fc effector domain(s) to an Fc receptor on an immune cell with phagocytic or lytic activity, or by binding of an Fc effector domain(s) to components of the complement system. Typically, the effect(s) mediated by the Fc-binding cells or complement components result in inhibition and/or depletion of target cells, e.g., CD38-expressing cells. Human IgG isotypes IgG1, IgG2, IgG3, and IgG4 exhibit differential capacity for effector functions. ADCC may be mediated by IgG1 and IgG3, ADCP may be mediated by IgG1, IgG2, IgG3, and IgG4, and CDC may be mediated by IgG1 and IgG3.

ADCC elicited by the anti-CD38 antibodies may be enhanced by certain substitutions in the antibody Fc region. In some embodiments, the anti-CD38 antibodies comprise a substitution in the Fc region at amino acid position 256, 290, 298, 312, 356, 330, 333, 334, 360, 378, 430, or any combination thereof, wherein the residue numbering is according to the EU index (substitutions described in U.S. Pat. No. 6,737,056).

ADCC elicited by the anti-CD38 antibodies can also be enhanced by engineering an antibody oligosaccharide component. Human IgG1 or IgG3 are N-glycosylated at Asn297 with the majority of the glycans in the biantennary G0, G0F, G1, G1F, G2, or G2F forms. Antibodies produced by non-engineered CHO cells typically have a glycan fucose content (i.e. the amount of the fucose monosaccharide within the sugar chain at Asn297) of about at least 85%. The removal of the core fucose from the biantennary complex-type oligosaccharides attached to the Fc regions enhances the ADCC of antibodies via improved FcγRIIIa binding without altering antigen binding or CDC activity. Such modified antibodies can be achieved using different methods reported to lead to the successful expression of relatively high defucosylated antibodies bearing the biantennary complex-type of Fc oligosaccharides such as: control of culture osmolality (Konno et al., *Cytotechnology* 64:249-65, 2012); application of a variant CHO line Lec13 as the host cell line (Shields et al., *J Biol Chem* 277:26733-26740, 2002); application of a variant CHO line EB66 as the host cell line (Olivier et al., MAbs 2(4), 2010; Epub ahead of print; PMID:20562582); application of a rat hybridoma cell line YB2/0 as the host cell line (Shinkawa et al., *J Biol Chem* 278:3466-3473, 2003); introduction of small interfering RNA specifically against the α 1,6-fucosyltrasferase (FUT8) gene (Mori et al., *Biotechnol Bioeng* 88:901-908, 2004); or coexpression of β-1,4-N-acetylglucosaminyltransferase III and Golgi α-mannosidase II or a potent alpha-mannosidase I inhibitor, such as kifunensine (Ferrara et al., *J Biol Chem* 281:5032-5036, 2006, Ferrara et al., *Biotechnol Bioeng* 93:851-861, 2006; Xhou et al., *Biotechnol Bioeng* 99:652-65, 2008).

In some embodiments, the anti-CD38 antibody can have a biantennary glycan structure with fucose content between about 0% to about 15%, for example 15%, 14%, 13%, 12%, 11%, 10%, 9%, 8%, 7%, 6%, 5%, 4%, 3%, 2%, 1%, or 0%. In some embodiments, the anti-CD38 antibody can have a biantennary glycan structure with fucose content of about 50%, 45%, 40%, 35%, 30%, 25%, 20%, 15%, 14%, 13%, 12%, 11%, 10%, 9%, 8%, 7%, 6%, 5%, 4%, 3%, 2%, 1%, or 0%. Substitutions in the Fc region and reduced fucose content may enhance the ADCC activity of the anti-CD38 antibody.

Fucose content may be characterized and quantified by multiple methods, for example: 1) using MALDI-TOF of N-glycosidase F treated sample (e.g. complex, hybrid, and oligo- and high-mannose structures) as described in Int'l Pat. Pub. No. WO2008/0775462); 2) by enzymatic release of the Asn297 glycans with subsequent derivatization and detection/quantitation by HPLC (UPLC) with fluorescence detection and/or HPLC-MS (UPLC-MS); 3) intact protein analysis of the native or reduced mAb, with or without treatment of the Asn297 glycans with Endo S or other enzyme that cleaves between the first and the second GlcNAc monosaccharides, leaving the fucose attached to the first GlcNAc; 4) digestion of the antibody to constituent peptides by enzymatic digestion (e.g., trypsin or endopeptidase Lys-C), and subsequent separation, detection, and quantitation by HPLC-MS (UPLC-MS); and 5) separation of the antibody oligosaccharides from the antibody protein by specific enzymatic deglycosylation with PNGase F at Asn297. The oligosaccharides thus released can be labeled with a fluorophore, separated, and identified by various complementary techniques which allow: fine characterization of the glycan structures by matrix-assisted laser desorption ionization (MALDI) mass spectrometry by comparison of the experimental masses with the theoretical masses; determination of the degree of sialylation by ion exchange HPLC (GlycoSep C); separation and quantification of the oligosaccharide forms according to hydrophilicity criteria by normal-phase HPLC (GlycoSep N); and separation and quantification of the oligosaccharides by high performance capillary electrophoresis-laser induced fluorescence (HPCE-LIF).

The anti-CD38 antibody may bind human CD38 with a range of affinities ($K_D$). For example, the anti-CD38 antibody can bind CD38 with a $K_D$ equal to or less than about $1\times10^{-8}$ M, for example $5\times10^{-9}$ M, $1\times10^{-9}$M, $5\times10^{-10}$ M, $1\times10^{-10}$ M, $5\times10^{-11}$ M, $1\times10^{-11}$M, $5\times10^{-12}$M, $1\times10^{-12}$ M, $5\times10^{-13}$ M, $1\times10^{-13}$ M, $5\times10^{-14}$ M, $1\times10^{-14}$ M, $5\times10^{-15}$M, or any range or value therein, as determined by surface plasmon resonance or the Kinexa method, as practiced by those of skill in the art. In some embodiments, the anti-CD38 antibody can bind to CD38 with an affinity of equal to or less than $1\times10^{-8}$ M. In some embodiments, the anti-CD38 antibody can bind to CD38 with an affinity of equal to or less than $1\times10^{-9}$ M.

Antibody affinity can be measured using KinExA instrumentation, ELISA, or competitive binding assays known to those skilled in the art. The measured affinity of a particular antibody/CD38 interaction may vary if measured under different conditions (e.g., osmolarity, pH). Thus, measurements of affinity and other binding parameters (e.g., $K_D$, $K_{on}$, $K_{off}$) are typically made with standardized conditions and a standardized buffer. Those skilled in the art will appreciate that the internal error for affinity measurements for example using Biacore 3000 or ProteOn (measured as standard deviation, SD) may typically be within 5-33% for measurements within the typical limits of detection. Therefore, the term "about" in the context of $K_D$ reflects the typical standard deviation in the assay. For example, the typical SD for a $K_D$ of $1\times10^{-9}$M is up to $\pm 0.33\times10^{-9}$ M.

The dose of anti-CD38 antibody given to a subject having multiple myeloma is sufficient to alleviate or at least partially arrest the disease being treated ("therapeutically effective amount") and includes from about 0.005 mg to about 100 mg/kg, e.g. about 0.05 mg to about 30 mg/kg or about 5 mg to about 25 mg/kg, or about 4 mg/kg, about 8 mg/kg, about 16 mg/kg, or about 24 mg/kg. Suitable doses include, for example, about 1, 2, 3, 4, 5, 6, 7, 8, 9, 10, 15, 16, 17, 18, 19, 20, 21, 22, 23, 24, 25, 30, 40, 50, 60, 70, 80, 90, or 100 mg/kg.

A fixed unit dose of the anti-CD38 antibody may also be given, for example, 50, 100, 200, 500, or 1000 mg, or the dose may be based on the patient's surface area, e.g., 500, 400, 300, 250, 200, or 100 mg/m². Usually between 1 and 8 doses, (e.g., 1, 2, 3, 4, 5, 6, 7, or 8) may be administered to treat MM, but 9, 10, 11, 12, 13, 14, 15, 16, 17, 18, 19, 20, or more doses may be given.

The administration of the anti-CD38 antibody may be repeated after one day, two days, three days, four days, five days, six days, one week, two weeks, three weeks, one month, five weeks, six weeks, seven weeks, two months, three months, four months, five months, six months, or longer. Repeated courses of treatment are also possible, as is chronic administration. The repeated administration may be at the same dose or at a different dose. For example, the anti-CD38 antibody may be administered at 8 mg/kg or at 16 mg/kg at weekly intervals for 8 weeks, followed by administration at 8 mg/kg or at 16 mg/kg every two weeks for an additional 16 weeks, followed by administration at 8 mg/kg or at 16 mg/kg every four weeks by intravenous infusion.

The anti-CD38 antibodies may be administered by maintenance therapy, such as, e.g., once a week for a period of 6 months or more. For example, the anti-CD38 antibodies may be provided as a daily dosage in an amount of about 0.1 mg/kg to about 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90, or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19, or 20 after initiation of treatment, or any combination thereof, using single or divided doses of every 24, 12, 8, 6, 4, or 2 hours, or any combination thereof.

The anti-CD38 antibodies may also be administered prophylactically in order to reduce the risk of developing multiple myeloma, delay the onset of the occurrence of an event in multiple myeloma progression, and/or reduce the risk of recurrence when multiple myeloma is in remission.

Exemplary corticosteroids include, for example, a glucocorticoid (cortisol, for example), prednisone, or dexamethasone. In some embodiments, the corticosteroid is dexamethasone. Thus, the methods can comprise administering to the subject a therapeutically effective amount of an anti-CD38 antibody, dexamethasone, and a non-corticosteroid chemotherapeutic agent for a time sufficient to treat the high-risk multiple myeloma.

In some embodiments, corticosteroid is administered about 80 mg weekly. In some embodiments, corticosteroid is administered about 40 mg weekly. In some embodiments, corticosteroid is administered twice a week. In some embodiments, corticosteroid is administered four times a week. In some embodiments, corticosteroid is administered once a week. In some embodiments, corticosteriod is administered orally. In some embodiments, corticosteroid is administered intravenously. In some embodiments, corticosteroid is dexamethasone.

Exemplary non-corticosteroid chemotherapeutic agents include glutamic acid derivatives or proteasome inhibitors. Exemplary glutamic acid derivatives include thalidomide (Thalomid®) or a thalidomide analog, e.g. CC-5013 (lenalidomide, Revlimid™), pomalidomide or CC4047 (Actimid™). In some embodiments, the glutamic acid derivative is lenalidomide. Thus, the methods can comprise administering to the subject a therapeutically effective amount of an anti-CD38 antibody, a corticosteroid, and lenalidomide for a time sufficient to treat the high-risk multiple myeloma.

In some embodiments, lenalinomide is administered between about 10 mg to about 25 mg once a day. In some embodiments, lenalinomide is administered about 25 mg once a day.

Exemplary proteasome inhibitors include bortezomib (Velcade®), carfilzomib, or ixazomib. In some embodiments, the proteasome inhibitor is bortezomib. Thus, the methods can comprise administering to the subject a therapeutically effective amount of an anti-CD38 antibody, a corticosteroid, and bortezomib for a time sufficient to treat the high-risk multiple myeloma.

In some embodiments, bortezomib is administered about 1.5 mg/m² once a week. In some embodiments, bortezomib is administered about 1.3 mg/m² once a week. In some embodiments, bortezomib is administered about 1.3 mg/m² to about 1.5 mg/m² once a week. In some embodiments, bortezomib is administered about 1.3 mg/m² twice a week. In some embodiments, bortezomib is administered by subcutaneous injection.

In some embodiments, the methods can comprise administering to the subject a therapeutically effective amount of an anti-CD38 antibody, dexamethasone, and lenalidomide for a time sufficient to treat the high-risk multiple myeloma. In some embodiments, the methods can comprise administering to the subject a therapeutically effective amount of an anti-CD38 antibody, dexamethasone, and bortezomib for a time sufficient to treat the high-risk multiple myeloma. In some embodiments, the methods can comprise administering to the subject a therapeutically effective amount of an anti-CD38 antibody, dexamethasone, lenalidomide, and bortezomib for a time sufficient to treat the high-risk multiple myeloma.

Subjects can be classified as "high-risk" if they have one or more of the following cytogenetic abnormalities: t(4;14)(p16;q32), t(14;16)(q32;q23), or del17p. Thus, the subject having high-risk multiple myeloma can have one or more chromosomal abnormalities comprising:
  a. t(4;14)(p16;q32);
  b. t(14;16)(q32;q23);
  c. del17p;
  d. t(4;14)(p16;q32) and t(14;16)(q32;q23);
  e. t(4;14)(p16;q32) and del17p;
  f. t(14;16)(q32;q23) and del17p; or
  g. t(4;14)(p16;q32), t(14;16)(q32;q23) and del17p.

Subjects can be classified as "standard risk" if they have none of the following cytogenetic abnormalities: t(4;14)(p16;q32), t(14;16)(q32;q23), or del17p.

The cytogenetic abnormalities can be detected by fluorescent in situ hybridization (FISH). In both chromosomal translocations, an oncogene is translocated to the IgH region on chromosome 14q32, resulting in dysregulation of these genes. t(4;14)(p16;q32) involves translocation of fibroblast growth factor receptor 3 (FGFR3) and multiple myeloma SET domain containing protein (MMSET) (also called WHSC1/NSD2), and t(14;16)(q32;q23) involves translocation of the MAF transcription factor C-MAF. Deletion of 17p (del17p) involves loss of the p53 gene locus.

The subject can have naive multiple myeloma, relapsed multiple myeloma, or refractory multiple myeloma. In some embodiments, the subject has high risk refractory and/or relapsed multiple myeloma.

The methods of treatment can improve one or more outcome measurements of the subject compared to a subject receiving the corticosteroid and the non-corticosteroid chemotherapeutic agent. Exemplary outcome measurements comprise progression-free survival, overall response rate, very good partial response or better, complete response or better, or any combination thereof.

The methods can achieve minimal residual disease-negativity in the subject. The negative minimal residual disease status can be determined at a sensitivity of 0.01% ($10^{-4}$), 0.001% ($10^{-5}$), 0.0001% ($10^{-6}$), or a combination thereof. The negative minimal residual disease can be detected by evaluating an amount of myeloma cells in a bone marrow aspirate sample from the subject.

The anti-CD38 antibody, corticosteroid, and non-corticosteroid chemotherapeutic agent may be administered over any convenient timeframe. In some embodiments, the anti-CD38 antibody, corticosteroid, and non-corticosteroid chemotherapeutic agent are administered simultaneously. In some embodiments, the anti-CD38 antibody, corticosteroid, and non-corticosteroid chemotherapeutic agent are administered sequentially in any order. An exemplary dosing schedule includes:

Daratumumab can be administered as an IV infusion at a dose of 16 mg/kg once per week (days 1, 8, and 15) for cycles 1-3, once every 4 weeks (on Day 1) during cycles 4-8, and once every 4 weeks thereafter. Bortezomib can be administered at a dose of 1.3 mg/m$^2$ subcutaneously (SC) on Days 1, 4, 8, and 11 of cycles 1-8. Dexamethasone can be administered orally at 20 mg on Days 1, 2, 4, 5, 8, 9, 11, and 12, for a total dose of 160 mg per cycle.

Daratumumab can be administered as an IV infusion at a dose of 16 mg/kg weekly (on days 1, 8, 15, and 22) for 8 weeks during cycles 1 and 2, every 2 weeks (on days 1 and 15) for 16 weeks (cycles 3 through 6), and every 4 weeks thereafter. Lenalidomide can be administered at a dose of 25 mg orally on days 1 to 21 of each cycle if the creatinine clearance is more than 60 ml per minute (or a dose of 10 mg daily if the creatinine clearance is 30 to 60 ml per minute) and dexamethasone at a dose of 40 mg weekly. For the daratumumab group, the dose of dexamethasone can be split: dexamethasone can be administered at a dose of 20 mg before infusion as prophylaxis for infusion-related reactions and 20 mg can be administered the next day.

The anti-CD38 antibody, corticosteroid, and non-corticosteroid chemotherapeutic agent may be administered together with any form of radiation therapy including external beam radiation, intensity modulated radiation therapy (IMRT) and any form of radiosurgery including Gamma Knife, Cyberknife, Linac, and interstitial radiation (e.g., implanted radioactive seeds, GliaSite balloon), and/or with surgery.

The anti-CD38 antibody, corticosteroid, and non-corticosteroid chemotherapeutic agent may be administered together with autologous hematopoietic stem cell transplant (AHSC).

Methods of Achieving Negative Minimal Residual Disease Status in a Subject

Also provided are methods of achieving negative minimal residual disease status in a subject having multiple myeloma comprising administering to the subject a therapeutically effective amount of an anti-CD38 antibody, a corticosteroid, and a non-corticosteroid chemotherapeutic agent for a time sufficient to achieve negative minimal residual disease status.

The negative minimal residual disease status can be determined at a sensitivity of 0.01% ($10^{-4}$), 0.001% ($10^{-5}$), 0.0001% ($10^{-6}$), or a combination thereof. In some embodiments, the negative minimal residual disease is detected by evaluating an amount of myeloma cells in a bone marrow aspirate sample from the subject.

In addition to achieving negative minimal residual disease status, the method also reduces progression-free survival events.

The subject can have naive multiple myeloma, relapsed multiple myeloma, or refractory multiple myeloma. In some embodiments, the subject has high-risk refractory and/or relapsed multiple myeloma. Subjects with high-risk multiple myeloma are known to relapse early and have poor prognosis and outcome.

In some embodiments, the subject has high-risk multiple myeloma. Subjects can be classified as "high risk" if they have one or more of the following cytogenetic abnormalities: t(4;14)(p16;q32), t(14;16)(q32;q23), or del17p. Thus, the subject having high-risk multiple myeloma can have one or more chromosomal abnormalities comprising:
  a. t(4;14)(p16;q32);
  b. t(14;16)(q32;q23);
  c. del17p;
  d. t(4;14)(p16;q32) and t(14;16)(q32;q23);
  e. t(4;14)(p16;q32) and del17p;
  f. t(14;16)(q32;q23) and del17p; or
  g. t(4;14)(p16;q32), t(14;16)(q32;q23) and del17p.

Any of the anti-CD38 antibodies disclosed above for the methods of treatment can be used in the methods of achieving negative minimal residual disease status in a subject having multiple myeloma.

The anti-CD38 antibody can bind to a region of human CD38 comprising SKRNIQFSCKNIYR (SEQ ID NO: 2) and a region of human CD38 comprising EKVQTLEAWVIHGG (SEQ ID NO: 3).

The anti-CD38 antibody can comprise a heavy chain CDR1 comprising the amino acid sequence of SEQ ID NO: 6, a heavy chain CDR2 comprising the amino acid sequence of SEQ ID NO: 7, a heavy chain CDR3 comprising the amino acid sequence of SEQ ID NO: 8, a light chain CDR1 comprising the amino acid sequence of SEQ ID NO: 9, a light chain CDR2 comprising the amino acid sequence of SEQ ID NO: 10, and a light chain CDR3 comprising the amino acid sequence of SEQ ID NO: 11. The anti-CD38 antibody can comprise a VH comprising an amino acid sequence that is 95%, 96%, 97%, 98%, 99%, or 100% identical to that of SEQ ID NO: 4 and a VL comprising an amino acid sequence that is 95%, 96%, 97%, 98%, 99%, or 100% identical to that of SEQ ID NO: 5. In some embodiments, the anti-CD38 antibody can comprise a VH comprising the amino acid sequence of SEQ ID NO: 4 and a VL comprising the amino acid sequence of SEQ ID NO: 5. The anti-CD38 antibody can comprise a heavy chain comprising the amino acid sequence of SEQ ID NO: 12 and a light chain comprising the amino acid sequence of SEQ ID NO: 13.

The anti-CD38 antibody can comprise a heavy chain CDR1, a heavy chain CDR2, and a heavy chain CDR3 of a VH comprising the amino acid sequence of SEQ ID NO: 14, and a light chain CDR1, a light chain CDR2, and a light chain CDR3 of a VL comprising the amino acid sequence of SEQ ID NOs:15. The anti-CD38 antibody can comprise a VH comprising an amino acid sequence that is 95%, 96%, 97%, 98%, 99%, or 100% identical to that of SEQ ID NO: 15 and a VL comprising an amino acid sequence that is 95%, 96%, 97%, 98%, 99%, or 100% identical to that of SEQ ID NO: 15. In some embodiments, the anti-CD38 antibody can comprise a VH comprising the amino acid sequence of SEQ ID NO: 14 and a VL comprising the amino acid sequence of SEQ ID NO:15. In some embodiments, for example, the anti-CD38 antibody can comprise mAb003 (described in U.S. Pat. No. 7,829,693, incorporated herein by reference).

The anti-CD38 antibody can comprise a heavy chain CDR1, a heavy chain CDR2, and a heavy chain CDR3 of a VH comprising the amino acid sequence of SEQ ID NO: 16, and a light chain CDR1, a light chain CDR2, and a light chain CDR3 of a VL comprising the amino acid sequence of SEQ ID NO: 17. The anti-CD38 antibody can comprise a VH comprising an amino acid sequence that is 95%, 96%, 97%, 98%, 99%, or 100% identical to that of SEQ ID NO: 16 and a VL comprising an amino acid sequence that is 95%, 96%, 97%, 98%, 99%, or 100% identical to that of SEQ ID NO: 17. In some embodiments, the anti-CD38 antibody can comprise a VH comprising the amino acid sequence of SEQ ID NO: 16 and a VL comprising the amino acid sequence of SEQ ID NO: 17. In some embodiments, for example, the anti-CD38 antibody can comprise mAb024 (described in U.S. Pat. No. 7,829,693, incorporated herein by reference).

The anti-CD38 antibody can comprise a heavy chain CDR1, a heavy chain CDR2, and a heavy chain CDR3 of a VH comprising the amino acid sequence of SEQ ID NO: 18, and a light chain CDR1, a light chain CDR2, and a light chain CDR3 of a VL comprising the amino acid sequence of SEQ ID NO: 19. The anti-CD38 antibody can comprise a VH comprising an amino acid sequence that is 95%, 96%, 97%, 98%, 99%, or 100% identical to that of SEQ ID NO: 18 and a VL comprising an amino acid sequence that is 95%, 96%, 97%, 98%, 99%, or 100% identical to that of SEQ ID NO: 19. In some embodiments, the anti-CD38 antibody can comprise a VH comprising the amino acid sequence of SEQ ID NO: 18 and a VL comprising the amino acid sequence of SEQ ID NO: 19. In some embodiments, for example, the anti-CD38 antibody can comprise MOR-202 (MOR-03087) (described in U.S. Pat. No. 8,088,896, incorporated herein by reference).

The anti-CD38 antibody can comprise a heavy chain CDR1, a heavy chain CDR2, and a heavy chain CDR3 of a VH comprising the amino acid sequence of SEQ ID NO: 20, and a light chain CDR1, a light chain CDR2, and a light chain CDR3 of a VL comprising the amino acid sequence of SEQ ID NO: 21. The anti-CD38 antibody can comprise a VH comprising an amino acid sequence that is 95%, 96%, 97%, 98%, 99%, or 100% identical to that of SEQ ID NO: 20 and a VL comprising an amino acid sequence that is 95%, 96%, 97%, 98%, 99%, or 100% identical to that of SEQ ID NO: 21. In some embodiments, the anti-CD38 antibody can comprise a VH comprising the amino acid sequence of SEQ ID NO: 20 and a VL comprising the amino acid sequence of SEQ ID NO: 21. In some embodiments, for example, the anti-CD38 antibody can comprise isatuximab (described in U.S. Pat. No. 8,153,765, incorporated herein by reference). In some aspects, the VH and the VL of isatuximab may be expressed as IgG1/κ.

Any of the corticosteroids and non-corticosteroid chemotherapeutic agents disclosed above for the methods of treatment can be used in the methods of achieving negative minimal residual disease status in a subject having multiple myeloma. Suitable corticosteroids include, for example, a glucocorticoid (cortisol, for example), prednisone, or dexamethasone. In some embodiments, the corticosteroid is dexamethasone. Suitable non-corticosteroid chemotherapeutic agents include glutamic acid derivatives or proteasome inhibitors. Exemplary glutamic acid derivatives include thalidomide (Thalomid®) or a thalidomide analog, e.g. CC-5013 (lenalidomide, Revlimid™), pomalidomide or CC4047 (Actimid™). In some embodiments, the glutamic acid derivative is lenalidomide. Suitable proteasome inhibitors include bortezomib (Velcade®), carfilzomib, or ixazomib. In some embodiments, the proteasome inhibitor is bortezomib.

Methods of Predicting a Likelihood of, or Decreasing a Risk of, Relapse and/or Disease Progression Provided are methods of predicting a likelihood of relapse and/or disease progression in a subject having multiple myeloma and methods of decreasing a risk of relapse and/or disease progression in a subject having multiple myeloma.

The methods of predicting a likelihood of relapse and/or disease progression in a subject having multiple myeloma comprise:
  measuring a minimal residual disease status in the subject, wherein the subject has received a therapeutically effective amount of an anti-CD38 antibody,
  wherein a positive minimal residual disease status is indicative of a likelihood of relapse and/or disease progression.

The methods of predicting a likelihood of relapse and/or disease progression in a subject having multiple myeloma comprise:
  measuring a minimal residual disease status in the subject, wherein the subject has received a therapeutically effective amount of an anti-CD38 antibody, a corticosteroid, and a non-corticosteroid chemotherapeutic agent,
  wherein a positive minimal residual disease status is indicative of a likelihood of relapse and/or disease progression.

The methods of decreasing a risk of relapse and/or disease progression in a subject having multiple myeloma comprise:
  administering to the subject a therapeutically effective amount of an anti-CD38 antibody, a corticosteroid, and a non-corticosteroid chemotherapeutic agent to achieve a negative minimal residual disease status, wherein the negative residual disease status is indicative of a decreased risk of relapse and/or disease progression.

The subject can have naive multiple myeloma, relapsed multiple myeloma, refractory multiple myeloma, or relapsed and refractory multiple myeloma. In some embodiments, the subject has high risk refractory, relapsed, or relapsed and refractory multiple myeloma.

In some embodiments, the subject has high risk multiple myeloma. Subjects can be classified as "high-risk" if they have one or more of the following cytogenetic abnormalities: t(4;14)(p16;q32), t(14;16)(q32;q23), or del17p. Thus, the subject having high-risk multiple myeloma can have one or more chromosomal abnormalities comprising:

a. t(4;14)(p16;q32);
b. t(14;16)(q32;q23);
c. del17p;
d. t(4;14)(p16;q32) and t(14;16)(q32;q23);
e. t(4;14)(p16;q32) and del17p;
f. t(14;16)(q32;q23) and del17p; or
g. t(4;14)(p16;q32), t(14;16)(q32;q23) and del17p.

Any of the anti-CD38 antibodies disclosed above for the methods of treatment can be used in the methods of predicting a likelihood of relapse and/or disease progression in a subject having multiple myeloma and methods of decreasing a risk of relapse and/or disease progression in a subject having multiple myeloma.

The anti-CD38 antibody can bind to a region of human CD38 comprising SKRNIQFSCKNIYR (SEQ ID NO: 2) and a region of human CD38 comprising EKVQTLEAWVIHGG (SEQ ID NO: 3).

The anti-CD38 antibody can comprise a heavy chain CDR1 comprising the amino acid sequence of SEQ ID NO: 6, a heavy chain CDR2 comprising the amino acid sequence of SEQ ID NO: 7, a heavy chain CDR3 comprising the amino acid sequence of SEQ ID NO: 8, a light chain CDR1 comprising the amino acid sequence of SEQ ID NO: 9, a light chain CDR2 comprising the amino acid sequence of SEQ ID NO: 10, and a light chain CDR3 comprising the amino acid sequence of SEQ ID NO: 11. The anti-CD38 antibody can comprise a VH comprising an amino acid sequence that is 95%, 96%, 97%, 98%, 99%, or 100% identical to that of SEQ ID NO: 4 and a VL comprising an amino acid sequence that is 95%, 96%, 97%, 98%, 99%, or 100% identical to that of SEQ ID NO: 5. In some embodiments, the anti-CD38 antibody can comprise VH comprising the amino acid sequence of SEQ ID NO: 4 and VL comprising the amino acid sequence of SEQ ID NO: 5. The anti-CD38 antibody can comprise a heavy chain comprising the amino acid sequence of SEQ ID NO: 12 and a light chain comprising the amino acid sequence of SEQ ID NO: 13.

The anti-CD38 antibody can comprise a heavy chain CDR1, a heavy chain CDR2, and a heavy chain CDR3 of a VH comprising the amino acid sequence of SEQ ID NO: 14, and a light chain CDR1, a light chain CDR2, and a light chain CDR3 of a VL comprising the amino acid sequence of SEQ ID NO:15. The anti-CD38 antibody can comprise a VH comprising an amino acid sequence that is 95%, 96%, 97%, 98%, 99%, or 100% identical to that of SEQ ID NO: 15 and a VL comprising an amino acid sequence that is 95%, 96%, 97%, 98%, 99%, or 100% identical to that of SEQ ID NO: 15. In some embodiments, the anti-CD38 antibody can comprise a VH comprising the amino acid sequence of SEQ ID NO: 14 and a VL comprising the amino acid sequence of SEQ ID NOs:15. In some embodiments, for example, the anti-CD38 antibody can comprise mAb003 (described in U.S. Pat. No. 7,829,693, incorporated herein by reference).

The anti-CD38 antibody can comprise a heavy chain CDR1, a heavy chain CDR2, and a heavy chain CDR3 of a VH comprising the amino acid sequence of SEQ ID NO: 16, and a light chain CDR1, a light chain CDR2, and a light chain CDR3 of a VL comprising the amino acid sequence of SEQ ID NO: 17. The anti-CD38 antibody can comprise a VH comprising an amino acid sequence that is 95%, 96%, 97%, 98%, 99%, or 100% identical to that of SEQ ID NO: 16 and a VL comprising an amino acid sequence that is 95%, 96%, 97%, 98%, 99%, or 100% identical to that of SEQ ID NO: 17. In some embodiments, the anti-CD38 antibody can comprise a VH comprising the amino acid sequence of SEQ ID NO: 16 and a VL comprising the amino acid sequence of SEQ ID NO: 17. In some embodiments, for example, the anti-CD38 antibody can comprise mAb024 (described in U.S. Pat. No. 7,829,693, incorporated herein by reference).

The anti-CD38 antibody can comprise a heavy chain CDR1, a heavy chain CDR2, and a heavy chain CDR3 of a VH comprising the amino acid sequence of SEQ ID NO: 18, and a light chain CDR1, a light chain CDR2, and a light chain CDR3 of a VL comprising the amino acid sequence of SEQ ID NO: 19. The anti-CD38 antibody can comprise a VH comprising an amino acid sequence that is 95%, 96%, 97%, 98%, 99%, or 100% identical to that of SEQ ID NO: 18 and a VL comprising an amino acid sequence that is 95%, 96%, 97%, 98%, 99%, or 100% identical to that of SEQ ID NO: 19. In some embodiments, the anti-CD38 antibody can comprise a VH comprising the amino acid sequence of SEQ ID NO: 18 and a VL comprising the amino acid sequence of SEQ ID NO: 19. In some embodiments, for example, the anti-CD38 antibody can comprise MOR-202 (MOR-03087) (described in U.S. Pat. No. 8,088,896, incorporated herein by reference).

The anti-CD38 antibody can comprise a heavy chain CDR1, a heavy chain CDR2, and a heavy chain CDR3 of a VH comprising the amino acid sequence of SEQ ID NO: 20, and a light chain CDR1, a light chain CDR2, and a light chain CDR3 of a VL comprising the amino acid sequence of SEQ ID NO: 21. The anti-CD38 antibody can comprise a VH comprising an amino acid sequence that is 95%, 96%, 97%, 98%, 99%, or 100% identical to that of SEQ ID NO: 20 and a VL comprising an amino acid sequence that is 95%, 96%, 97%, 98%, 99%, or 100% identical to that of SEQ ID NO: 21. In some embodiments, the anti-CD38 antibody can comprise a VH comprising the amino acid sequence of SEQ ID NO: 20 and a VL comprising the amino acid sequence of SEQ ID NO: 21. In some embodiments, for example, the anti-CD38 antibody can comprise isatuximab (described in U.S. Pat. No. 8,153,765, incorporated herein by reference). In some aspects, the VH and the VL of isatuximab may be expressed as IgG1/κ.

Any of the corticosteroids and non-corticosteroid chemotherapeutic agents disclosed above for the methods of treatment can be used in the methods of predicting a likelihood of relapse and/or disease progression in a subject having multiple myeloma and methods of decreasing a risk of relapse and/or disease progression in a subject having multiple myeloma. Suitable corticosteroids include, for example, a glucocorticoid (cortisol, for example), prednisone, or dexamethasone. In some embodiments, the corticosteroid is dexamethasone. Suitable non-corticosteroid chemotherapeutic agents include glutamic acid derivatives or proteasome inhibitors. Exemplary glutamic acid derivatives include thalidomide (Thalomid®) or a thalidomide analog, e.g. CC-5013 (lenalidomide, Revlimid™), pomalidomide or CC4047 (Actimid™). In some embodiments, the glutamic acid derivative is lenalidomide. Suitable proteasome inhibitors include bortezomib (Velcade®), carfilzomib, or ixazomib. In some embodiments, the proteasome inhibitor is bortezomib.

A description of example embodiments follows.

Embodiment 1

A method of achieving negative minimal residual disease status in a subject having multiple myeloma comprising administering to the subject a therapeutically effective amount of an anti-CD38 antibody, a corticosteroid, and a non-corticosteroid chemotherapeutic agent for a time sufficient to achieve negative minimal residual disease status.

Embodiment 2

The method of Embodiment 1, wherein the anti-CD38 antibody comprises a heavy chain CDR1 comprising the amino acid sequence of SEQ ID NO: 6, a heavy chain CDR2 comprising the amino acid sequence of SEQ ID NO: 7, a heavy chain CDR3 comprising the amino acid sequence of SEQ ID NO: 8, a light chain CDR1 comprising the amino acid sequence of SEQ ID NO: 9, a light chain CDR2 comprising the amino acid sequence of SEQ ID NO: 10, and a light chain CDR3 comprising the amino acid sequence of SEQ ID NO: 11.

Embodiment 3

The method of Embodiments 1-2, wherein the corticosteroid is dexamethasone.

Embodiment 4

The method of Embodiments 1-3, wherein the non-corticosteroid chemotherapeutic agent is a glutamic acid derivative or a proteasome inhibitor.

Embodiment 5

The method of Embodiment 4, wherein the glutamic acid derivative is lenalidomide.

Embodiment 6

The method of Embodiment 4, wherein the proteasome inhibitor is bortezomib.

Embodiment 7

The method of Embodiment 5, wherein
the anti-CD38 antibody is administered as an intravenous infusion at a dose of about 16 mg/kg once per week in a 28-day cycle on days 1, 8, 15, and 22 for cycles 1 and 2, once every 2 weeks in a 28-day cycle on days 1 and 15 during cycles 3 through 6, and once every 4 weeks thereafter;
lenalidomide is administered at a dose of between about 10 mg to about 25 mg orally in a 28-day cycle on days 1 to 21; and
dexamethasone is administered at a dose of between about 20 mg to about 40 mg weekly.

Embodiment 8

The method of Embodiment 6, wherein
the anti-CD38 antibody is administered as an intravenous infusion at a dose of about 16 mg/kg once per week in a 21-day cycle on days 1, 8, and 15 for cycles 1-3, once every 3 weeks in a 21-day cycle on day 1 for cycles 4-8, and once every 4 weeks thereafter; and
bortezomib is administered at a dose of about 1.3 mg/m2 subcutaneously (SC) in a 21-day cycle on days 1, 4, 8, and 11 for cycles 1-8; and
dexamethasone is administered at a dose of between about 20 mg to about 40 mg weekly.

Embodiment 9

The method of Embodiment 7, wherein dexamethasone is administered at 20 mg on days 1, 2, 4, 5, 8, 9, 11, and 12 for a total dose of 160 mg per cycle IV or PO.

Embodiment 10

The method of Embodiment 8, wherein dexamethasone is administered at 20 mg on days 1, 2, 4, 5, 8, 9, 11, and 12 for a total dose of 160 mg per cycle IV or PO.

Embodiment 11

The method of Embodiments 1-10, wherein the subject has relapsed or refractory multiple myeloma.

Embodiment 12

The method of Embodiments 1-11, wherein the subject has high risk multiple myeloma.

Embodiment 13

The method of Embodiment 12, wherein the subject having high-risk multiple myeloma has one or more chromosomal abnormalities comprising:
t(4;14)(p16;q32);
t(14;16)(q32;q23);
del17p;
t(4;14)(p16;q32) and t(14;16)(q32;q23);
t(4;14)(p16;q32) and del17p;
t(14;16)(q32;q23) and del17p; or
t(4;14)(p16;q32), t(14;16)(q32;q23) and del17p.

Embodiment 14

The method of Embodiments 1-13, wherein the negative minimal residual disease status is determined at a sensitivity of 0.01%, 0.001%, 0.0001%, or a combination thereof.

Embodiment 15

The method of Embodiments 1-14, wherein the anti-CD38 antibody binds to a region of human CD38 comprising SEQ ID NO: 2 and a region of human CD38 comprising SEQ ID NO: 3.

Embodiment 16

The method of Embodiments 1-15, wherein the anti-CD38 antibody comprises a heavy chain variable region comprising the amino acid sequence of SEQ ID NO: 4 and a light chain variable region comprising the amino acid sequence of SEQ ID NO: 5.

Embodiment 17

The method of Embodiments 1-16, wherein the anti-CD38 antibody comprises a heavy chain comprising the amino acid sequence of SEQ ID NO: 12 and a light chain comprising the amino acid sequence of SEQ ID NO: 13.

Embodiment 18

The method of Embodiments 1-13, wherein the anti-CD38 antibody comprises a heavy chain CDR1, a heavy chain CDR2, a heavy chain CDR3, a light chain CDR1, a light chain CDR2 and a light chain CDR3 of:

a VH comprising the amino acid sequence of SEQ ID NO: 14 and a VL comprising the amino acid sequence of SEQ ID NO: 15;

a VH comprising the amino acid sequence of SEQ ID NO: 16 and a VL comprising the amino acid sequence of SEQ ID NO: 17;

a VH comprising the amino acid sequence of SEQ ID NO: 18 and a VL comprising the amino acid sequence of SEQ ID NO: 19; or a VH comprising the amino acid sequence of SEQ ID NO: 20 and a VL comprising the amino acid sequence of SEQ ID NO: 21.

Embodiment 19

The method of Embodiment 18, wherein the anti-CD38 antibody comprises:

a VH comprising the amino acid sequence of SEQ ID NO: 14 and a VL comprising the amino acid sequence of SEQ ID NO: 15;

a VH comprising the amino acid sequence of SEQ ID NO: 16 and a VL comprising the amino acid sequence of SEQ ID NO: 17;

a VH comprising the amino acid sequence of SEQ ID NO: 18 and a VL comprising the amino acid sequence of SEQ ID NO: 19; or a VH comprising the amino acid sequence of SEQ ID NO: 20 and a VL comprising the amino acid sequence of SEQ ID NO: 21.

Embodiment 20

The method of Embodiments 1-2, wherein the corticosteroid is dexamethasone or prednisone.

Embodiment 21

The method of Embodiments 1-20, wherein the negative minimal residual disease is detected by evaluating an amount of myeloma cells in a bone marrow aspirate sample from the subject.

Embodiment 22

The method of Embodiments 1-21, wherein the method also reduces progression-free survival events.

Embodiment 23

The method of Embodiment 4, wherein the glutamic acid derivative is lenalidomide, thalidomide, or pomalidomide.

Embodiment 24

The method of Embodiment 4, wherein the proteasome inhibitor is bortezomib, carfilzomib, or ixazomib.

Embodiment 25

A method of treating a subject having high-risk multiple myeloma, comprising administering to the subject a therapeutically effective amount of an anti-CD38 antibody, a corticosteroid, and a non-corticosteroid chemotherapeutic agent for a time sufficient to treat the high-risk multiple myeloma.

Embodiment 26

The method of Embodiment 25, wherein the anti-CD38 antibody comprises a heavy chain CDR1 comprising the amino acid sequence of SEQ ID NO: 6, a heavy chain CDR2 comprising the amino acid sequence of SEQ ID NO: 7, a heavy chain CDR3 comprising the amino acid sequence of SEQ ID NO: 8, a light chain CDR1 comprising the amino acid sequence of SEQ ID NO: 9, a light chain CDR2 comprising the amino acid sequence of SEQ ID NO: 10, and a light chain CDR3 comprising the amino acid sequence of SEQ ID NO: 11.

Embodiment 27

The method of Embodiments 25-26, wherein the corticosteroid is dexamethasone.

Embodiment 28

The method of Embodiments 25-27, wherein the non-corticosteroid chemotherapeutic agent is a glutamic acid derivative or a proteasome inhibitor.

Embodiment 29

The method of Embodiment 28, wherein the glutamic acid derivative is lenalidomide.

Embodiment 30

The method of Embodiment 28, wherein the proteasome inhibitor is bortezomib.

Embodiment 31

The method of Embodiment 29, wherein
the anti-CD38 antibody is administered as an intravenous infusion at a dose of about 16 mg/kg once per week in a 28-day cycle on days 1, 8, 15, and 22 for cycles 1 and 2, once every 2 weeks in a 28-day cycle on days 1 and 15 during cycles 3 through 6, and once every 4 weeks thereafter; and
lenalidomide is administered at a dose of between about 10 mg to about 25 mg orally in a 28-day cycle on days 1 to 21; and
dexamethasone is administered at a dose of between about 20 mg to about 40 mg weekly.

Embodiment 32

The method of Embodiment 30, wherein
the anti-CD38 antibody is administered as an intravenous infusion at a dose of about 16 mg/kg once per week in a 21-day cycle on days 1, 8, and 15 for cycles 1-3, once every 3 weeks in a 21-day cycle on day 1 for cycles 4-8, and once every 4 weeks thereafter; and
bortezomib is administered at a dose of about 1.3 mg/m2 subcutaneously (SC) in a 21-day cycle on days 1, 4, 8, and 11 for cycles 1-8; and
dexamethasone is administered at a dose of between about 20 mg to about 40 mg weekly.

Embodiment 33

The method of Embodiment 31, wherein dexamethasone is administered at 20 mg on days 1, 2, 4, 5, 8, 9, 11, and 12 for a total dose of 160 mg per cycle IV or PO.

Embodiment 34

The method of Embodiment 32, wherein dexamethasone is administered at 20 mg on days 1, 2, 4, 5, 8, 9, 11, and 12 for a total dose of 160 mg per cycle IV or PO.

Embodiment 35

The method of Embodiments 25-34, wherein the anti-CD38 antibody binds to a region of human CD38 comprising SEQ ID NO: 2 and a region of human CD38 comprising SEQ ID NO: 3.

Embodiment 36

The method of Embodiments 25-35, wherein the anti-CD38 antibody comprises a heavy chain variable region comprising the amino acid sequence of SEQ ID NO: 4 and a light chain variable region comprising the amino acid sequence of SEQ ID NO: 5.

Embodiment 37

The method of Embodiments 25-36, wherein the anti-CD38 antibody comprises a heavy chain comprising the amino acid sequence of SEQ ID NO: 12 and a light chain comprising the amino acid sequence of SEQ ID NO: 13.

Embodiment 38

The method of Embodiment 25, wherein the anti-CD38 antibody comprises a heavy chain CDR1, a heavy chain CDR2, a heavy chain CDR3, a light chain CDR1, a light chain CDR2 and a light chain CDR3 of: a VH comprising the amino acid sequence of SEQ ID NO: 14 and a VL comprising the amino acid sequence of SEQ ID NO: 15; a VH comprising the amino acid sequence of SEQ ID NO: 16 and a VL comprising the amino acid sequence of SEQ ID NO: 17; a VH comprising the amino acid sequence of SEQ ID NO: 18 and a VL comprising the amino acid sequence of SEQ ID NO: 19; or a VH comprising the amino acid sequence of SEQ ID NO: 20 and a VL comprising the amino acid sequence of SEQ ID NO: 21.

Embodiment 39

The method of Embodiment 38, wherein the anti-CD38 antibody comprises:
a VH comprising the amino acid sequence of SEQ ID NO: 14 and a VL comprising the amino acid sequence of SEQ ID NO: 15;
a VH comprising the amino acid sequence of SEQ ID NO: 16 and a VL comprising the amino acid sequence of SEQ ID NO: 17;
a VH comprising the amino acid sequence of SEQ ID NO: 18 and a VL comprising the amino acid sequence of SEQ ID NO: 19; or
a VH comprising the amino acid sequence of SEQ ID NO: 20 and a VL comprising the amino acid sequence of SEQ ID NO: 21.

Embodiment 40

The method of Embodiment 25, wherein the corticosteroid is dexamethasone or prednisone.

Embodiment 41

The method of Embodiment 25, wherein the corticosteroid is dexamethasone.

Embodiment 42

The method of Embodiment 25, wherein the non-corticosteroid chemotherapeutic agent is a glutamic acid derivative or a proteasome inhibitor.

Embodiment 43

The method of Embodiment 42, wherein the glutamic acid derivative is lenalidomide, thalidomide, or pomalidomide.

Embodiment 44

The method of Embodiment 42, wherein the glutamic acid derivative is lenalidomide.

Embodiment 45

The method of Embodiment 42, wherein the proteasome inhibitor is bortezomib, carfilzomib, or ixazomib.

Embodiment 46

The method of Embodiment 42, wherein the proteasome inhibitor is bortezomib.

Embodiment 47

The method of Embodiment 25, wherein the subject having high-risk multiple myeloma has one or more chromosomal abnormalities comprising:
t(4;14)(p16;q32);
t(14;16)(q32;q23);
del17p;
t(4;14)(p16;q32) and t(14;16)(q32;q23);
t(4;14)(p16;q32) and del17p;
t(14;16)(q32;q23) and del17p; or
t(4;14)(p16;q32), t(14;16)(q32;q23) and del17p.

Embodiment 48

The method of Embodiment 25, wherein the subject has high risk refractory or relapsed multiple myeloma.

Embodiment 49

The method of Embodiment 25, wherein the method improves one or more outcome measurements of the subject compared to a subject receiving the corticosteroid and the non-corticosteroid chemotherapeutic agent.

Embodiment 50

The method of Embodiment 49, wherein the one or more outcome measurements comprise progression-free survival, overall response rate, very good partial response or better, complete response or better, or any combination thereof.

Embodiment 51

The method of Embodiment 25, wherein the method achieves minimal residual disease-negativity in the subject.

Embodiment 52

A method of decreasing a risk of relapse and/or disease progression in a subject having multiple myeloma comprising:

administering to the subject a therapeutically effective amount of an anti-CD38 antibody, a corticosteroid, and a non-corticosteroid chemotherapeutic agent to achieve a negative minimal residual disease status, wherein the negative residual disease status is indicative of a decreased risk of relapse and/or disease progression.

Embodiment 53

A method of predicting a likelihood of relapse and/or disease progression in a subject having multiple myeloma comprising:

measuring a minimal residual disease status in the subject, wherein the subject has received a therapeutically effective amount of an anti-CD38 antibody, a corticosteroid, and a non-corticosteroid chemotherapeutic agent, wherein a positive minimal residual disease status is indicative of a likelihood of relapse and/or disease progression.

Embodiment 54

The method of Embodiments 52-53, wherein the anti-CD38 antibody comprises a heavy chain CDR1 comprising the amino acid sequence of SEQ ID NO: 6, a heavy chain CDR2 comprising the amino acid sequence of SEQ ID NO: 7, a heavy chain CDR3 comprising the amino acid sequence of SEQ ID NO: 8, a light chain CDR1 comprising the amino acid sequence of SEQ ID NO: 9, a light chain CDR2 comprising the amino acid sequence of SEQ ID NO: 10, and a light chain CDR3 comprising the amino acid sequence of SEQ ID NO: 11.

Embodiment 55

The method of Embodiments 52-54, wherein the corticosteroid is dexamethasone.

Embodiment 56

The method of Embodiments 52-55, wherein the non-corticosteroid chemotherapeutic agent is a glutamic acid derivative or a proteasome inhibitor.

Embodiment 57

The method of Embodiment 56, wherein the glutamic acid derivative is lenalidomide.

Embodiment 58

The method of Embodiment 56, wherein the proteasome inhibitor is bortezomib.

Embodiment 59

The method of Embodiment 57, wherein the anti-CD38 antibody is administered as an intravenous infusion at a dose of about 16 mg/kg once per week in a 28-day cycle on days 1, 8, 15, and 22 for cycles 1 and 2, once every 2 weeks in a 28-day cycle on days 1 and 15 during cycles 3 through 6, and once every 4 weeks thereafter;

lenalidomide is administered at a dose of between about 10 mg to about 25 mg orally in a 28-day cycle on days 1 to 21; and dexamethasone is administered at a dose of between about 20 mg to about 40 mg weekly.

Embodiment 60

The method of Embodiment 58, wherein the anti-CD38 antibody is administered as an intravenous infusion at a dose of about 16 mg/kg once per week in a 21-day cycle on days 1, 8, and 15 for cycles 1-3, once every 3 weeks in a 21-day cycle on day 1 for cycles 4-8, and once every 4 weeks thereafter; and bortezomib is administered at a dose of about 1.3 mg/m2 subcutaneously (SC) in a 21-day cycle on days 1, 4, 8, and 11 for cycles 1-8; and dexamethasone is administered at a dose of between about 20 mg to about 40 mg weekly.

Embodiment 61

The method of Embodiments 55-60, wherein dexamethasone is administered at 20 mg on days 1, 2, 4, 5, 8, 9, 11, and 12 for a total dose of 160 mg per cycle IV or PO.

Embodiment 62

The method of Embodiments 52-61, wherein the subject has relapsed or refractory multiple myeloma.

Embodiment 63

The method of Embodiments 52-62, wherein the subject has high risk multiple myeloma.

Embodiment 64

The method of Embodiment 63, wherein the subject having high-risk multiple myeloma has one or more chromosomal abnormalities comprising:
t(4;14)(p16;q32);
t(14;16)(q32;q23);
del17p;
t(4;14)(p16;q32) and t(14;16)(q32;q23);
t(4;14)(p16;q32) and del17p;
t(14;16)(q32;q23) and del17p; or
t(4;14)(p16;q32), t(14;16)(q32;q23) and del17p.

Embodiment 65

The method of Embodiments 52-64, wherein the anti-CD38 antibody binds to a region of human CD38 comprising SEQ ID NO: 2 and a region of human CD38 comprising SEQ ID NO: 3.

Embodiment 66

The method of Embodiments 52-65, wherein the anti-CD38 antibody comprises a heavy chain variable region comprising the amino acid sequence of SEQ ID NO: 4 and a light chain variable region comprising the amino acid sequence of SEQ ID NO: 5.

Embodiment 67

The method of Embodiments 52-66, wherein the anti-CD38 antibody comprises a heavy chain comprising the amino acid sequence of SEQ ID NO: 12 and a light chain comprising the amino acid sequence of SEQ ID NO: 13.

Embodiment 68

The method of Embodiments 52-64, wherein the anti-CD38 antibody comprises a heavy chain CDR1, a heavy chain CDR2, a heavy chain CDR3, a light chain CDR1, a light chain CDR2 and a light chain CDR3 of:

a VH comprising the amino acid sequence of SEQ ID NO: 14 and a VL comprising the amino acid sequence of SEQ ID NO: 15;

a VH comprising the amino acid sequence of SEQ ID NO: 16 and a VL comprising the amino acid sequence of SEQ ID NO: 17;

a VH comprising the amino acid sequence of SEQ ID NO: 18 and a VL comprising the amino acid sequence of SEQ ID NO: 19; or a VH comprising the amino acid sequence of SEQ ID NO: 20 and a VL comprising the amino acid sequence of SEQ ID NO: 21.

Embodiment 69

The method of Embodiment 68, wherein the anti-CD38 antibody comprises:

a VH comprising the amino acid sequence of SEQ ID NO: 14 and a VL comprising the amino acid sequence of SEQ ID NO: 15;

a VH comprising the amino acid sequence of SEQ ID NO: 16 and a VL comprising the amino acid sequence of SEQ ID NO: 17;

a VH comprising the amino acid sequence of SEQ ID NO: 18 and a VL comprising the amino acid sequence of SEQ ID NO: 19; or a VH comprising the amino acid sequence of SEQ ID NO: 20 and a VL comprising the amino acid sequence of SEQ ID NO: 21.

Embodiment 70

The method of Embodiments 52-54, wherein the corticosteroid is dexamethasone or prednisone.

Embodiment 71

The method of Embodiment 56, wherein the glutamic acid derivative is lenalidomide, thalidomide, or pomalidomide.

Embodiment 72

The method of Embodiment 56, wherein the proteasome inhibitor is bortezomib, carfilzomib, or ixazomib.

EXAMPLES

The following examples are provided to further describe some of the embodiments disclosed herein. The examples are intended to illustrate, not to limit, the disclosed embodiments.

Example 1. Study Design NCT02136134 (Castor)

The purpose of this study is to assess the effects of administration of daratumumab when combined with VELCADE® (bortezomib) and dexamethasone compared with VELCADE® (bortezomib) and dexamethasone alone, for participants with relapsed or refractory multiple myeloma. The study was a multicenter, randomized open-label active-controlled phase 3 trial. A prespecified interim analysis has been described in Palumpo et al., *NEJM* 375: 754-66, 2016. The clinical trial number for this study is NCT02136134.

Eligibility

Patients with documented progressive multiple myeloma (according to International Myeloma Working Group IMWG criteria) who had received at least one previous therapy for multiple myeloma and had at least a partial response to the at least one previous therapy were eligible.

Exclusion Criteria

Patients who had received daratumumab or other anti-CD38 therapies previously, patients who were refractory to or who had unacceptable side effects from bortezomib, patients with a neutrophil count <1000 cells/mm$^3$, hemoglobin <7.5 g/dl, platelet count <75,000/mm$^3$, creatinine clearance <20 ml/min per 1.73 m$^2$ body-surface area, alanine aminotransferase or aspartate aminotransferase level of 2.5 or more times the upper limit of the normal range, and bilirubin level or 1.5 or more times the upper limit of the normal range, patients who had disease that was refractory to another proteasome inhibitor, or patients who had grade 2 or higher peripheral neutropathy or neuropathic pain were excluded from the study.

Trial Treatments 498 patients were randomly assigned in a 1:1 ratio to receive daratumumab, bortezomib and dexamethasone (DVd; "daratumumab group") or bortezomib and dexamethasone (Vd; "control group"). Randomization was stratified by International Staging System (ISS), number of prior treatment programs (1 vs. 2 or 3 vs. >3), and prior VELCADE® treatment ("no" vs. "yes").

Daratumumab was administered as an IV infusion at a dose of 16 mg/kg once per week (days 1, 8, and 15) for cycles 1-3, once every 3 weeks (on Day 1) during cycles 4-8, and once every 4 weeks thereafter. VELCADE® was administered at a dose of 1.3 mg/m$^2$ subcutaneously (SC) on Days 1, 4, 8, and 11 of cycles 1-8. Dexamethasone was administered orally at 20 mg on Days 1, 2, 4, 5, 8, 9, 11, and 12, for a total dose of 160 mg per cycle.

Primary Outcome Measures

Progression-free survival (PFS), defined as the time from the date of randomization to the date of disease progression or death, whichever occurred first.

Secondary Outcome Measures

Time to disease progression (TTP), the overall response rate (ORR), the proportion of patients with very good partial response (VGPR) or better, the duration of response, the time to response and overall survival (OS). TTP is defined as the time from the date of randomization to the date of first documented evidence of progression, as defined in the International Myeloma Working Group (IMWG) criteria. The Overall Response is defined a stringent complete response (sCR), complete response, very good partial response (VGPR), or partial response (PR) as per IMWG Criteria. Duration of response will be calculated from the date of initial documentation of a response to the date of first documented evidence of progressive disease, as defined in the IMWG criteria. Time to response is defined as the time from the date of first dose of study treatment to the date of the first documentation of observed response. VGPR is defined as a greater than 90% reduction in blood myeloma protein (M-protein) plus urine myeloma protein less than 100 mg per 24 hours. OS will be measured from the date of randomization to the date of the participant's death.

In addition, percentage of participants with Minimal Residual Disease (MRD) will be assessed, in participants who achieve ≥VGPR by analyzing bone marrow aspiration specimens.

Safety Assessments

Safety assessments included the evaluation of adverse events, clinical laboratory testing, vital signs, and electrocardiography. The adverse events were graded according to the National Cancer Institute Common Terminology Criteria for Adverse Events, version 4.03.

Statistics

A group sequential design with one prespecified interim analysis was used to evaluate the primary end point. The O'Brien-Fleming stopping boundary at the time of the interim analysis for the primary end point was calculated with the use of a Lan-DeMets alpha-spending function on the basis of the number of events observed at the data-cutoff date. Efficacy analyses were based on the intention-to-treat population, including all patients who underwent randomization. The secondary end points were compared between the DVd and the Vd with the use of a stratified lorank test. Hazard ratios and corresponding 95% confidence intervals were estimated with the use of a stratified Cox regression model, with treatment as the sole explanatory variable. The Kaplan-Meier method was used to estimate the distribution. A stratified Cochran-Mantel-Haenszel chi-square test was used to test between-group differences.

Interim Results at Data-Cutoff Date of Jan. 11, 2016

At the time of the data-cutoff date, 243 patients in the DVd and 237 patients in the Vd had received at least one dose of trial treatment. 74 patients in the DVd and 104 in the Vd had discontinued treatment because of progressive disease or adverse events. Patient demographic, disease and clinical characteristics in the intention-to-treat patients in the two groups are shown in Table 1. International Staging System (ISS) disease staging was derived on the basis of the combination of serum β2-microglobulin and albumin. The ISS consists of three stages: stage I, serum β2-microglobulin level lower than 3.5 mg per liter (300 nmol per liter) and albumin level of 3.5 g per deciliter or higher; stage II, neither stage I nor III; and stage III, serum β2-microglobulin of 5.5 mg per liter or higher (470 nmol per liter). Higher stages indicate more severe disease.

Efficacy

The overall response rate was 82.9% in the DVd and 63.2% in the Vd (p<0.001). Table 2 shows the summary of responses among patients who could be evaluated for response.

TABLE 1

| Characteristic | DVd (N = 251) | Vd (N = 247) |
|---|---|---|
| Age | | |
| Median (range) - yr | 64 (30-88) | 64 (33-85) |
| Distribution - no. (%) | | |
| <65 yr | 132 (52.6) | 125 (50.6) |
| 65-74 yr | 96 (38.2) | 87 (35.2) |
| ≥75 yr | 23 (9.2) | 35 (14.2) |
| Type of measurable disease - no. (%) | | |
| IgG | 125 (49.8) | 138 (55.9) |
| IgA | 56 (22.3) | 54 (21.9) |
| Other | 5 (2.0) | 4 (1.6) |
| Detected in urine only | 40 (15.9) | 36 (14.6) |

TABLE 1-continued

| Characteristic | DVd (N = 251) | Vd (N = 247) |
|---|---|---|
| Detected in serum free light-chains only | 25 (10.0) | 14 (5.7) |
| Not evaluated | 0 | 1 (0.4) |
| ISS disease staging - no. (%) | | |
| I | 98 (39.0) | 96 (38.9) |
| II | 94 (37.5) | 100 (40.5) |
| III | 59 (23.5) | 51 (20.6) |
| Cytogenetic profile - no. (%) | | |
| Standard-risk cytogenetic abnormality | 140/181 (77.3) | 137/174 (78.7) |
| High-risk cytogenetic abnormality | 41/181 (22.7) | 37/174 (21.3) |
| Del17p | 28/181 (15.5) | 21/174 (12.1) |
| t(4; 14) | 14/181 (7.7) | 15/174 (8.6) |
| t(14; 16) | 4/181 (2.2) | 5/174 (2.9) |
| Median time since initial diagnosis of multiple myeloma (range) - yr | 3.87 (0.7-20.7) | 3.72 (0.6-18.6) |
| Number of previous lines of therapy - no. (%) | | |
| 1 | 122 (48.6) | 113 (45.7) |
| 2 | 70 (27.9) | 74 (30.0) |
| 3 | 37 (14.7) | 32 (13.0) |
| >3 | 22 (8.8) | 28 (11.3) |
| Median no. of previous lines of therapy (range) | 2 (1-9) | 2 (1-10) |
| Previous autologous stem-cell transplantation - no. (%) | 156 (62.2) | 149 (60.3) |
| Previous alkylating agent therapy - no. (%) | 240 (95.6) | 224 (90.7) |
| Previous proteasome inhibitor therapy - no. (%) | 169 (67.3) | 172 (69.6) |
| Previous immunomodulatory drug therapy - no. (%) | 179 (71.3) | 198 (80.2) |
| Previous proteasome inhibitor + immunomodulatory drug therapy - no. (%) | 112 (44.6) | 129 (52.2) |
| Disease refractory to last line of therapy - no. (%) | 76 (30.3) | 85 (34.4) |

TABLE 2

| Response Category | DVd (N = 240) | Vd (N = 234) | P Value |
|---|---|---|---|
| Overall response | | | |
| No. with response | 199 | 148 | |
| Rate - % (95% CI) | 82.9 (77.5-87.5) | 63.2 (56.7-69.4) | <0.001 |
| Best overall response - no. (%) | | | |
| Complete response or better | 46 (19.2) | 21 (9.0) | 0.001 |
| Complete response | 35 (14.6) | 16 (6.8) | |
| Stringent complete response | 11 (4.6) | 5 (2.1) | |
| Very good partial response or better | 142 (59.2) | 68 (29.1) | <0.001 |
| Very good partial response | 96 (40.0) | 47 (20.1) | |
| Partial response | 57 (23.8) | 80 (34.2) | |
| Minimal response | 10 (4.2) | 20 (8.5) | |
| Stable disease | 24 (10.0) | 47 (20.1) | |
| Progressive disease | 5 (2.1) | 16 (6.8) | |
| Response could not be evaluated | 2 (0.8) | 3 (1.3) | |

P values were calculated with the use of the Cochran-Mantel-Haenszel chi-square test.

Criteria for a stringent complete response include the criteria for a complete response plus a normal free light-chain ratio and absence of clonal plasma cells as assessed by immunohistochemical or immunofluorescence analysis or by two-color-to-four-color flow cytometry.

Safety

Most patients in the DVd and the Vd had at least one adverse event after the start of treatment (98.8% and 95.4%, respectively). Higher rates of grade 3 or 4 adverse events were observed in the DVd than in the Vd (76.1% vs. 62.4%). Three of the most common grade 3 or 4 adverse events reported in the DVd and the Vd were thrombocytopenia (45.3% and 32.9%, respectively), anemia (14.4% and 16.0%, respectively), and neutropenia (12.8% and 4.2%, respectively).

The percentage of patients who discontinued treatment because of at least one adverse event was similar in the DVd and the Vd (7.4% and 9.3%, respectively). The most common adverse events (occurring in at least 1% of patients in either group) that led to treatment discontinuation were peripheral sensory neuropathy (0.4% and 2.5%, respectively) and pneumonia (1.2% and 0.4%, respectively). Adverse events that led to death were reported in 13 patients (5.3%) in the DVd and in 14 patients (5.9%) in the Vd; these events were mainly a result of the general deterioration of the patients' physical health (0.4% and 1.3%, respectively). Other adverse events leading to death that were reported in 2 or more patients in either treatment group were pneumonia (1 patient in the DVd and 2 in the Vd), ischemic stroke (2 patients and no patients, respectively), and respiratory failure (2 patients and no patients, respectively). No cases of immunogenicity were reported in the DVd, and no cases of hemolysis were reported in either treatment group. Infusion-related reactions of any grade that were associated with daratumumab were reported in 45.3% of the patients; for 98.2% of these patients, the events occurred during the first infusion. Infusion-related reactions were mostly limited to grade 1 or 2 events; at least one grade 3 event was reported in 21 patients (8.6%), and no grade 4 events were reported. The most common adverse event terms that were documented by the investigator as infusion-related reactions were dyspnea (10.7%), bronchospasm (9.1%), and cough (7.0%). Two patients discontinued treatment because of infusion-related reactions: bronchospasm in 1 patient and bronchospasm, laryngeal edema, and rash in the other patient.

Example 2. Study Design NCT02076009 (Pollux)

The purpose of this study was to assess the effects of administration of daratumumab when combined with lenalinomide and dexamethasone compared with lenalinomide and dexamethasone alone, for participants with relapsed or refractory multiple myeloma. The study was a multicenter, randomized open-label active-controlled phase 3 trial. A prespecified interim analysis has been described in Dimopoulos et al., *NEJM* 375: 1319-31, 2016. The clinical trial number for this study is NCT02076009.

Eligibility

Patients with documented progressive multiple myeloma (according to International Myeloma Working Group IMWG criteria) who had received at least one previous therapy for multiple myeloma and had at least a partial response to the at least previous therapy were eligible.

Exclusion Criteria

Patients who had received daratumumab or other anti-CD38 therapies previously, patients who were refractory to or who had unacceptable side effects from lenalinomide, patients with a neutrophil count <1000 cells/mm$^3$, hemoglobin <7.5 g/dl, platelet count <75,000/mm$^3$, creatinine clearance <20 ml/min per 1.73 m$^2$ body-surface area, alanine aminotransferase or aspartate aminotransferase level of 2.5 or more times the upper limit of the normal range, and bilirubin level of 1.5 or more times the upper limit of the normal range, or creatinine clearance of less than 30 ml per minute were excluded.

Trial Treatments

Patients were randomly assigned in a 1:1 ratio to receive daratumumab, lenalinomide and dexamethasone (DRd; "daratumumab group") or lenalinomide and dexamethasone (Rd; "control group"). Randomization was stratified by International Staging System (ISS), number of prior treatment programs (1 vs. 2 or 3 vs. >3), and prior lenalinomide treatment ("no" vs. "yes").

Daratumumab was administered as an IV infusion at a dose of 16 mg/kg weekly (on days 1, 8, 15, and 22) for 8 weeks during cycles 1 and 2, every 2 weeks (on days 1 and 15) for 16 weeks (cycles 3 through 6), and every 4 weeks thereafter. Both groups received lenalidomide at a dose of 25 mg orally on days 1 to 21 of each cycle if the creatinine clearance was more than 60 ml per minute (or a dose of 10 mg daily if the creatinine clearance was 30 to 60 ml per minute) and dexamethasone at a dose of 40 mg weekly. For the DRd, the dose of dexamethasone was split: dexamethasone was administered at a dose of 20 mg before infusion as prophylaxis for infusion-related reactions and 20 mg was administered the next day.

Primary Outcome Measures

Progression-free survival (PFS), defined as the time from the date of randomization to the date of disease progression or death, whichever occurred first.

Secondary Outcome Measures

Time to disease progression (TTP), the overall response rate (ORR), the proportion of patients with very good partial response (VGPR) or better, the duration of response, the time to response and overall survival (OS). TTP is defined as the time from the date of randomization to the date of first documented evidence of progression, as defined in the International Myeloma Working Group (IMWG) criteria. The Overall Response is defined a stringent complete response (sCR), complete response, very good partial response (VGPR) or partial response (PR) as per IMWG Criteria. Duration of response will be calculated from the date of initial documentation of a response to the date of first documented evidence of progressive disease, as defined in the IMWG criteria. Time to response is defined as the time from the date of first dose of study treatment to the date of the first documentation of observed response. VGPR is defined as a greater than 90% reduction in blood myeloma protein (M-protein) plus urine myeloma protein less than 100 mg per 24 hours. OS will be measured from the date of randomization to the date of the participant's death.

In addition, the percentage of participants with Minimal Residual Disease (MRD) will be assessed, in participants who achieve ≥VGPR by analyzing bone marrow aspiration specimens.

Statistics

A group sequential design with one prespecified interim analysis was used to evaluate the primary end point. The O'Brien-Fleming stopping boundary at the time of the interim analysis for the primary end point was calculated with the use of a Lan-DeMets alpha-spending function on the basis of the number of events observed at the data-cutoff date. Efficacy analyses were based on the intention-to-treat population, including all patients who underwent randomization. The secondary end points were compared between the DRd and the Rd with the use of a stratified lorank test. Hazard ratios and corresponding 95% confidence intervals were estimated with the use of a stratified Cox regression model, with treatment as the sole explanatory variable. The Kaplan-Meier method was used to estimate the distribution. A stratified Cochran-Mantel-Haenszel chi-square test was used to test between-group differences.

Interim Results at Data-Cutoff Mar. 7, 2016

At the time of the data-cutoff date, 286 patients in the DRd and 283 patients in the Rd had received at least one dose of trial treatment. 66 patients in the DRd and 132 in the Rd had discontinued treatment, mainly because of progressive disease or adverse events. Patient demographic, disease and clinical characteristics in the intention-to-treat patients in the two groups are shown in Table 3. International Staging System (ISS) disease staging was derived on the basis of the combination of serum β2-microglobulin and albumin. The ISS consists of three stages: stage I, serum β2-microglobulin level lower than 3.5 mg per liter (300 nmol per liter) and albumin level of 3.5 g per deciliter or higher; stage II, neither stage I nor III; and stage III, serum 32-microglobulin of 5.5 mg per liter or higher (470 nmol per liter). Higher stages indicate more severe disease.

TABLE 3

| Characteristic | DRd (N = 286) | Rd (N = 283) |
|---|---|---|
| Age | | |
| Median (range) - Yr | 65 (34-89) | 65 (42-87) |
| Distribution - no. (%) | | |
| <65 yr | 133 (46.5) | 140 (49.5) |
| 65-74 yr | 124 (43.4) | 108 (38.2) |
| ≥75 yr | 29 (10.1) | 35 (12.4) |
| Race - no. (%)† | | |
| White | 207 (72.4) | 186 (65.7) |
| Black | 5 (1.7) | 11 (3.9) |
| Asian | 54 (18.9) | 46 (16.3) |
| Other or unreported | 20 (7.0) | 40 (14.1) |
| ECOG performance-status score - no. (%)‡ | | |
| 0 | 139 (48.6) | 150 (53.0) |
| 1 or 2 | 147 (51.4) | 133 (47.0) |
| ISS disease staging - no. (%) | | |
| I | 137 (47.9) | 140 (49.5) |
| II | 93 (32.5) | 86 (30.4) |
| III | 56 (19.6) | 57 (20.1) |
| Cytogenetic profile - no. (%) | | |
| Standard-risk cytogenetic abnormality | 193/228 (84.6) | 176/211 (83.4) |
| High-risk cytogenetic abnormality | 35/228 (15.4) | 35/211 (16.6) |
| Median time since initial diagnosis of multiple myeloma (range) - yr | 3.5 (0.4-27.0) | 4.0 (0.4-21.7) |
| Median no. of previous lines of therapy (range) | 1 (1-11) | 1 (1-8) |
| Previous therapy - no. (%) | | |
| Autologous stem-cell transplant | 180 (62.9) | 180 (63.6) |
| Proteasome inhibitor | 245 (85.7) | 242 (85.5) |
| Immunomodulatory drug | 158 (55.2) | 156 (55.1) |
| Glucocorticoid | 280 (97.9) | 281 (99.3) |
| Alkylating agent | 268 (93.7) | 270 (95.4) |
| Proteasome inhibitor and immunomodulatory drug | 125 (43.7) | 125 (44.2) |
| Proteasome inhibitor, immunomodulatory drug, and alkylating agent | 118 (41.3) | 121 (42.8) |
| Bortezomib and lenalidomide | 44 (15.4) | 43 (15.2) |
| Refractory disease - no. (%) | | |
| To last line of therapy | 80 (28.0) | 76 (26.9) |
| To proteasome inhibitor only | 57 (19.9) | 46 (16.3) |
| To immunomodulatory drug only | 10 (3.5) | 11 (3.9) |
| To proteasome inhibitor and immunomodulatory drug | 7 (2.4) | 14 (4.9) |

Eastern Cooperative Oncology Group (ECOG) performance status is scored on a scale from 0 to 5, with 0 indicating no symptoms and higher scores indicating increasing disability Efficacy At a median follow-up of 13.5 months, a total of 169 events of disease progression or death (in 53 patients [18.5%] in the DRd vs. 116 [41.0%] in the Rd) were reported. The hazard ratio for disease progression or death in the DRd versus the Rd was 0.37 (95% confidence interval [CI], 0.27 to 0.52; P<0.001 by stratified log-rank test). The Kaplan-Meier rate of progression-free survival at 12 months was 83.2% (95% CI, 78.3 to 87.2) in the DRd and 60.1% (95% CI, 54.0 to 65.7) in the Rd. The median progression-free survival was not reached (95% CI; could not be estimated) in the DRd, as compared with 18.4 months (95% CI, 13.9 to could not be estimated) in the Rd. Similarly, in the time-to-event analysis of disease progression, a total of 148 events (in 44 patients [15.4%] in the DRd vs. 104 [36.7%] in the Rd) were observed (hazard ratio, 0.34; 95% CI, 0.23 to 0.48; P<0.001). The rate of progression-free survival at 12 months was 85.7% (95% CI, 80.9 to 89.4) in the DRd, as compared with 63.2% (95% CI, 57.1 to 68.8) in the Rd. Table 4 shows the summary of responses among patients who could be evaluated for response.

TABLE 4

| Response Category | DRd (N = 281) | Rd (N = 276) | P Value |
|---|---|---|---|
| Overall response | | | |
| No. with response | 261 | 211 | |
| Rate - % (95% CI) | 92.9 (89.2-95.6) | 76.4 (71.0-81.3) | <0.001 |
| Clinical benefit - no. (%) | 266 (94.7) | 237 (85.9) | |
| Best overall response - no. (%) | | | |
| Complete response or better | 121 (43.1) | 53 (19.2) | <0.001 |
| Stringent complete response | 51 (18.1) | 20 (7.2) | |
| Complete response | 70 (24.9) | 33 (12.0) | |
| Very good partial response or better | 213 (75.8) | 122 (44.2) | <0.001 |
| Very good partial response | 92 (32.7) | 69 (25.0) | |
| Partial response | 48 (17.1) | 89 (32.2) | |
| Minimal response | 5 (1.8) | 26 (9.4) | |
| Stable disease | 13 (4.6) | 33 (12.0) | |
| Progressive disease | 0 | 4 (1.4) | |
| Response could not be evaluated | 2 (0.7) | 2 (0.7) | |

P values were calculated with the use of the Cochran-Mantel-Haenszel chi-square test.
Criteria for a stringent complete response include the criteria for a complete response plus a normal free light-chain ratio and absence of clonal plasma cells as assessed by immunohistochemical or immunofluorescence analysis or by two color-to-four-color flow cytometry.

Safety

The most common adverse events of any grade during treatment (in >15% of the patients in either group) and adverse events of grade 3 or 4 (in >5% of the patients in either group) for the safety population were neutropenia, anemia, thrombocytopenia, febrile neutropenia, lymphopenia, diarrhea, fatigue, upper respiratory tract infection, constipation, cough, muscle spasms, nasopharyngitis, nausea, pyrexia, insomnia, dyspnea, back pain, vomiting, asthenia, peripheral edema, and pneumonia. Adverse events that occurred at a frequency of 10% or more in the DRd versus the Rd were neutropenia, diarrhea, upper respiratory tract infection, and cough, most of which resulted from longer exposure to treatment in the DRd. Deep-vein thrombosis was reported in 1.8% of the patients in the DRd and in 3.9% of those in the Rd. In the DRd, 51.9% of patients had neutropenia of grade 3 or 4, as compared with 37.0% of those in the Rd; thrombocytopenia of grade 3 or 4 occurred in 12.7% and 13.5% of the patients, respectively. The percentage of patients with adverse events leading to the discontinuation of treatment was similar in the two groups: 6.7% in the DRd and 7.8% in the Rd. Adverse events leading to death occurred in 11 patients (3.9%) in the DRd and in 15 (5.3%) in the Rd. The most common adverse events leading to death were acute kidney injury (in 0.4% of the patients in the DRd and in 1.1% in the Rd), septic shock (in 1.1% and 0.4%, respectively), and pneumonia (in 0.7% in each group).

The incidence of daratumumab infusion-related reactions of any grade was 47.7%, with 92% of the reactions occurring during the first infusion. These reactions were mostly of grade 1 or 2; a total of 15 patients (5.3%) had grade 3 infusion reactions, and no patient had an event of grade 4 or 5. The most common infusion-related reactions were cough (in 8.5% of the patients), dyspnea (in 8.5%), and vomiting (in 5.7%). One patient discontinued daratumumab because of a grade 3 infusion-related event, recovered, and continued to receive lenalidomide and dexamethasone treatment.

Example 3. Efficacy of Daratumumab in Combination with Lenalidomide and Dexamethasone or Bortezomib and Dexamethasone in Relapsed or Refractory Multiple Myeloma Patients (RRMM) in High-Risk Patients Methods The analysis sets included subgroup analyses of patients from the POLLUX (Example 2) and CASTOR (Example 1) trials who had received 1 to 3 prior lines of therapy (1-3 PL subgroup). Cytogenetic abnormalities were determined at the screening visit prior to randomization by fluorescence in-situ hybridization (FISH) based on local laboratory assessment. Patients with high-risk cytogenetics included those who had one or more of the following abnormalities: t(4;14)(p16;q32), t(14;16)(q32;q23), or del17p; standard-risk patients were defined as those who underwent cytogenetic testing and did not meet the high-risk criteria.

Results: Pollux

In the 1-3 PL subgroup (DRd, n=272; Rd, n=264), PFS was significantly improved with DRd vs Rd (median: not reached [NR] vs 18.4 months; HR, 0.36; 95% CI, 0.25-0.50; P<0.0001), with estimated 12-month PFS rates of 83.2% vs 60.4%, respectively. Time to progression was also significantly longer with DRd vs Rd (median: NR vs 18.4 months; HR, 0.32; 95% CI, 0.22-0.46; P<0.0001). ORR (94% vs 77%), rates of very good partial response (VGPR) or better (76% vs 45%) and complete response (CR) or better (44% vs 20%) were significantly higher with DRd vs Rd, respectively (P<0.0001 for all). Among responders, median time to VGPR or better was 2.8 months in DRd vs 2.9 months in Rd; median time to CR or better was 6.7 months vs 7.5 months, respectively.

For pts in the 1-3 PL subgroup with high-risk cytogenetics (n=33 in each treatment group), significantly longer PFS was observed in DRd vs Rd (median: NR vs 8.3 months; HR, 0.30; 95% CI, 0.14-0.67; P=0.0019). Significantly higher ORR (91% vs 69%; P=0.0267), rate of VGPR or better (73% vs 28%; P=0.0004), and rate of CR or better (36% vs 9%; P=0.0104) were achieved in pts with high-risk cytogenetic status treated with DRd vs Rd, respectively.

FIG. 1 shows the percentage subjects who are progression free and alive in each subgroup over time.

Results: Castor

Median follow-up was 7.4 months. In the 1 to 3 prior lines (1-3 PL) subgroup (DVd, n=229; Vd, n=219), PFS was significantly longer with DVd vs Vd (median: not reached [NR] vs 7.3 mo; HR, 0.39; 95% CI, 0.28-0.55; P<0.0001); estimated 12-month PFS rates were 62.2% vs 29.3%, respectively. Median time to progression (TTP) among 1-3 PL pts was NR vs 7.4 months, respectively (HR, 0.29; 95% CI, 0.20-0.43; P<0.0001). Overall response rate (ORR) was significantly higher with DVd vs Vd (84% vs 67%; P<0.0001) and was associated with higher rates of very good partial response (VGPR) or better (62% vs 32%; P<0.0001).

Among 1-3 PL pts with standard-risk cytogenetic status, PFS was significantly prolonged in DVd vs Vd (HR, 0.38; 95% CI, 0.25-0.58; P<0.0001), and estimated 12-month PFS rates were 58.7% vs 27.0%, respectively. PFS was also significantly longer in pts with high-risk cytogenetics who received DVd vs Vd (HR, 0.46; 95% CI, 0.22-0.97; P=0.0367) with estimated 12-month PFS rates of 63.2% vs 26.7%, respectively. Lastly, the rate of MRD-negative patients was significantly higher (4 fold or greater) at all evaluated thresholds ($10^{-4}$, $10^{-5}$, and $10^{-6}$) among the 1-3 PL subgroup.

Figure 2:
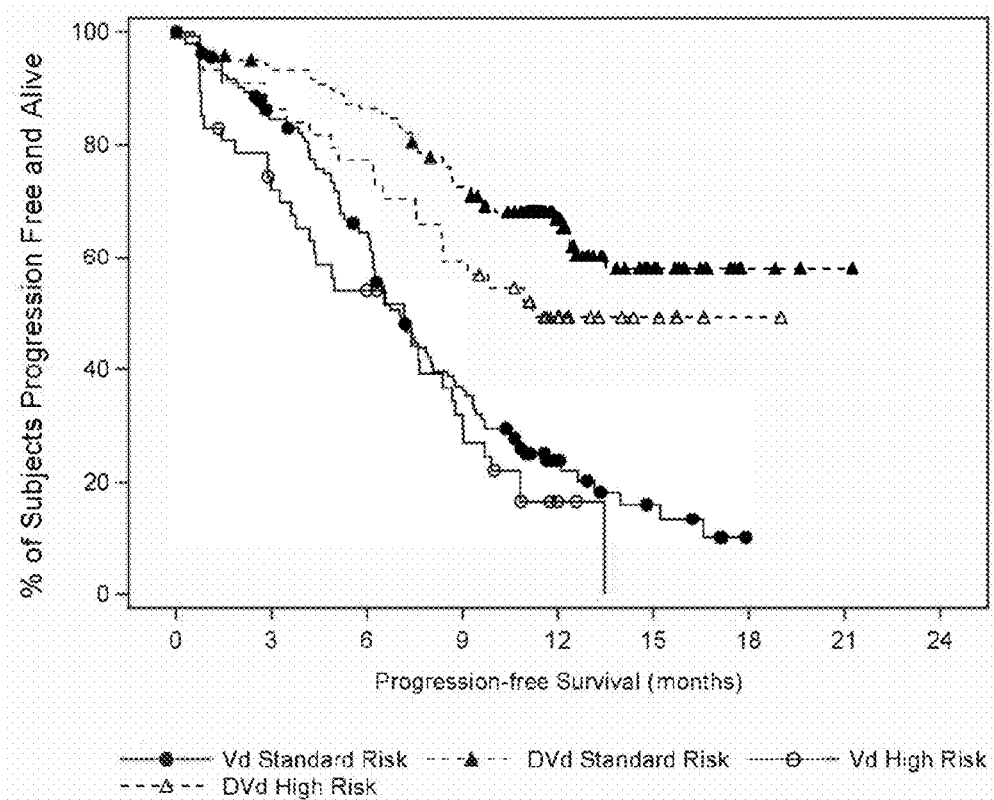
FIG. 2 illustrates a graph showing percentage (%) of multiple myeloma subjects progression free and alive by cytogenetic risk status in the CASTOR (MMY3004) trial. DVd: daratumumab in combination with bortezomib and dexamethasone; Vd: bortezomib and dexamethasone. High Risk: subject has at least one of the following chromosomal abnormalities: t(4;14)(p16;q32); t(14;16)(q32;q23); or del17p. Standard Risk: subject has documented absence of any of the aforementioned chromosomal abnormalities.

FIG. 2 shows the percentage subjects who are progression free and alive in each subgroup over time.

Conclusion

The addition of DARA to Rd significantly improved outcomes in RRMM patients with high-risk cytogenetics, and the addition of DARA to Vd showed encouraging trends towards improved PFS and response rates in these pts. Remarkably, outcomes by PFS in high risk patients treated with DRd were at least comparable to those for standard-risk patients treated with Rd alone. These results suggest that targeting CD38 in combination with Rd may help overcome the poor outcomes associated with high-risk cytogenetic status.

Example 4. MRD Analysis

MRD Sample Collection and Processing

In Study POLLUX, MRD status was assessed (blinded to treatment cohort) at the time of suspected CR, and at 3 and 6 months post-suspected CR for subjects who maintained this response. In Study CASTOR, MRD was evaluated (blinded to treatment cohort) at the time of suspected CR and for subjects who reached MRD negativity, additional analysis was done at the end of Vd background therapy (6 months after study therapy began) and finally 6 months after the end of Vd background therapy (12 months after study therapy began). The MRD assay was performed using bone marrow aspirates (BMA) and evaluated by the ClonoSEQ™ assay (Adaptive Biotechnologies, Seattle, Wash., USA). Briefly, bone marrow mononuclear cells were isolated from 2-3 mL of BMA by lymphoprep (Ficoll) separation at Covance Central Laboratory Services (Indianapolis, Ind., U.S.A; Geneva, Switzerland; Singapore) within 48 hours of collection. The cells were stored as a dry pellet at −70° C. An important note is that lymphoprep separation typically removes >95% of the granulocytes in the sample, whereas these cells are retained when the sample is processed by red blood cell (RBC) lysis. In normal bone marrow, granulocytes account for 25-50% of the cell fraction and lymphoprep separation will disproportionately reduce the total cell number in the sample analyzed. This may lead to differences in MRD negativity rates in other studies using RBC lysis since these studies have a 2-fold greater denominator and will be less stringent than the MRD determinations in Studies POLLUX and CASTOR.

Genomic DNA was isolated and amplified using a set of multiplexed, locus-specific primer sets for the IGH complete (IGH-VDJH), IGH incomplete (IGH-DJH), and immunoglobulin κ locus (IGK). The amplified product was subjected to sequencing, and the sequences and frequencies of the different clonotypes in the sample were obtained. To define myeloma clones for gene rearrangements in samples obtained at diagnosis, a frequency threshold of 5% (i.e., any clonotype present at a frequency of >5% was regarded as originating from the myeloma clone) was applied. MRD was assessed in the clinical samples with a high-frequency myeloma clone using the IGH-VDJH, and/or IGK assays as previously described (Vij R, Mazumder A, Klinger M, et al. Deep sequencing reveals myeloma cells in peripheral blood in majority of multiple myeloma patients. *Clin Lymphoma Myeloma Leuk.* 2014; 14:131-139). The myeloma-derived sequences identified at diagnosis were used as a target to assess the presence of MRD in the follow-up samples for each subject analyzed. For MRD quantitation, multiple sequencing reads were assessed for each rearranged B cell in the reaction. Once the absolute amount of total cancer-derived molecules present in a sample was determined, a final MRD measurement was calculated, providing the number of cancer-derived molecules per 1 million cell equivalents. In cases where two or more tumor clones existed, the clone with the highest MRD value was reported.

Methods for Data Analysis
Clinical Data

The input dataset from the clinical cutoff date for Study POLLUX and for Study CASTOR were used for this analysis. All the data analysis and generation of relevant graphs were performed exclusively using R software. The analysis population was the ITT population, which included all randomized subjects. Best response reported in this analysis was the best confirmed response by computerized algorithm in accordance to IMWG response and disease progression criteria.

MRD Data
MRD Data Technical Aspects

A baseline diagnostic sample from each subject was used to characterize the myeloma clone when present at a frequency of >5%. A sample failed to calibrate if a high-frequency myeloma clone could not be identified. Calibration rates of 75% and 77% in Studies POLLUX and CASTOR respectively were observed for the MRD assays using the BMA samples collected at Screening in these MM subjects (Table 5). The fact that these samples are from relapsed or refractory MM subjects could contribute to the higher calibration rates than those observed with newly diagnosed MM samples. Additionally, as these studies represent the first, prospective evaluation of MRD in a global study in relapsed or refractory MM subjects, this calibration rate may be reflective of a real world application of the technology versus in an academic research setting.

TABLE 5

| Study | Calibrates n (%) | | Fails to calibrate n (%) | | Total |
|---|---|---|---|---|---|
| POLLUX | 146 | 75.26 | 48 | 24.74 | 194 |
| CASTOR | 92 | 77.31 | 27 | 22.69 | 119 |

MRD status was to be determined at sensitivity thresholds of $10^{-4}$, $10^{-5}$, and $10^{-6}$. Importantly, a stringent criterion of cellular input equivalents of at least 10,000, 100,000, and 1,000,000, respectively, is required for determination of MRD status at each threshold. For a subset of the samples in both Studies POLLUX and CASTOR, the number of input cells did not reach the required threshold of $10^{-5}$ or $10^{-6}$ and MRD calls were therefore defined as "MRD ambiguous" and were counted as MRD positive in those samples at the threshold being evaluated (Table 6).

MRD Data Handling

The MRD status calls, total input cell equivalent, and clone count data were obtained from the clinical cut off dates. The MRD data on the individual receptors, containing the total input cell equivalent, clone count data, as well the clone frequency was provided by the vendor (Adaptive Biotechnologies) and stored in Cyberlab data repository.

Clone count and frequency provided by the vendor were calculated as:

$$\text{Clone count} = \frac{(1/\text{sensitivity threshold}) * \text{Total input cancer double stranded molecules in reaction of Follow-Up Sample}}{\text{Total input cell equivalent in Follow-Up Sample for this receptor}}$$

where the numerator represents the cancer B cell number, and the denominator the total cell number (=cancer B cells+B cells+non-B cells).

$$\text{Frequency} = \frac{\text{Total input cancer double stranded molecules in reaction of Follow-Up Sample}}{\text{Total input rearranged receptor double stranded molecules in Follow-Up Sample}} * 100,$$

where the numerator represents the cancer B cell number, and the denominator the total B cell number (=cancer B cells+B cells).

Retested sample data were summarized by averaging the frequency and summing the clone count as per instructions by the vendor.

For each MRD assessment sample, an MRD status call was determined that was either "MRD NEGATIVE," "MRD POSITIVE," or "MRD AMBIGUOUS," for each of three different sample detection limit thresholds, $10^{-4}$, $10^{-5}$ or $10^{-6}$. An "MRD NEGATIVE" test result was obtained if the number of clones detected was <1, and the number of input cells was ≥the detection limit threshold (one of $10^{-4}$, $10^{-5}$ or $10^{-6}$). An "MRD POSITIVE" test result was obtained if the number of clones detected was ≥1 or in the ITT population without MRD assessment. An "MRD AMBIGUOUS" test result was obtained if the number of clones detected was <1, but the total input cell equivalent did not reach the required sensitivity level (of either $10^{-4}$, $10^{-5}$ or $10^{-6}$).

When comparing MRD negative counts between subgroups, MRD calls were dichotomized into MRD negative or MRD positive, where MRD positive included subjects who were tested and found positive at all time points or ambiguous or were not tested.

TABLE 6

Figure 3:
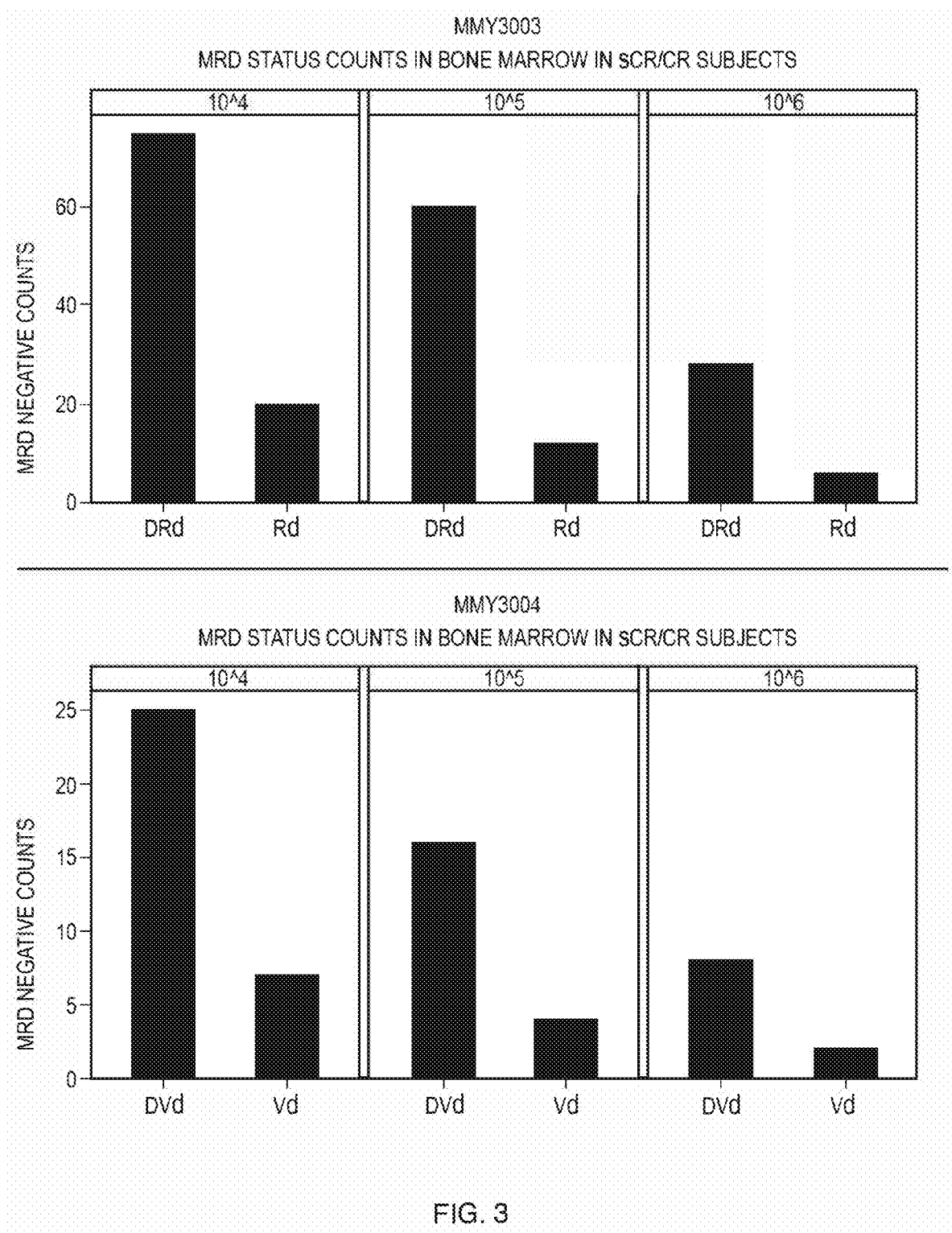
FIG. 3 illustrates the number of sCR/CR patients that reached MRD negative status in POLLUX (MMY3003, top) and CASTOR (MMY3004, bottom) trials at indicated MRD negativity thresholds.

|  |  | $10^{-4}$, n | $10^{-5}$, n | $10^{-6}$, n |
|---|---|---|---|---|
| POLLUX DRd | MRD Negative | 153 | 116 | 48 |
|  | MRD Positive | 41 | 77 | 121 |
|  | MRD Ambiguous | 0 | 1 | 25 |
| POLLUX Rd | MRD Negative | 30 | 15 | 6 |
|  | MRD Positive | 26 | 38 | 45 |
|  | MRD Ambiguous | 0 | 3 | 5 |
| CASTOR DVd | MRD Negative | 38 | 20 | 10 |
|  | MRD Positive | 29 | 46 | 55 |
|  | MRD Ambiguous | 0 | 1 | 2 |
| CASTOR Vd | MRD Negative | 9 | 6 | 2 |
|  | MRD Positive | 27 | 30 | 34 |
|  | MRD Ambiguous | 0 | 0 | 0 | studies (FIG. 3). In Study POLLUX, 75 subjects (26% of ITT) with a best confirmed clinical response of sCR or CR (38 and 37 subjects, respectively) reached MRD negative status at a threshold of $10^{-4}$ with DRd treatment. In the Rd treatment group, 20 subjects (7% of ITT) with a best confirmed clinical response of sCR or CR (10 subjects of each) reached MRD negativity at $10^{-4}$ (Table 7).

In Study CASTOR, 25 subjects (10% of ITT) with a best confirmed clinical response of sCR or CR (5 and 20 respectively) reached MRD negative status at $10^{-4}$ with DVd treatment. With Vd treatment, MRD negativity at $10^{-4}$ threshold was observed in 7 subjects (3% of ITT) with a best confirmed clinical response of sCR or CR (3 and 4 subjects, respectively) (Table 7). At $10^{-5}$ and $10^{-6}$ sensitivity thresholds in both studies, the MRD negative counts decreased. Daratumumab containing regimens consistently showed 3-fold or greater increases in MRD negativity rate compared with the control groups regardless of the background therapy.

TABLE 7

|  | MRD | DRd (sCR/CR) | Rd (sCR/CR) | DRd (sCR) | Rd (sCR) | DRd (CR) | Rd (CR) |
|---|---|---|---|---|---|---|---|
| MMY 3003 (POLLUX) | $10^{-4}$ | 75 (26.2%) | 20 (7.1%) | 38 (13%) | 10 (3.5%) | 37 (12.9%) | 10 (3.5%) |
|  | $10^{-5}$ | 60 (21%) | 12 (4.2%) | 31 (11%) | 4 (1.4%) | 29 (10.1%) | 8 (2.8%) |
|  | $10^{-6}$ | 28 (9.8%) | 6 (2.1%) | 20 (7%) | 2 (0.7%) | 8 (2.8%) | 4 (1.4%) |
|  | MRD | DVd (sCR/CR) | Vd (sCR/CR) | DVd (sCR) | Vd (sCR) | DVd (CR) | Vd (CR) |
| MMY 3004 (CASTOR) | $10^{-4}$ | 25 (10%) | 7 (2.83%) | 5 (2%) | 3 (1.2%) | 20 (8%) | 4 (1.6%) |
|  | $10^{-5}$ | 16 (6.4%) | 4 (1.62%) | 2 (0.8%) | 3 (1.2%) | 14 (5.6%) | 1 (0.4%) |
|  | $10^{-6}$ | 8 (3.2%) | 2 (0.81%) | 1 (0.4%) | 1 (0.4%) | 7 (2.8%) | 1 (0.4%) |

Results
Primary MRD Results

Briefly, for the ITT population, the DRd group demonstrated a greater incidence of MRD negativity compared with the Rd group. Twenty-nine percent (29%) of the subjects in the DRd group achieved MRD negativity status at the threshold of $10^{-4}$ versus 7.8% in the Rd group (Mantel-Haenszel Odds Ratio=4.88; 95% CI: 2.94, 8.08; p=<0.0001). Similarly, for Study CASTOR, subjects treated with DVd demonstrated a greater incidence of MRD negativity (14%) compared with 3% of subjects treated with Vd (Mantel-Haenszel Odds Ratio Estimate=5.56; 95% CI: 2.37, 13.04; p=<0.0001). As an exploratory analysis, MRD rates were also evaluated at two more stringent thresholds, $10^{-5}$ and $10^{-6}$. In Study POLLUX, the MRD negativity rate was significantly higher for subjects in the DRd group compared with subjects in the Rd at both lower thresholds. In Study CASTOR, DVd had increased MRD negative rates at both lower thresholds compared to Vd, but was significant only at $10^{-5}$ threshold.

Overall Best Confirmed Response Call and MRD Status

A statistically significant improvement in responses were observed for subjects treated with DRd compared with those treated with Rd in Study POLLUX, and for subjects treated with DVd compared with those treated with Vd in Study CASTOR.

In addition to a higher ORR in the daratumumab combination groups in Studies POLLUX and CASTOR (data not shown), a higher incidence of MRD negative status was detected in the daratumumab combination groups in both Minimal Residual Disease Over Time In Study POLLUX, MRD assessment was performed (blinded to treatment cohort) at the time of suspected CR, and at 3 and 6 months post-suspected CR for subjects who maintained this response. In Study CASTOR, MRD was evaluated for subjects at the time of suspected CR (blinded to treatment cohort) at the end of Vd background therapy (six months after study start) and 6 months after the end of Vd background therapy (12 months after study start) in the ITT population. The MRD assessment over time enabled investigation of depth and duration of MRD response in relation to the clinical response (data not shown).

As in both studies, MRD was assessed in subjects with suspected CR, the MRD negative status in these treatment groups was observed to coincide with the clinical response change to CR or sCR for majority of the subjects. Bone marrow samples from a limited number of subjects with clinical responses of partial response (PR), stable disease (SD), or minimal response (MR) were inadvertently shipped for MRD analysis which was intended for subjects with a response of ≥VGPR. As expected, these subjects tested MRD positive, with the exception of 1 sample from one subject in each of the daratumumab combination groups (DRd and DVd).

The single subject in Study POLLUX who showed MRD negative status, but best clinical response of <VGPR suffered from a baseline plasmacytoma, that achieved a maximum reduction of 36%. The best response was MR by the central algorithm despite a VGPR response evaluated by the investigator (data not shown). At lower thresholds for MRD negativity ($10^{-s}$ and $10^{-6}$), this subject was MRD positive (data not shown).

Further assessment of the single subject in Study CASTOR who achieved MRD negativity status revealed that, although the index clone identified at screening was reduced to MRD negative status (81.9% to 0.4% of the bone marrow cells), an unrelated myeloma clone present at low level at screening became dominant (7%) at the time of testing. This offers an explanation as to why the subject had progressive disease as the current response by the investigator and central algorithm, yet is counted as being MRD negative at the hierarchical threshold of $10^{-4}$ (data not shown). At lower thresholds for MRD negativity ($10^{-5}$ and $10^{-6}$), this subject was MRD positive (data not shown).

MRD Status and Progression Free Survival

Figure 4A:
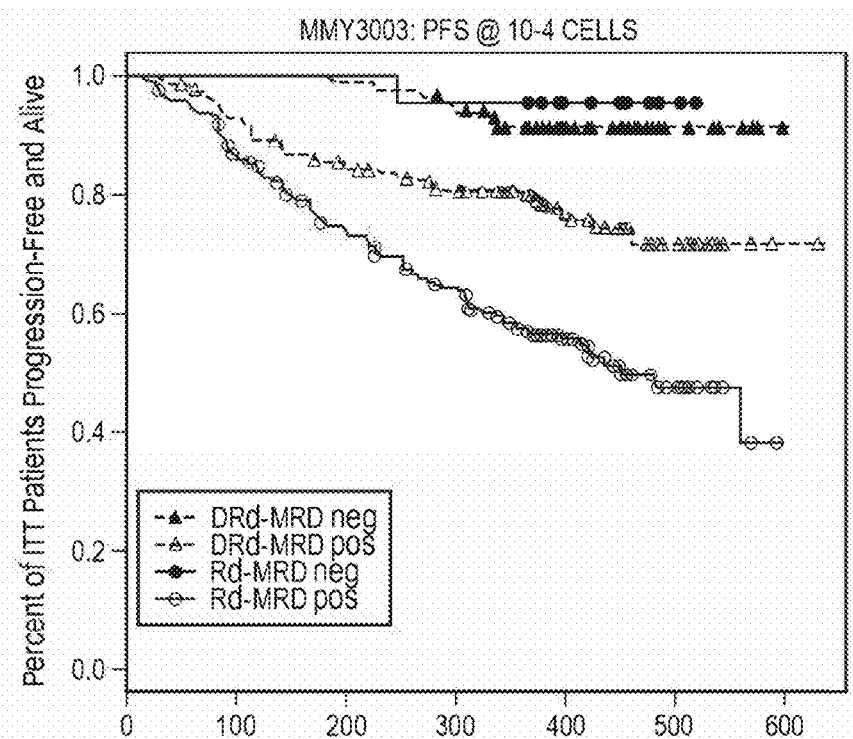
FIG. 4A illustrates a graph showing percentage (%) of multiple myeloma subjects progression free and alive over time (days) for the POLLUX (MMY3003) trial by MRD negativity at $10^{-4}$ threshold in DRd and Rd treatment arms.
Figure 4B:
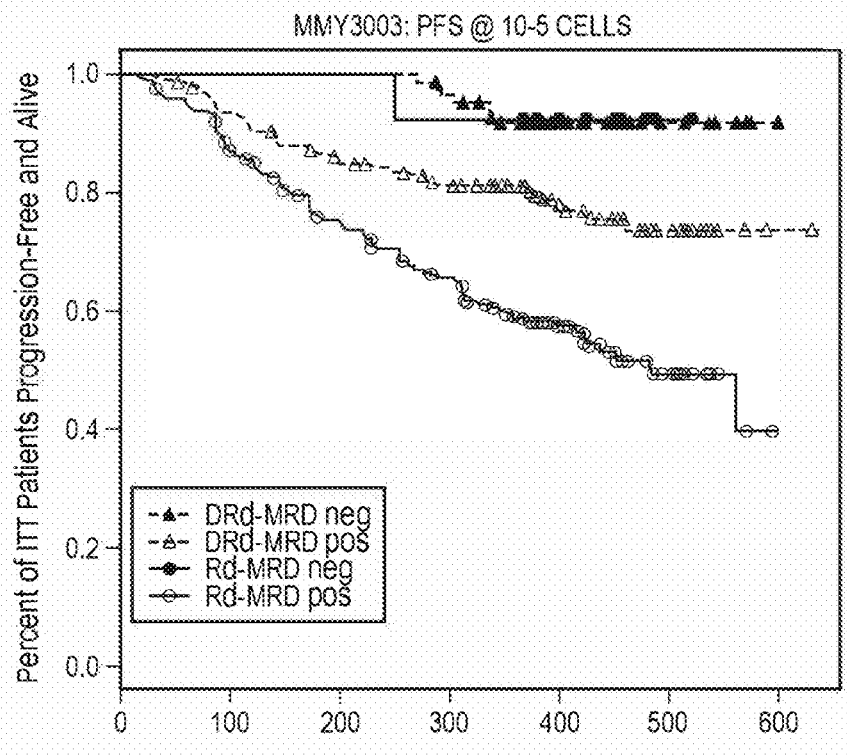
FIG. 4B illustrates a graph showing percentage (%) of multiple myeloma subjects progression free and alive over time (days) for the POLLUX (MMY3003) trial by MRD negativity at $10^{-5}$ threshold in DRd and Rd treatment arms.
Figure 4C:
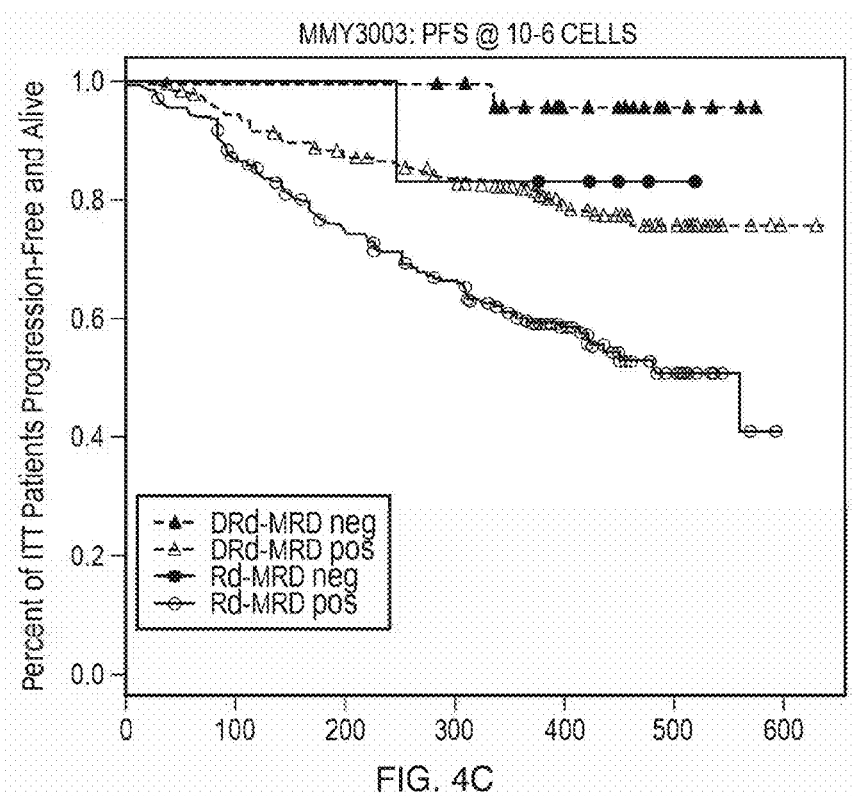
FIG. 4C illustrates a graph showing percentage (%) of multiple myeloma subjects progression free and alive over time (days) for the POLLUX (MMY3003) trial by MRD negativity at $10^{-6}$ threshold in DRd and Rd treatment arms.
Figure 5A:
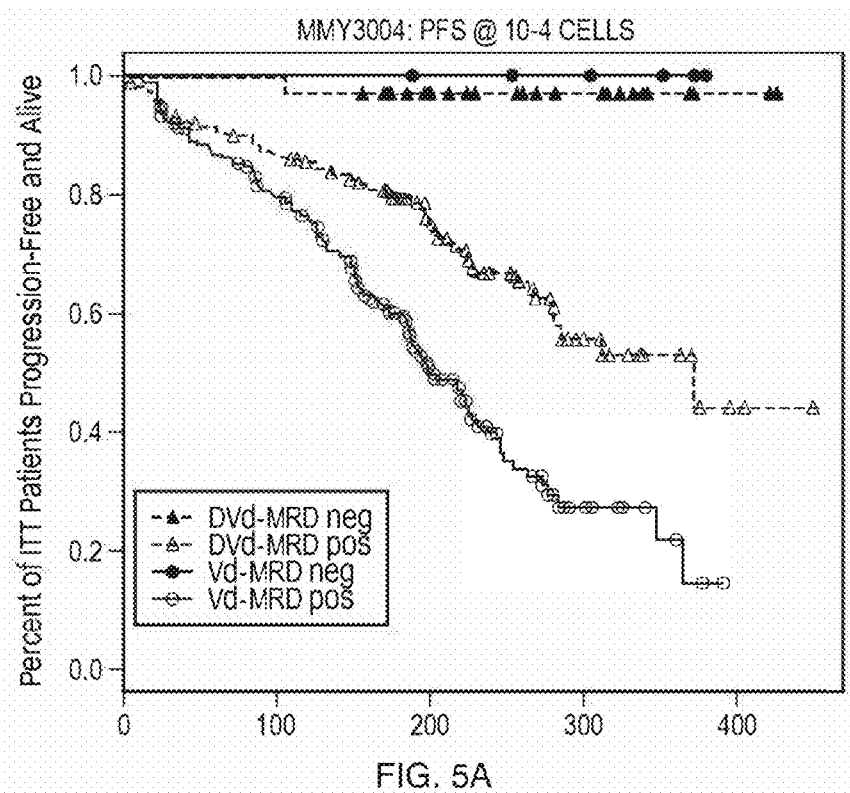
FIG. 5A illustrates a graph showing percentage (%) of multiple myeloma subjects progression free and alive over time (days) for the CASTOR (MMY3004) trial by MRD negativity at $10^{-4}$ threshold in DVd and Vd treatment arms.
Figure 5B:
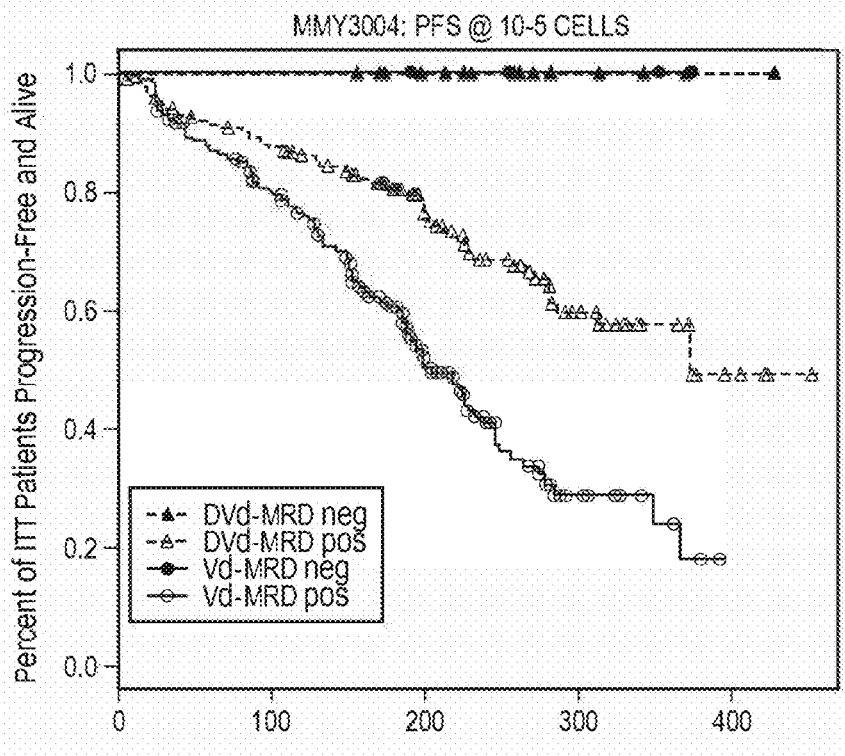
FIG. 5B illustrates a graph showing percentage (%) of multiple myeloma subjects progression free and alive over time (days) for the CASTOR (MMY3004) trial by MRD negativity at $10^{-5}$ threshold in DVd and Vd treatment arms.
Figure 5C:
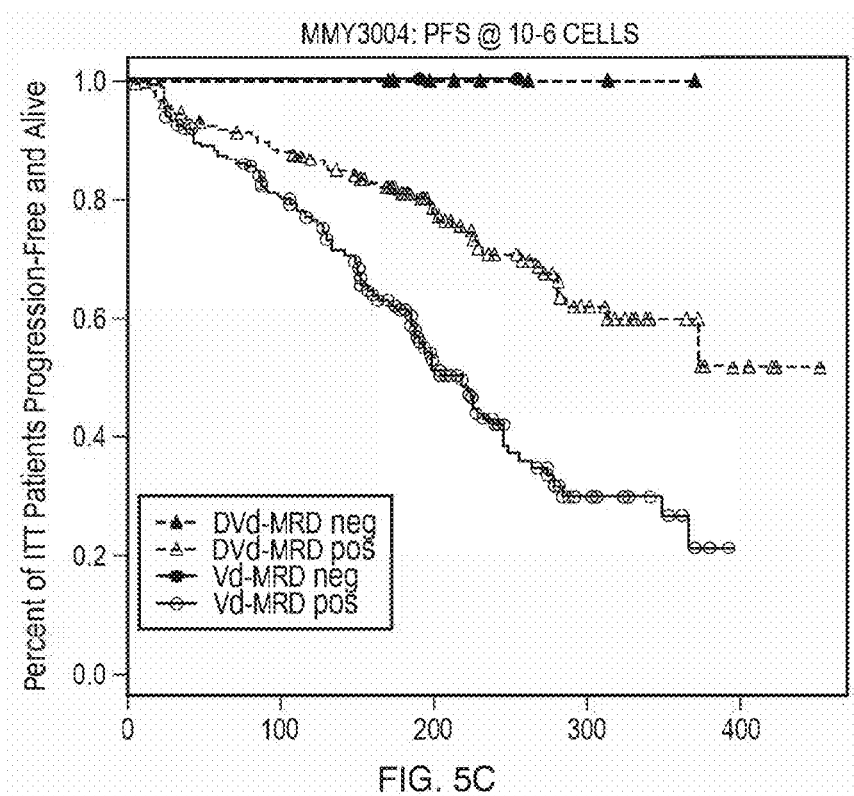
FIG. 5C illustrates a graph showing percentage (%) of multiple myeloma subjects progression free and alive over time (days) for the CASTOR (MMY3004) trial by MRD negativity at $10^{-6}$ threshold in DVd and Vd treatment arms.

Subjects who achieved MRD negative status in either of the treatment groups experienced fewer PFS events compared with MRD positive subjects, at all three thresholds tested (FIG. 4A, FIG. 4B and FIG. 4C for POLLUX, FIG. 5A, FIG. 5B and FIG. 5C for CASTOR). Of the subjects who remain MRD positive, improved PFS was observed in the daratumumab combination group compared to standard of care regimens, Rd and Vd, in both studies.

MRD Status and Prior Lines of Therapy

In Study POLLUX, at $10^{-4}$, MRD negative status was reached in subjects treated with DRd with up to 4 prior lines of therapy, with the highest rate in subjects who received one prior line (n=41, 14.3% ITT, Table 8). With Rd treatment, MRD negative status was reached at a lower rate for each of the prior lines, with subjects receiving 1 or 2 prior lines and only 2 subjects (0.7% ITT) receiving 4+ prior lines of therapy. No subjects with 3 prior lines of therapy reached MRD negative status. A similar pattern was observed for detection thresholds $10^{-5}$ and $10^{-6}$.

In Study CASTOR, at $10^{-4}$, the highest MRD negative rate was reached with DVd treatment (n=20, 8%). Subjects with 2 or 3 prior lines of therapy showed a lower MRD negativity rate (n=10, 4% and n=4, 1.6% of ITT, respectively). In the Vd treatment group, only subjects with 1 or 2 prior lines of therapy reached MRD negative status (n=4, 1.6% and 3, 1.2%, respectively). Similar trends were observed for $10^{-5}$. At $10^{-6}$, no subjects with 3+ prior lines of therapy in the DVd treatment group and 2+ prior lines of therapy in the Vd treatment group reached MRD negative state.

TABLE 8

| | MRD | Prior lines of therapy | DRd-MRD neg | Rd-MRD neg | DRd-MRD pos | Rd-MRD pos |
|---|---|---|---|---|---|---|
| MMY 3003 (POLLUX) | $10^{-4}$ | 1 | 41 (14.3%) | 14 (4.9%) | 108 (37.8%) | 132 (46.6%) |
| | | 2 | 32 (11.2%) | 6 (2.1%) | 53 (18.5%) | 74 (26.1%) |
| | | 3 | 8 (2.8%) | 0 (0%) | 30 (10.5%) | 38 (13.4%) |
| | | 4+ | 2 (0.7%) | 2 (0.7%) | 12 (4.2%) | 17 (6%) |
| | $10^{-5}$ | 1 | 31 (10.8%) | 9 (3.2%) | 118 (41.3%) | 137 (48.4%) |
| | | 2 | 24 (8.4%) | 4 (1.4%) | 61 (21.3%) | 76 (26.9%) |
| | | 3 | 7 (2.4%) | 0 (0%) | 31 (10.8%) | 38 (13.4%) |
| | | 4+ | 2 (0.7%) | 0 (0%) | 12 (4.2%) | 19 (6.7%) |
| | $10^{-6}$ | 1 | 12 (4.2%) | 5 (1.8%) | 137 (47.9%) | 141 (49.8%) |
| | | 2 | 12 (4.2%) | 1 (0.4%) | 73 (25.5%) | 79 (27.9%) |
| | | 3 | 2 (0.7%) | 0 (0%) | 36 (12.6%) | 38 (13.4%) |
| | | 4+ | 2 (0.7%) | 0 (0%) | 12 (4.2%) | 19 (6.7%) |

| | MRD | Prior lines of therapy | DVd-MRD neg | Vd-MRD neg | DVd-MRD pos | Vd-MRD pos |
|---|---|---|---|---|---|---|
| MMY 3004 (CASTOR) | $10^{-4}$ | 1 | 20 (8%) | 4 (1.6%) | 102 (40.6%) | 109 (44.1%) |
| | | 2 | 10 (4%) | 3 (1.2%) | 60 (23.9%) | 71 (28.7%) |
| | | 3 | 4 (1.6%) | 0 (0%) | 33 (13.1%) | 32 (13%) |
| | | 4+ | 0 (0%) | 0 (0%) | 22 (8.8%) | 28 (11.3%) |
| | $10^{-5}$ | 1 | 10 (4%) | 3 (1.2%) | 112 (44.6%) | 110 (44.5%) |
| | | 2 | 6 (2.4%) | 1 (0.4%) | 64 (25.5%) | 73 (29.6%) |
| | | 3 | 2 (0.8%) | 0 (0%) | 35 (13.9%) | 32 (13%) |
| | | 4+ | 0 (0%) | 0 (0%) | 22 (8.8%) | 28 (11.3%) |
| | $10^{-6}$ | 1 | 5 (2%) | 2 (0.8%) | 117 (46.6%) | 111 (44.9%) |
| | | 2 | 4 (1.6%) | 0 (0%) | 66 (26.3%) | 74 (30%) |
| | | 3 | 0 (0%) | 0 (0%) | 37 (14.7%) | 32 (13%) |
| | | 4+ | 0 (0%) | 0 (0%) | 22 (8.8%) | 28 (11.3%) |

MRD Case Study Examples

A number of MRD case study examples were identified from these studies that showed that the ClonoSEQ' assay can be used to investigate how individual tumor clone sequences behave upon treatment in individual subjects.

MRD Negative Responders with Maintained MRD Negative Status

Figure 6A:
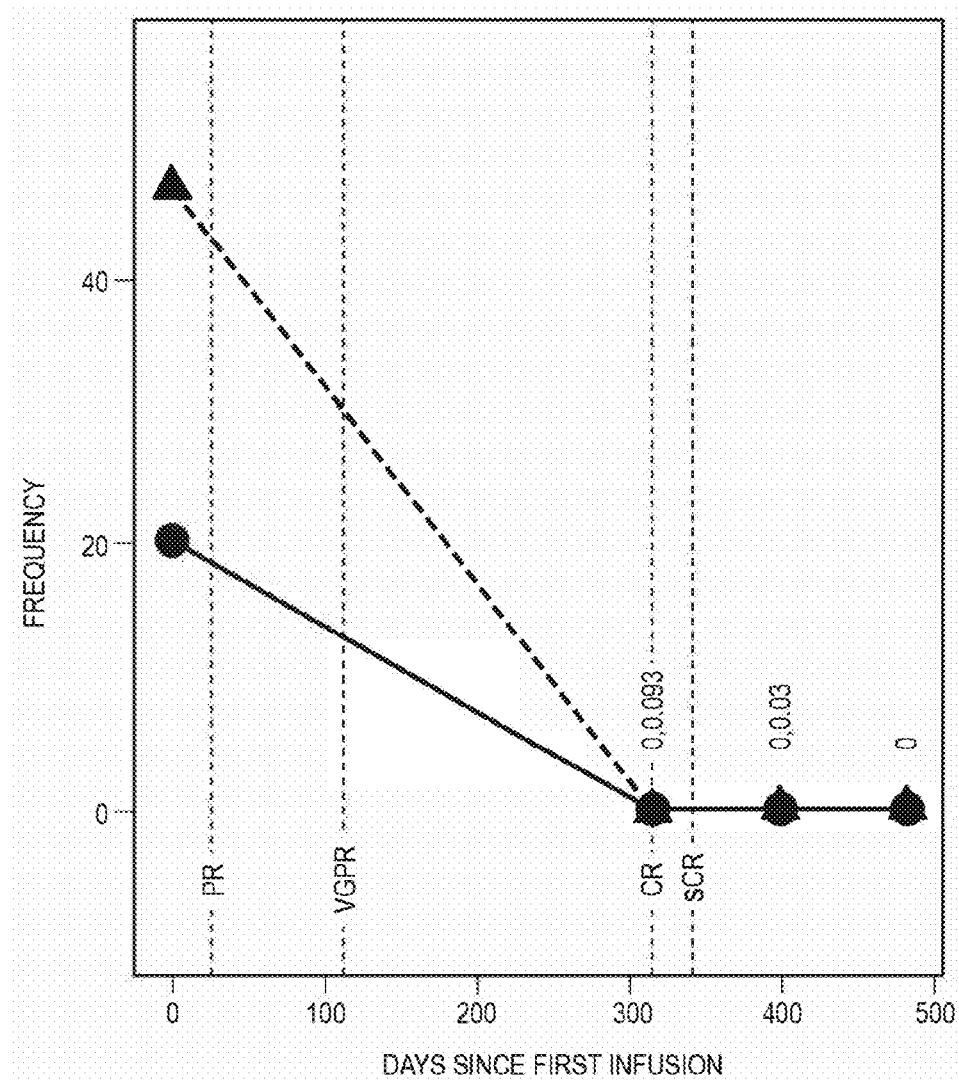
FIG. 6A illustrates a MRD profile of a responder who was MRD negative status (threshold $10^{-5}$) at suspected CR and remained MRD negative after CR. Malignant clone frequency at baseline (x=0) and over time is shown. The numbers vertically in black printed for each MRD sample show the MRD clone counts. The vertical dotted lines show the clinical response call for that subject, with the label printed at the bottom. Two distinct malignant clones (triangles and circles) were identified in the patient. The subject was MRD positive at baseline and MRD negative at and after suspected CR.
Figure 6B:
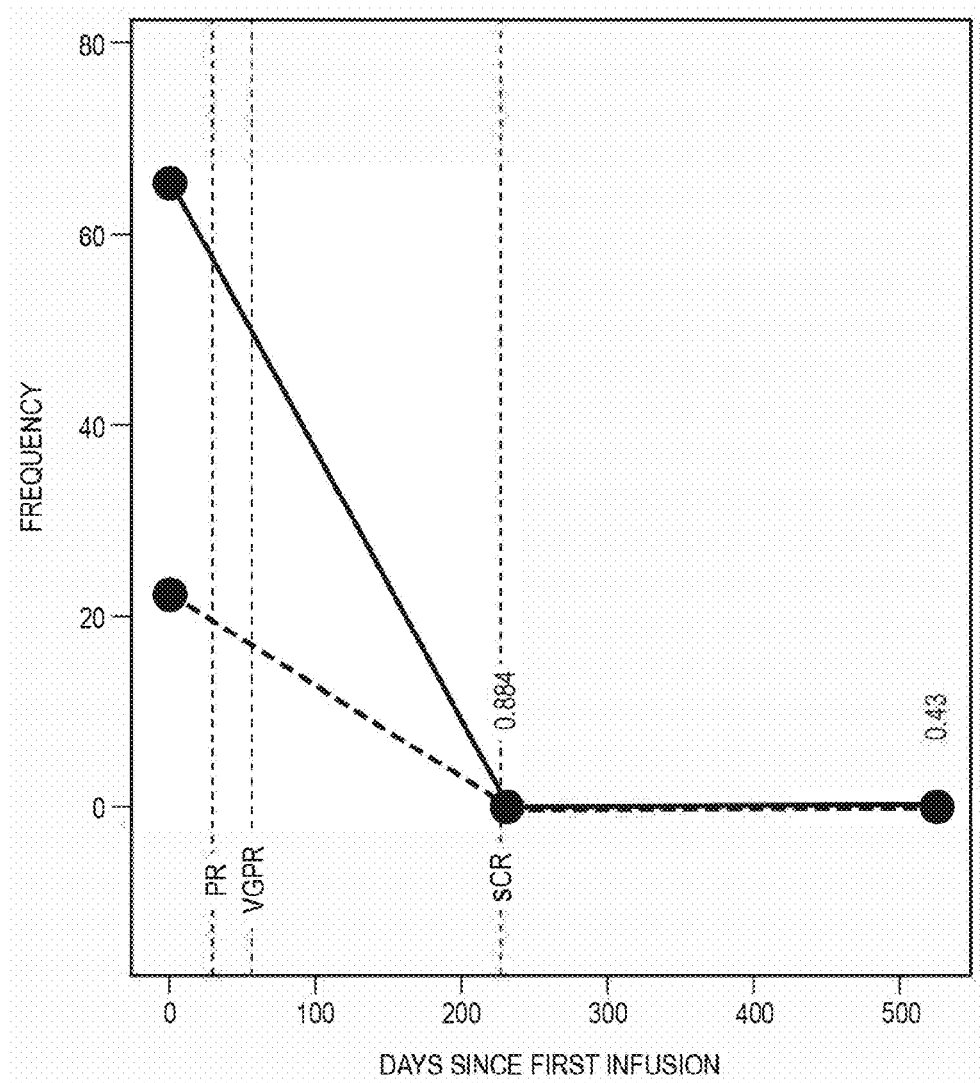
FIG. 6B illustrates a MRD profile of a responder who was MRD negative status (threshold $10^{-5}$) at suspected sCR and remained MRD negative after sCR. Malignant clone frequency at baseline (x=0) and over time is shown. The numbers vertically in black printed for each MRD sample show the MRD clone counts. The vertical dotted lines show the clinical response call for that subject, with the label printed at the bottom. Two distinct tumor clones (solid lines and dashed lines) were identified in the patient. The subject was MRD positive at baseline and MRD negative at and after suspected sCR.
Figure 7A:
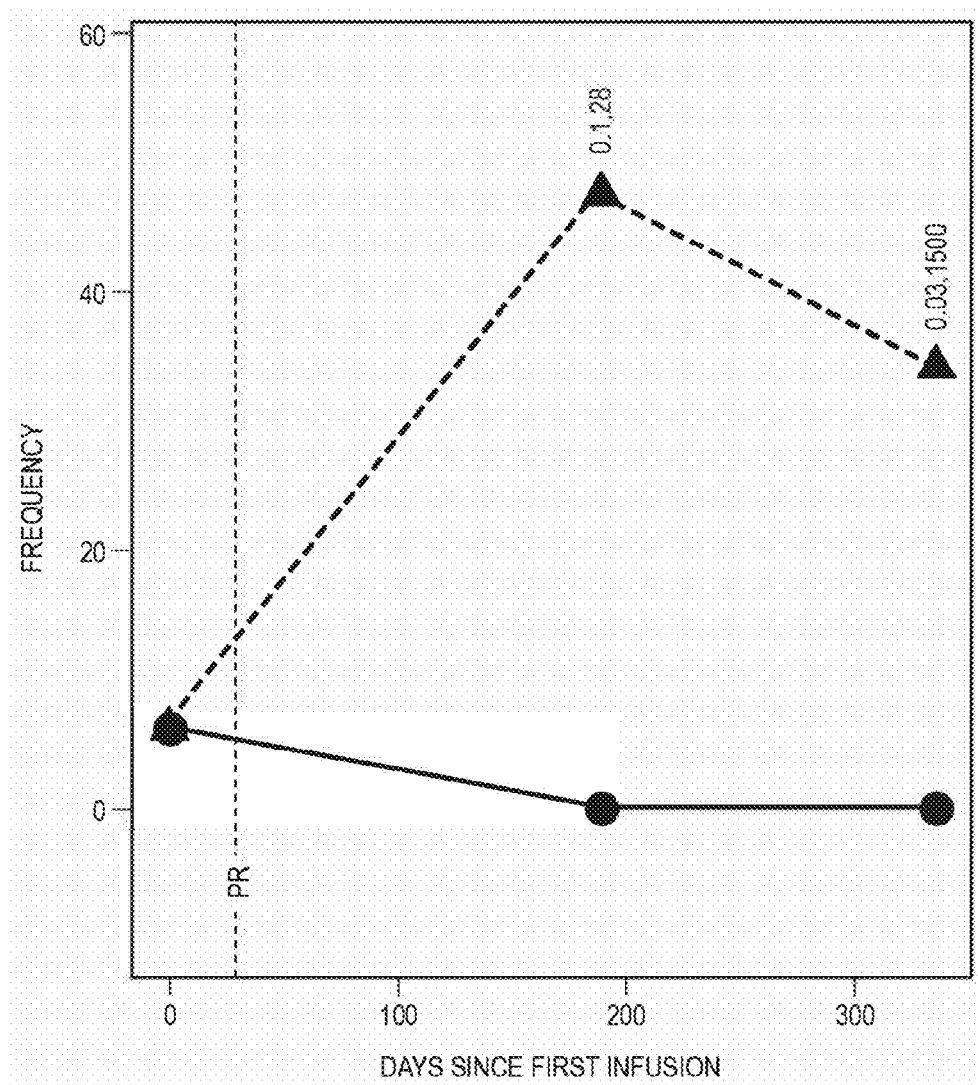
FIG. 7A illustrates a MRD profile of a non-responder over time. Malignant clone frequency at baseline (x=0) and over time is shown. The vertical dotted lines show the clinical response call for that subject, with the label printed at the bottom. Two distinct tumor clones (solid lines and dashed lines) were identified in the patient. The subject was MRD positive at each evaluation point (threshold $10^{-5}$).
Figure 7B:
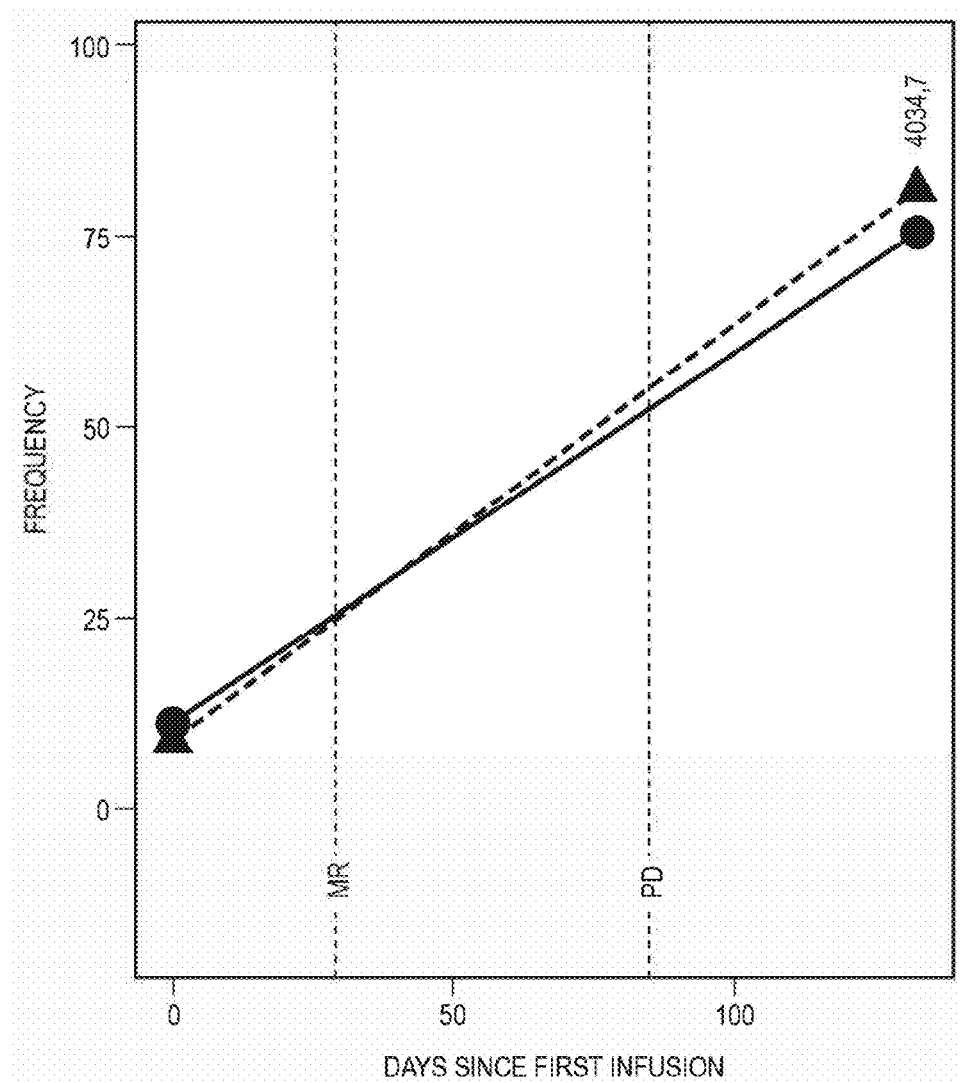
FIG. 7B illustrates a MRD profile of a non-responder over time. Malignant clone frequency at baseline (x=0) and over time is shown. The vertical dotted lines show the clinical response call for that subject, with the label printed at the bottom. Two distinct tumor clones (solid lines and dashed lines) were identified in the patient. The subject was MRD positive at each evaluation point (threshold $10^{-5}$).
Figure 7C:
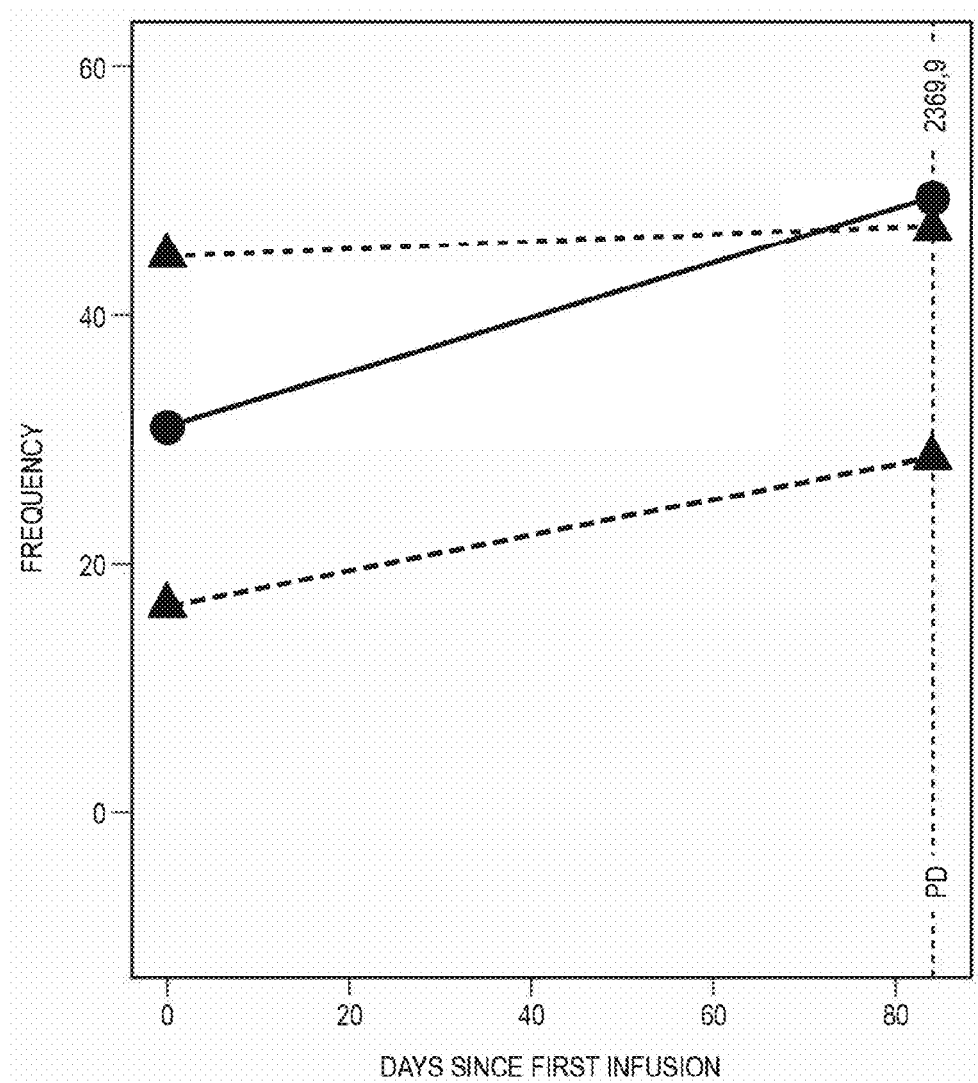
FIG. 7C illustrates a MRD profile of a non-responder over time. Malignant clone frequency at baseline (x=0) and over time is shown. The vertical dotted lines show the clinical response call for that subject, with the label printed at the bottom. Two distinct tumor clones (solid lines and dashed lines) were identified in the patient. The subject was MRD positive at each evaluation point (threshold $10^{-5}$).
Figure 7D:
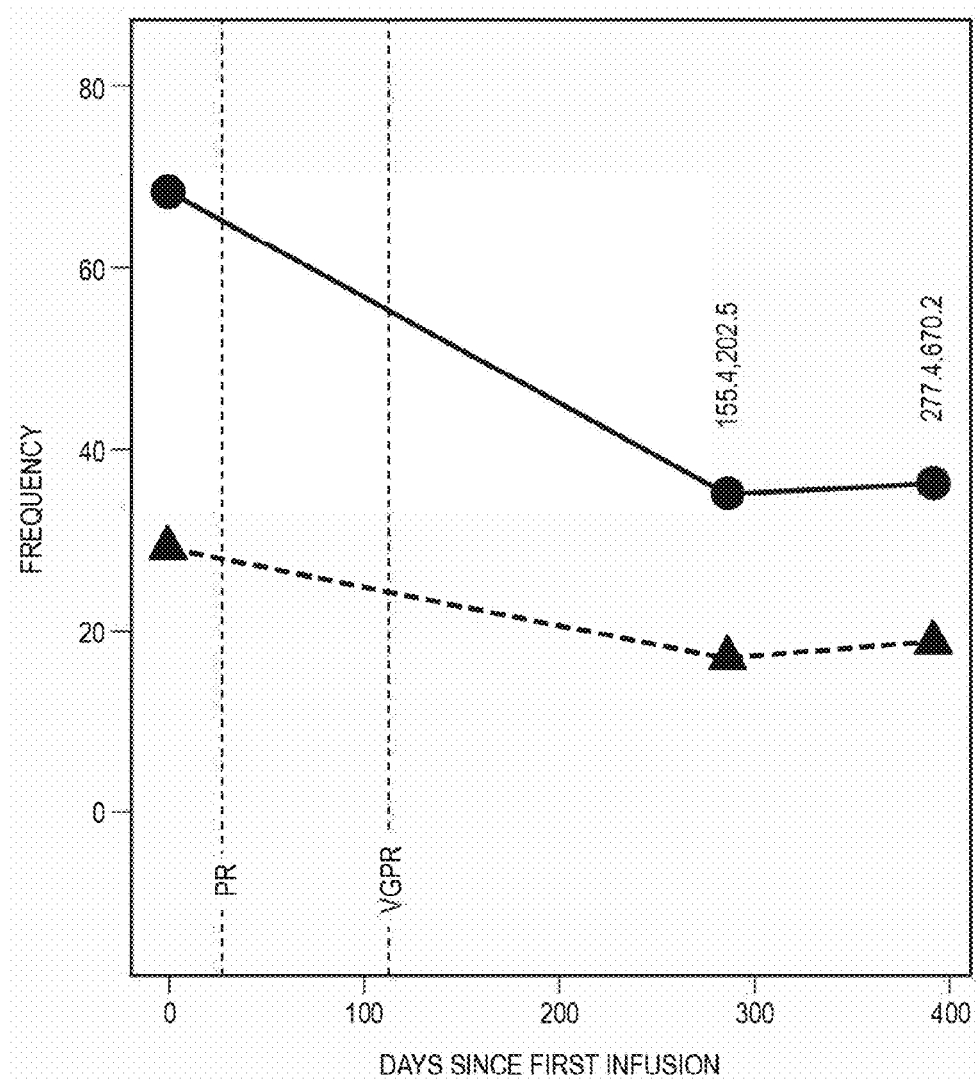
FIG. 7D illustrates a MRD profile of a non-responder over time. Malignant clone frequency at baseline (x=0) and over time is shown. The vertical dotted lines show the clinical response call for that subject, with the label printed at the bottom. Two distinct tumor clones (solid lines and dashed lines) were identified in the patient. The subject was MRD positive at each evaluation point (threshold $10^{-5}$).

In Study POLLUX, MRD was assessed at multiple time points upon treatment, i.e., at the time of suspected CR, and at 3 and 6 months post-suspected CR for subjects who maintained this response. A large number of subjects (majority of which were in the DRd group), reached MRD negative state at a time of suspected complete response and maintained it over time. FIG. 6A and FIG. 6B show the MRD profiles of two such subjects.

MRD Positivity in Partial and Non-Responders

A limited number of samples of subjects with clinical responses of PR, SD, or MR were inadvertently shipped for MRD analysis, which was only intended for subjects with a response of ≥VGPR. As expected clinically, in these as well as in other subjects that can be identified, the MRD negative status was not reached and their clone receptor frequency remained high. FIG. 7A, FIG. 7B, FIG. 7C and FIG. 7D show the MRD profiles of four such subjects.

MRD at Treatment Relapse

Figure 8A:
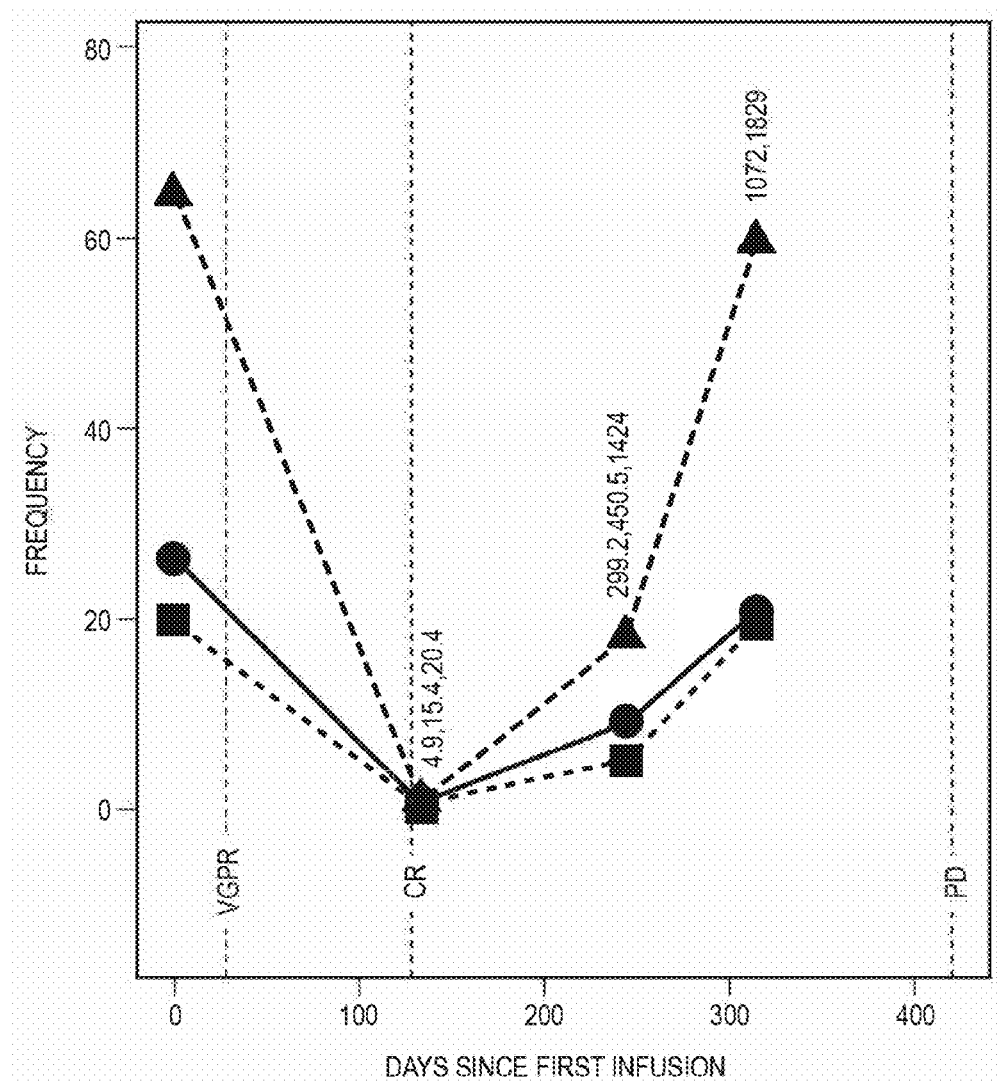
FIG. 8A illustrates a MRD profile of a subject who initially showed clinical response after which the subject experienced progressive disease. Malignant clone frequency at baseline (x=0) and over time is shown. The vertical dotted lines show the clinical response call for that subject, with the label printed at the bottom. Three distinct tumor clones (solid lines, dashed lines and dotted lines) were identified in the patient. The subject was MRD positive at each evaluation point (threshold $10^{-5}$).
Figure 8B:
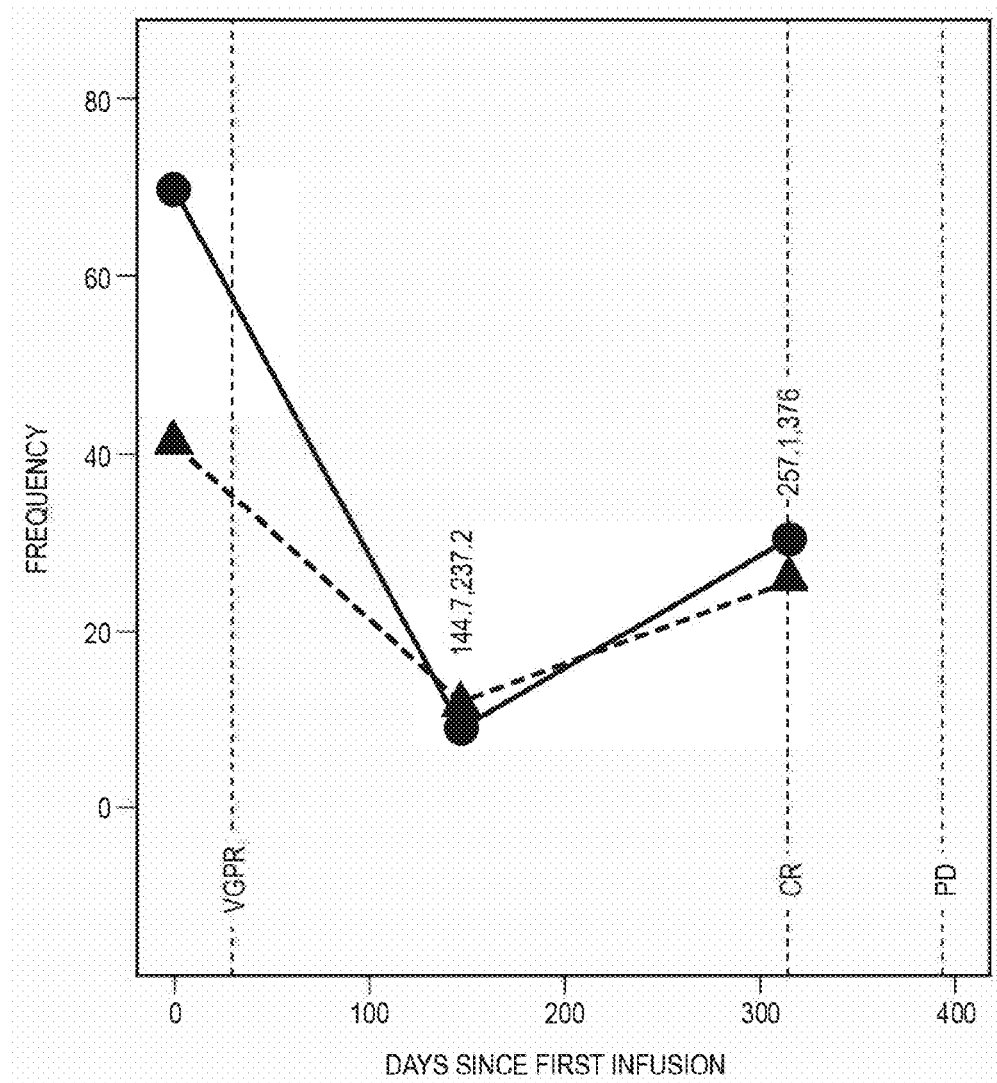
FIG. 8B illustrates a MRD profile of a subject who initially showed clinical response after which the subject experienced progressive disease. Malignant clone frequency at baseline (x=0) and over time is shown. The vertical dotted lines show the clinical response call for that subject, with the label printed at the bottom. Two distinct tumor clones (solid lines and dashed lines) were identified in the patient. The subject was MRD positive at each evaluation point (threshold $10^{-5}$).

Clonal response and then expansion was observed in some subjects who initially showed clinical response, after which they experienced progressive disease. FIG. 8A and FIG. 8B show the MRD profiles of two such subjects. In these subjects, the MRD diagnostic clone was decreased at time of CR, after which the clone frequency increased, and progressive disease was later clinically detected. These cases suggest that MRD testing could be used as a sensitive measure of disease response, including an early sign of relapse and progression.

Response Depth Increases

Figure 9A:
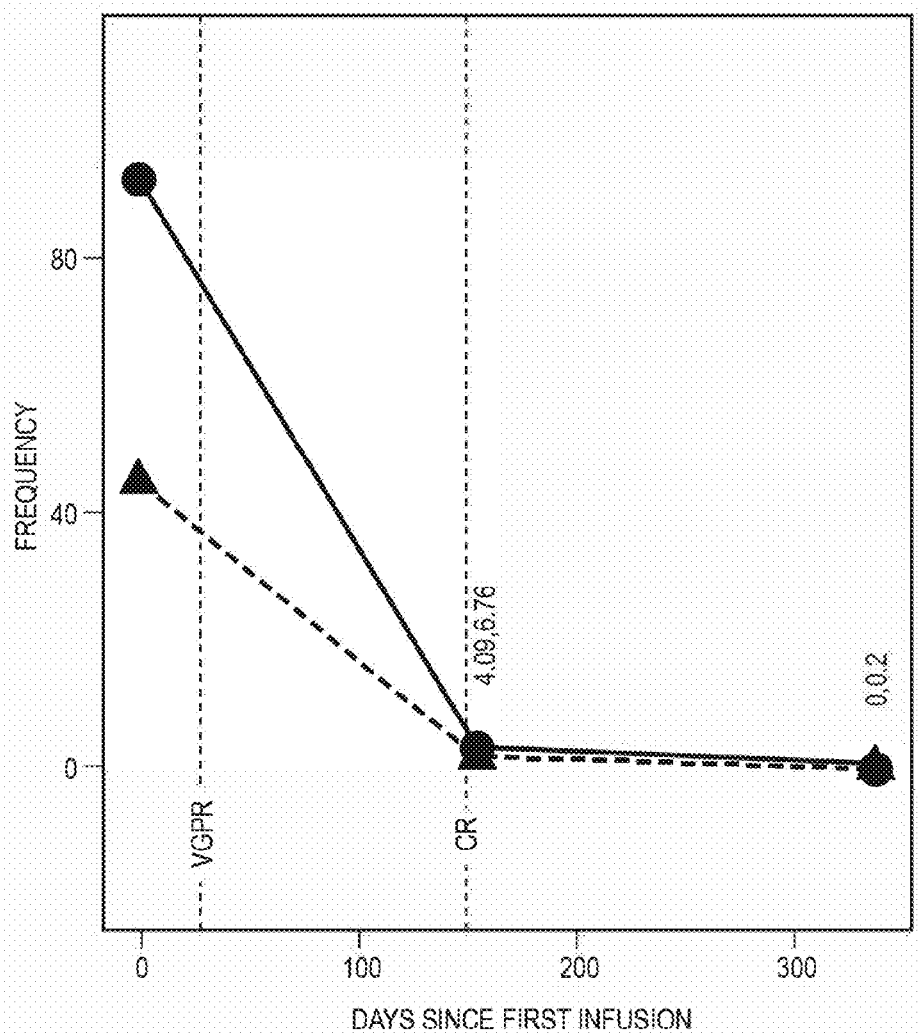
FIG. 9A illustrates a MRD profile of a subject who showed rapid clinical response but reached MRD negativity only after suspected CR. Malignant clone frequency at baseline (x=0) and over time is shown. The vertical dotted lines show the clinical response call for that subject, with the label printed at the bottom. Two distinct tumor clones (solid lines and dashed lines) were identified in the patient. The subject was MRD positive at baseline and at suspected CR, and MRD negative at approximately 340 days after initiation of the treatment (threshold $10^{-5}$).
Figure 9B:
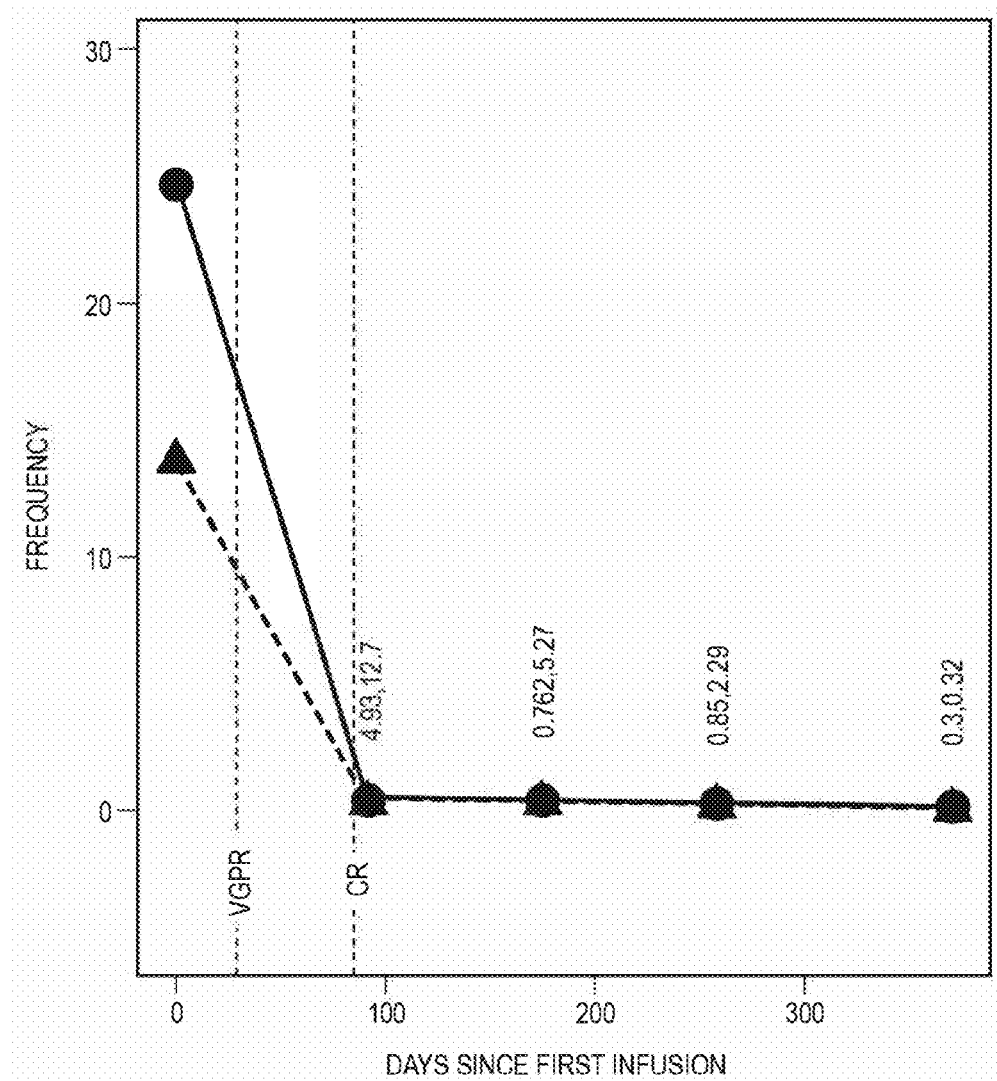
FIG. 9B illustrates a MRD profile of a subject who showed rapid clinical response but reached MRD negativity only after suspected CR. Malignant clone frequency at baseline (x=0) and over time is shown. The vertical dotted lines show the clinical response call for that subject, with the label printed at the bottom. Two distinct tumor clones (solid lines and dashed lines) were identified in the patient. The subject was MRD positive at baseline, at suspected CR, at approximately 170 days and 260 days after initiation of the treatment, and MRD negative at approximately 360 days after initiation of the treatment (threshold $10^{-5}$).
Figure 10A:
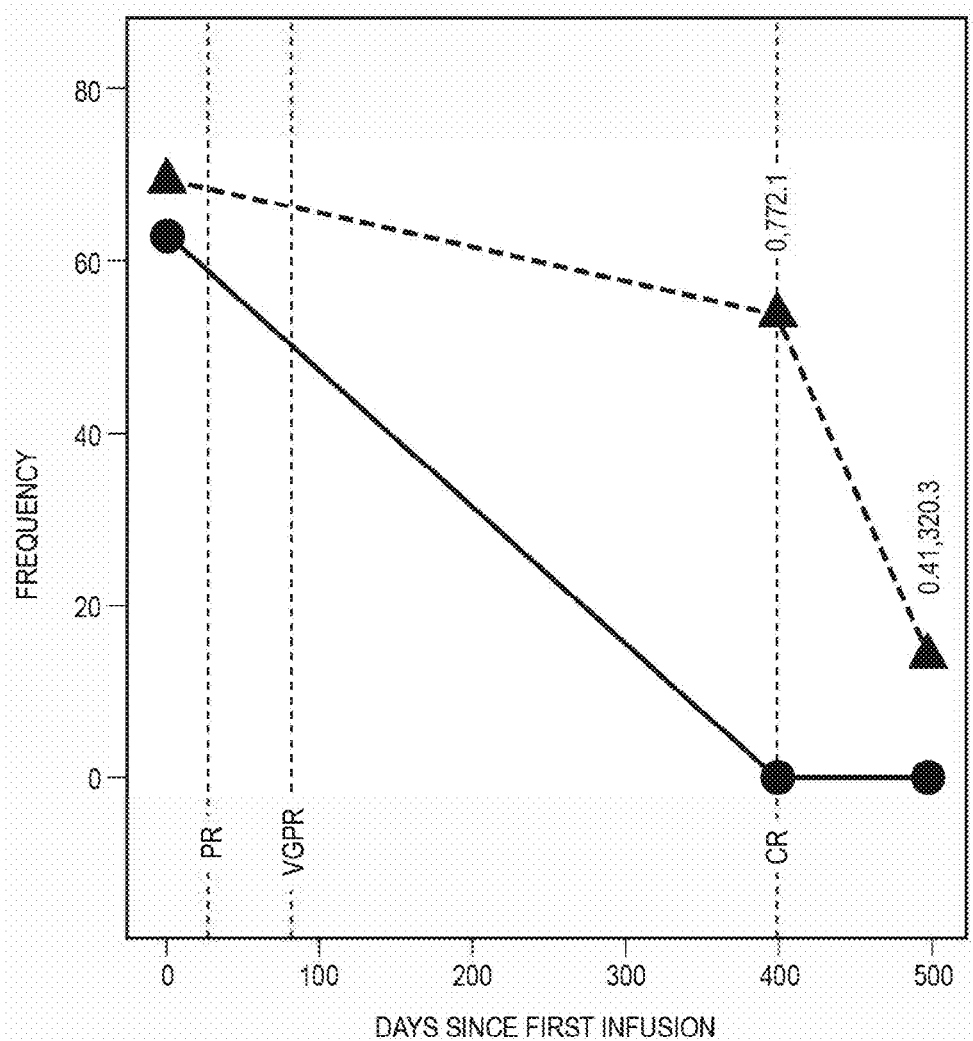
FIG. 10A illustrates a MRD profile of a subject who showed slow clinical response and remained MRD positive after suspected CR. Malignant clone frequency at baseline (x=0) and over time is shown. The vertical dotted lines show the clinical response call for that subject, with the label printed at the bottom. Two distinct tumor clones (solid lines and dashed lines) were identified in the patient. The subject was MRD positive at each evaluation point (threshold $10^{-5}$).
Figure 10B:
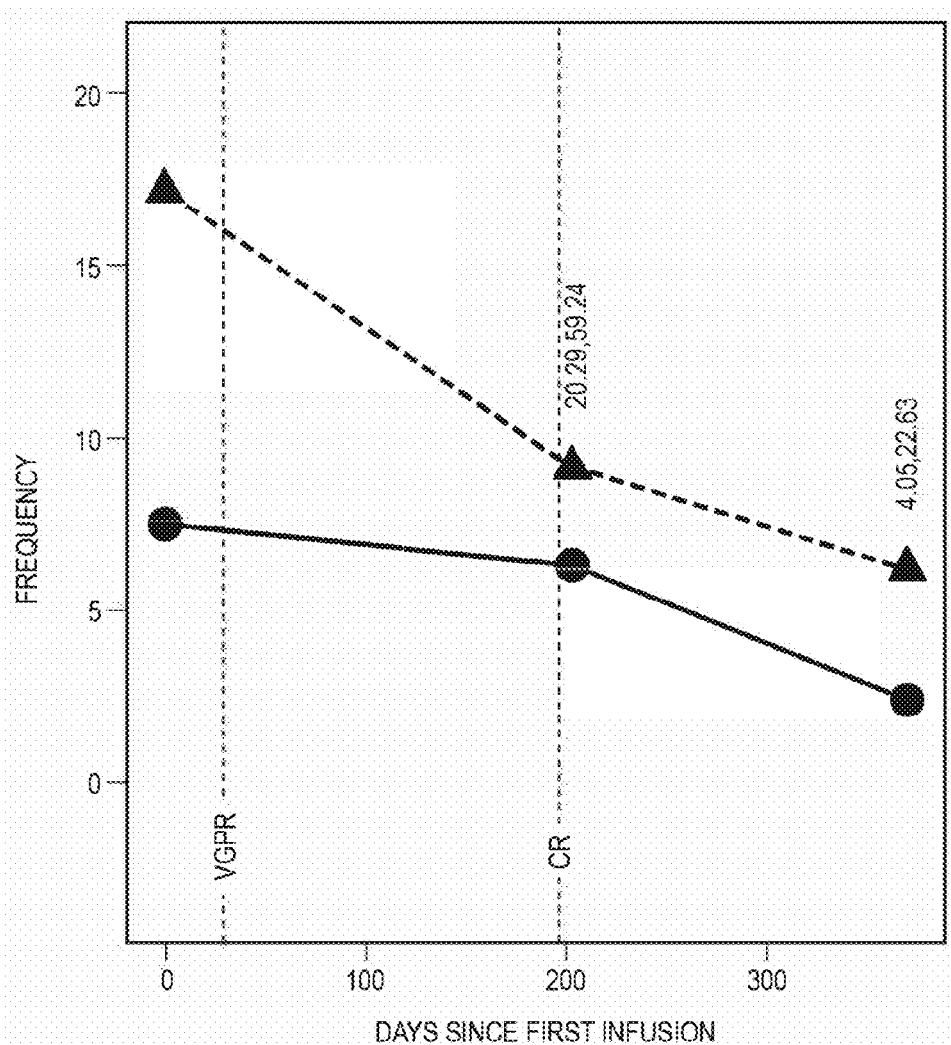
FIG. 10B illustrates a MRD profile of a subject who showed slow clinical response and remained MRD positive after suspected CR. Malignant clone frequency at baseline (x=0) and over time is shown. The vertical dotted lines show the clinical response call for that subject, with the label printed at the bottom. Two distinct tumor clones (solid lines and dashed lines) were identified in the patient. The subject was MRD positive at each evaluation point (threshold $10^{-5}$).
Figure 10C:
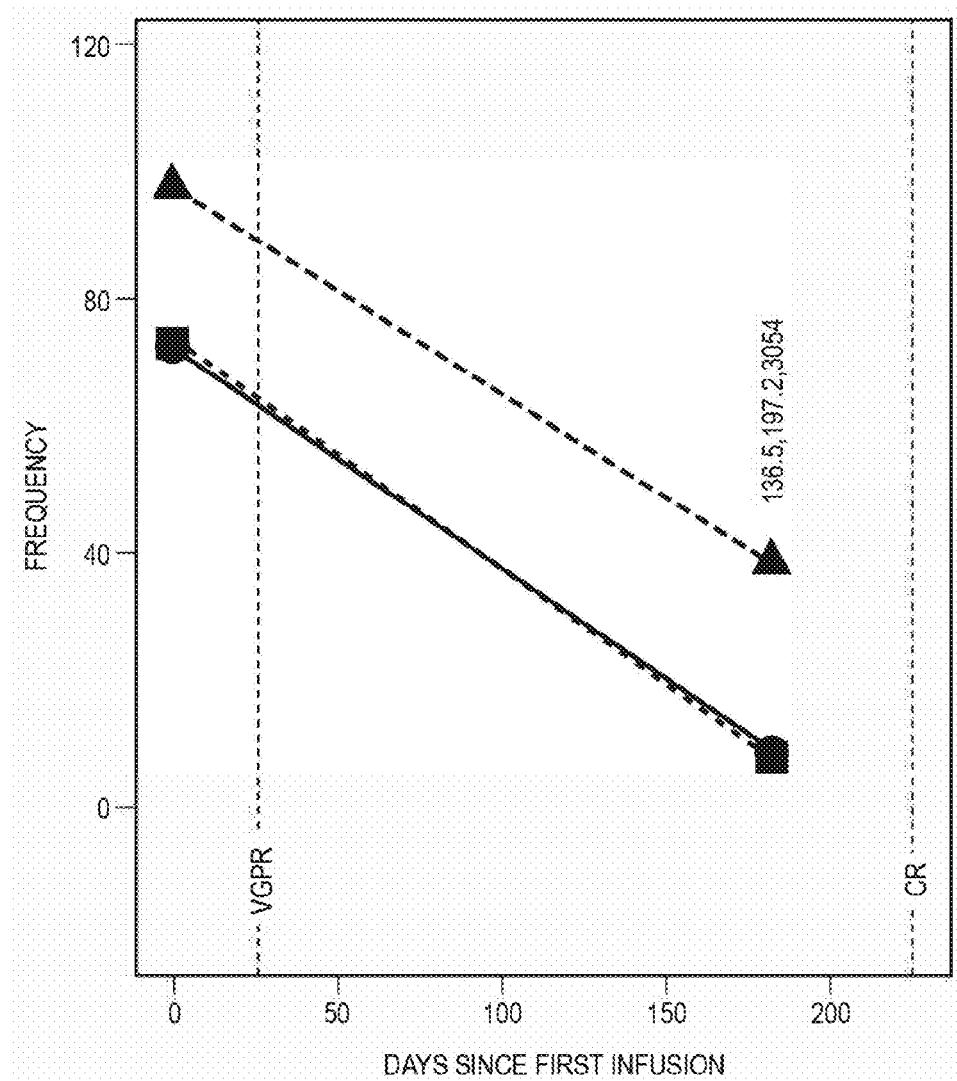
FIG. 10C illustrates a MRD profile of a subject who showed slow clinical response and remained MRD positive after suspected CR. Malignant clone frequency at baseline (x=0) and over time is shown. The vertical dotted lines show the clinical response call for that subject, with the label printed at the bottom. Two distinct tumor clones (solid lines and dashed lines) were identified in the patient. The subject was MRD positive at each evaluation point (threshold $10^{-5}$).
Figure 10D:
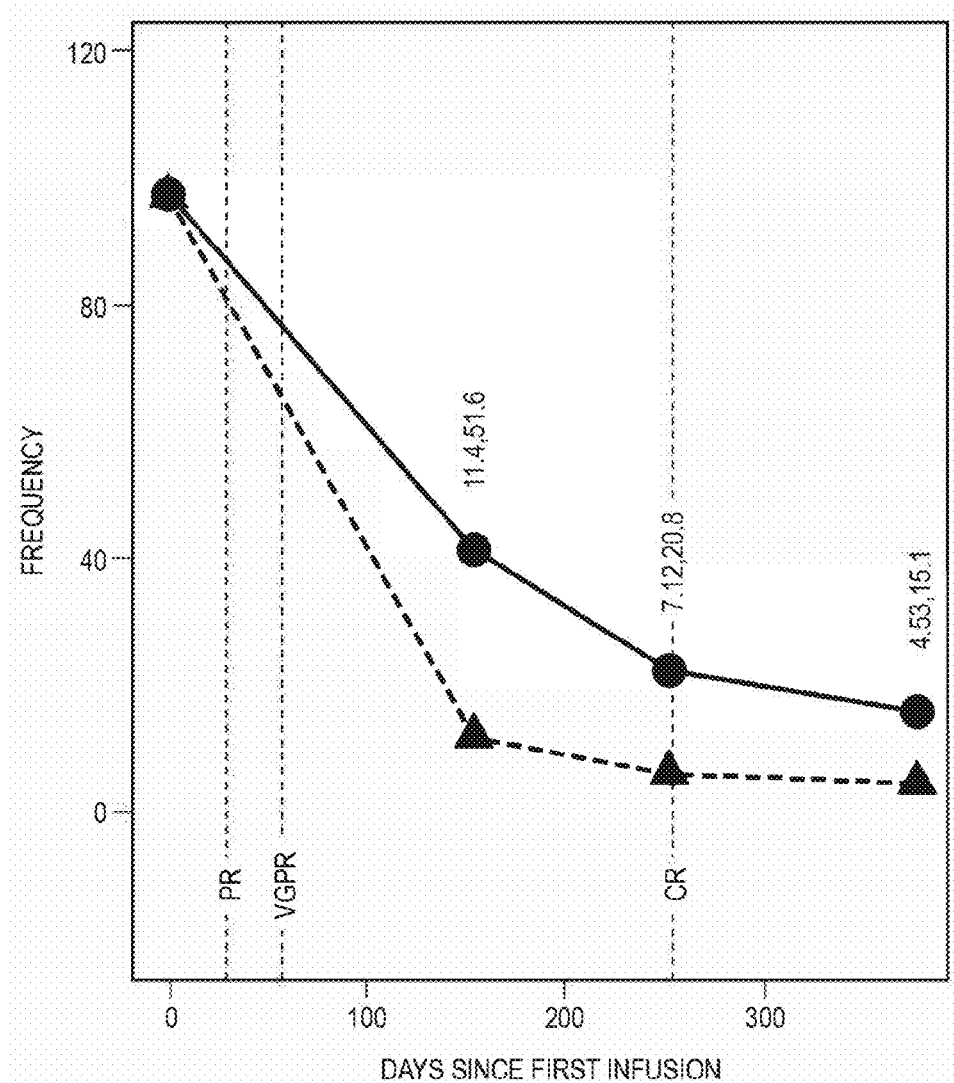
FIG. 10D illustrates a MRD profile of a subject who showed slow clinical response and remained MRD positive after suspected CR. Malignant clone frequency at baseline (x=0) and over time is shown. The vertical dotted lines show the clinical response call for that subject, with the label printed at the bottom. Two distinct tumor clones (solid lines and dashed lines) were identified in the patient. The subject was MRD positive at each evaluation point (threshold $10^{-5}$).

Some subjects showed rapid clinical response as well as a strong reduction in the clone frequency, but did not reach MRD negativity at first evaluation at the time of suspected CR. These subjects required more time to reach MRD negativity, but did eventually become MRD negative at later time points. FIG. 9A and FIG. 9B show the MRD profiles of two such subjects.

Slow Responders

A number of subjects were identified who reached clinical response status of CR or sCR in which the MRD individual clone receptors clearly decreased, interestingly some at different rates, but who remained MRD positive. FIG. 10A, FIG. 10B, FIG. 10C and FIG. 10D show the MRD profiles of four such subjects.

MRD Negativity in High-Risk and Standard Risk Subjects

The analysis sets included subgroup analyses of subjects from the POLLUX (Example 2) and CASTOR (Example 1) trials who were classified as high-risk or standard risk subjects based on cytogenetics status as described herein. MRD negativity was assessed separately at thresholds $10^{-4}$, $10^{-5}$ and $10^{-6}$.

Figure 11A:
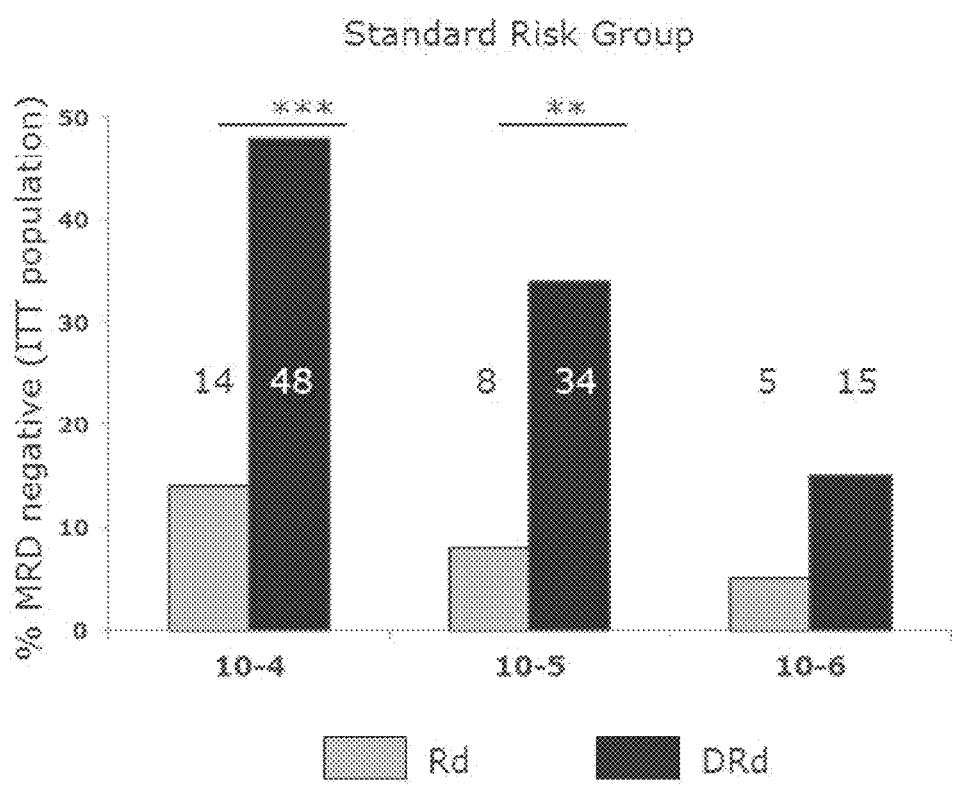
FIG. 11A illustrates the percentage (%) of MRD-negative subjects at indicated MRD negativity thresholds ($10^{-4}$, $10^{-5}$ or $10^{-6}$) in standard-risk patients from the POLLUX (MMY3003) trial. Light bars: patients that received lenalinomide and dexamethasone alone (Rd); Dark bars: patients that received daratumumab, lenalinomide, and dexamethasone (DRd). $p<0.005$; *$p<0.0001$ between indicated DRd vs Rd subject groups.
Figure 11B:
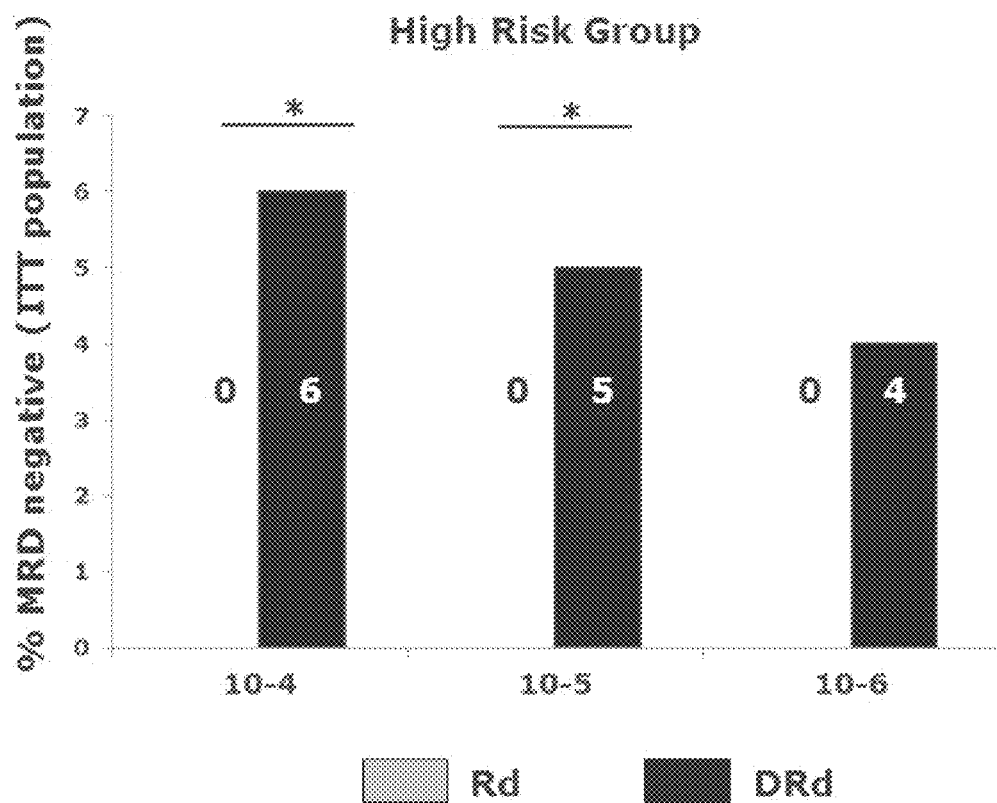
FIG. 11B illustrates the percentage (%) of MRD-negative subjects at indicated MRD negativity thresholds ($10^{-4}$, $10^{-5}$ or $10^{-6}$) in high-risk patients from the POLLUX (MMY3003) trial. Light bars: patients that received lenalinomide and dexamethasone alone (Rd); Dark bars: patients that received daratumumab, lenalinomide, and dexamethasone (DRd). *$p<0.05$ between indicated DRd vs Rd subject groups.

In POLLUX, significantly higher percentage of standard risk subjects achieved MRD negativity at $10^{-4}$ ($p<0.0001$; 48 pts vs 14 pts DRd vs Rd) and at $10^{-5}$ ($p<0.005$; 34 pts vs 8 pts DRd vs Rd) MRD threshold (FIG. 11A). No statistical significance was reached at $10^{-6}$ MRD threshold in standard risk subjects (15 pts vs 5 pts DRd vs Rd). Significantly higher percentage of high risk subjects achieved MRD negativity at $10^{-4}$ ($p<0.05$; 6 pts vs 0 pts DRd vs Rd) and at $10^{-5}$ ($p<0.05$; 5 pts vs 0 pts DRd vs Rd) MRD threshold (FIG. 11B). No statistical significance was reached at $10^{-4}$ MRD threshold in standard risk subjects (4 pts vs 0 pts DRd vs Rd).

Figure 12A:
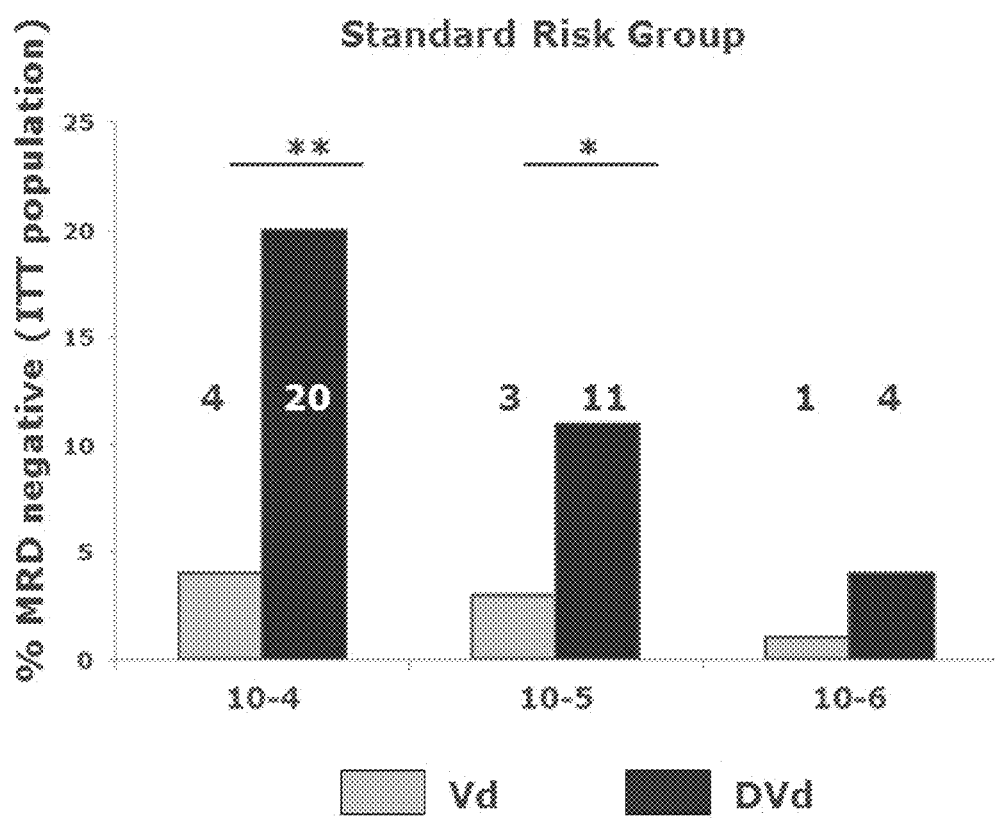
FIG. 12A illustrates the percentage (%) of MRD-negative subjects at indicated MRD negativity thresholds ($10^{-4}$, $10^{-5}$ or $10^{-6}$) in standard-risk patients from the CASTOR (MMY3004) trial. Light bars: patients that received bortezomib and dexamethasone (Vd); Dark bars: patients that received daratumumab, bortezomib, and dexamethasone (DVd). *$p<0.05$; **$p<0.005$ between indicated DVd vs Vd subject groups.
Figure 12B:
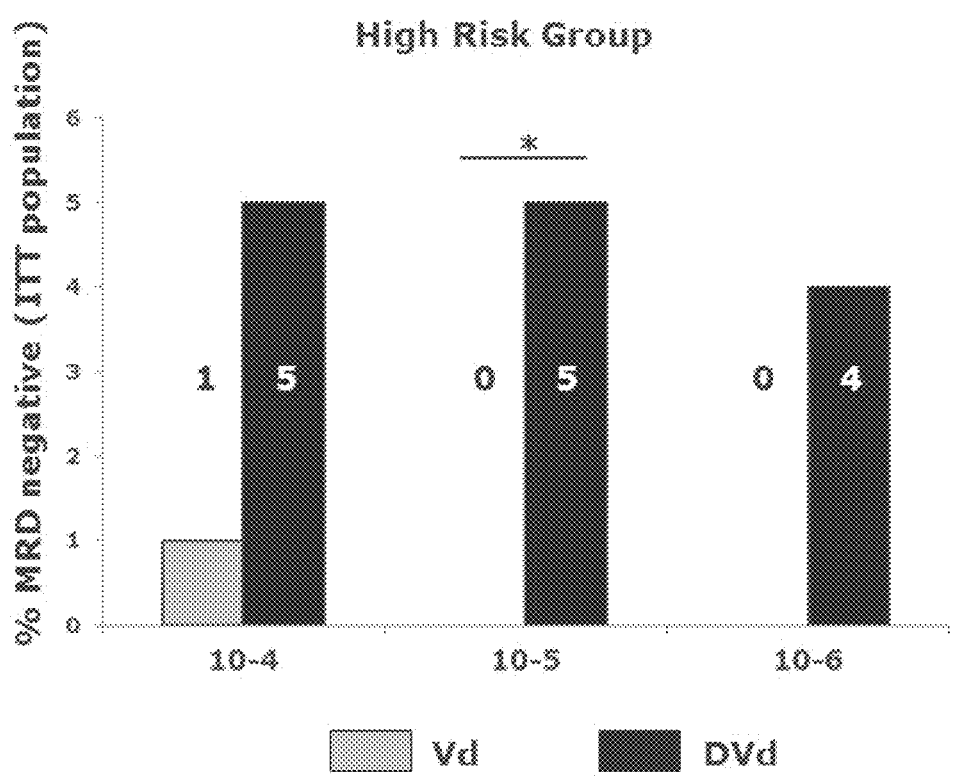
FIG. 12B illustrates the percentage (%) of MRD-negative subjects at indicated MRD negativity thresholds ($10^{-4}$, $10^{-5}$ or $10^{-6}$) in high-risk patients from the CASTOR (MMY3004) trial. Light bars: patients that received bortezomib and dexamethasone (Vd); Dark bars: patients that received daratumumab, bortezomib, and dexamethasone (DVd). *$p<0.05$ in DVd vs Vd subject groups.

In CASTOR, significantly higher percentage of standard risk subjects achieved MRD negativity at $10^{-4}$ ($p<0.005$; 20 pts vs 4 pts DVd vs Vd) and at $10^{-5}$ ($p<0.05$; 11 pts vs 3 pts DVd vs Vd) MRD thresholds (FIG. 12A). No statistical significance was reached at $10^{-6}$ MRD threshold in standard risk subjects (4 pts vs 1 pts DVd vs Vd). Significantly higher percentage of high risk subjects achieved MRD negativity at $10^{-5}$ ($p<0.05$; 5 pts vs 0 pts DVd vs Vd) MRD threshold (FIG. 12B). No statistical significance was reached at $10^{-4}$ (5 pts vs 1 pts DVd vs Vd) or at $10^{-6}$ (4 pts vs 0 pts DVd vs Vd) MRD thresholds in high risk subjects (4 pts vs 0 pts DRd vs Rd).

MRD Case Type: Conclusions

These plots highlight the potential utility of longitudinal MRD analysis to further categorize response and escape phenotypes. In addition, patients may be identified as to who will progress on therapy and may allow for earlier treatment interventions of next lines of therapy.

Conclusion

Minimal residual disease negativity rate was significantly higher in the daratumumab containing regimens compared to the control groups (DRd: 29% vs Rd: 7.8% in Study POLLUX and DVd: 14% vs Vd: 3.0% in Study CASTOR) at the predefined hierarchical threshold of $10^{-4}$ and at least a 3-fold greater MRD negativity rate regardless of background therapies or threshold. Additional evaluation at the more stringent threshold of $10^{-5}$ demonstrated that daratumumab containing regimens also reached significantly higher MRD negativity rates as compared to the control groups. Further, these MRD data highlight the ability of daratumumab containing regimens in driving deep responses in this challenging patient population. Also at $10^{-6}$, DVd induced increased MRD negative rates compared to Vd, although statistical significance was not reached.

In summary, these two studies represent the first randomized, controlled, prospective evaluation of MRD in the relapsed or refractory MM Phase 3 clinical study setting and demonstrated that daratumumab-containing therapies are able to remarkably induce deep levels of clinical response in MM subjects. Regardless of the background therapies, daratumumab-containing regimens consistently showed 3-fold or greater increases in MRD negativity rate compared with the control groups at all evaluated thresholds. Importantly, since subjects who achieved MRD negative status demonstrated low PFS event rates, the deep clinical responses induced by addition of daratumumab may lead to improved long-term outcomes.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

The disclosures of each patent, patent application, and publication cited or described in this document are hereby incorporated herein by reference, in its entirety.

TABLE 9

Sequences

| SEQ ID NO: | Sequence |
| --- | --- |
| Human CD38 aa SEQ ID NO: 1 | MANCEFSPVSGDKPCCRLSRRAQLCLGVSILVLILVVVLAVVVP RWRQQWSGPGTTKRFPETVLARCVKYTEIHPEMRHVDCQSVW DAFKGAFISKHPCNITEEDYQPLMKLGTQTVPCNKILLWSRIKD LAHQFTQVQRDMFTLEDTLLGYLADDLTWCGEFNTSKINYQSC PDWRKDCSNNPVSVFWKTVSRRFAEAACDVVHVMLNGSRSKI FDKNSTFGSVEVHNLQPEKVQTLEAWVIHGGREDSRDLCQDPTI KELESIISKRNIQFSCKNIYRPDKFLQCVKNPEDSSCTSEI |
| Human CD38 region 1 aa SEQ ID NO: 2 | SKRNIQFSCKNIYR |
| Human CD38 region 2 aa SEQ ID NO: 3 | EKVQTLEAWVIHGG |

TABLE 9-continued

Sequences

| SEQ ID NO: | Sequence |
|---|---|
| Daratumumab VH SEQ ID NO: 4 | EVQLLESGGGLVQPGGSLRLSCAVSGFTFNSFAMSWVRQAPGK GLEWVSAISGSGGGTYYADSVKGRFTISRDNSKNTLYLQMNSL RAEDTAVYFCAKDKILWFGEPVFDYWGQGTLVTVSS |
| Daratumumab VL SEQ ID NO: 5 | EIVLTQSPATLSLSPGERATLSCRASQSVSSYLAWYQQKPGQAP RLLIYDASNRATGIPARFSGSGSGTDFTLTISSLEPEDFAVYYCQ QRSNWPPTFGQGTKVEIK |
| Daratumumab HCDR1 SEQ ID NO: 6 | SFAMS |
| Daratumumab HCDR2 SEQ ID NO: 7 | AISGSGGGTYYADSVKG |
| Daratumumab HCDR3 SEQ ID NO: 8 | DKILWFGEPVFDY |
| Daratumumab LCDR1 SEQ ID NO: 9 | RASQSVSSYLA |
| Daratumumab LCDR2 SEQ ID NO: 10 | DASNRAT |
| Daratumumab LCDR3 SEQ ID NO: 11 | QQRSNWPPTF |
| Daratumumab HC SEQ ID NO: 12 | EVQLLESGGGLVQPGGSLRLSCAVSGFTFNSFAMSWVRQAPGK GLEWVSAISGSGGGTYYADSVKGRFTISRDNSKNTLYLQMNSL RAEDTAVYFCAKDKILWFGEPVFDYWGQGTLVTVSSASTKGPS VFPLAPSSKSTSGGTAALGCLVKDYFPEPVTVSWNSGALTSGVH TFPAVLQSSGLYSLSSVVTVPSSSLGTQTYICNVNHKPSNTKVD KRVEPKSCDKTHTCPPCPAPELLGGPSVFLFPPKPKDTLMISRTP EVTCVVVDVSHEDPEVKFNWYVDGVEVHNAKTKPREEQYNST YRVVSVLTVLHQDWLNGKEYKCKVSNKALPAPIEKTISKAKGQ PREPQVYTLPPSREEMTKNQVSLTCLVKGFYPSDIAVEWESNGQ PENNYKTTPPVLDSDGSFFLYSKLTVDKSRWQQGNVFSCSVMH EALHNHYTQKSLSLSPGK |
| Daratumumab LC SEQ ID NO: 13 | EIVLTQSPATLSLSPGERATLSCRASQSVSSYLAWYQQKPGQAP RLLIYDASNRATGIPARFSGSGSGTDFTLTISSLEPEDFAVYYCQ QRSNWPPTFGQGTKVEIKRTVAAPSVFIFPPSDEQLKSGTASVVC LLNNFYPREAKVQWKVDNALQSGNSQESVTEQDSKDSTYSLSS TLTLSKADYEKHKVYACEVTHQGLSSPVTKSFNRGEC |
| mAb003 VH SEQ ID NO: 14 | QVQLVQSGAEVKKPGSSVKVSCKASGGTFSSYAFSWVRQAPGQ GLEWMGRVIPFLGIANSAQKFQGRVTITADKSTSTAYMDLSSLR SEDTAVYYCARDDIAALGPFDYWGQGTLVTVSSAS |
| mAb003 VL SEQ ID NO: 15 | DIQMTQSPSSLSASVGDRVTITCRASQGISSWLAWYQQKPEKAP KSLIYAASSLQSGVPSRFSGSGSGTDFTLTISSLQPEDFATYYCQQ YNSYPRTFGQGTKVEIK |
| mAb024 VH SEQ ID NO: 16 | EVQLVQSGAEVKKPGESLKISCKGSGYSFSNYWIGWVRQMPGK GLEWMGITYPHDSDARYSPSFQGQVTFSADKSISTAYLQWSSLK ASDTAMYYCARHVGWGSRYWYFDLWGRGTLVTVSS |
| mAb024 VL SEQ ID NO: 17 | EIVLTQSPATLSLSPGERATLSCRASQSVSSYLAWYQQKPGQAP GLLIYDASNRASGIPARFSGSGSGTDFTLTISSLEPEDFAVYYCQ QRSNWPLTFGGGTKVEIK |
| MOR-202 VH SEQ ID NO: 18 | QVQLVESGGGLVQPGGSLRLSCAASGFTFSSYYMNWVRQAPG KGLEWVSGISGDPSNTYYADSVKGRFTISRDNSKNTLYLQMNS LRAEDTAVYYCARDLPLVYTGFAYWGQGTLVTVSS |

TABLE 9-continued

| SEQ ID NO: | Sequence |
|---|---|
| MOR-202 VL SEQ ID NO: 19 | DIELTQPPSVSVAPGQTARISCSGDNLRHYYVYWYQQKPGQAPVLVIYGDSKRPSGIPERFSGSNSGNTATLTISGTQAEDEADYYCQTYTGGASLVFGGGTKLTVLGQ |
| Isatuximab VH SEQ ID NO: 20 | QVQLVQSGAEVAKPGTSVKLSCKASGYTFTDYWMQWVKQRPGQGLEWIGTIYPGDGDTGYAQKFQGKATLTADKSSKTVYMHLSSLASEDSAVYYCARGDYYGSNSLDYWGQGTSVTVSS |
| Isatuximab VL SEQ ID NO: 21 | DIVMTQSHLSMSTSLGDPVSITCKASQDVSTVVAWYQQKPGQSPRRLIYSASYRYIGVPDRFTGSGAGTDFTFTISSVQAEDLAVYYCQQHYSPPYTFGGGTKLEIK |

What is claimed is:

1. A method of achieving negative minimal residual disease status in a subject having high-risk multiple myeloma, comprising administering to the subject an anti-CD38 antibody, dexamethasone, and bortezomib, wherein:
   the anti-CD38 antibody comprises a heavy chain complementarity determining region (HCDR) 1, a HCDR2, a HCDR3, a light chain complementarity determining region (LCDR) 1, a LCDR2 and a LCDR3 amino acid sequences of SEQ ID NOs: 6, 7, 8, 9, 10 and 11, respectively; wherein:
   the anti-CD38 antibody is administered as an intravenous infusion at a dose of about 16 mg/kg once per week in a 21-day cycle on days 1, 8, and 15 for cycles 1-3, once every 3 weeks in a 21-day cycle on day 1 for cycles 4-8, and once every 4 weeks thereafter; and
   bortezomib is administered at a dose of about 1.3 mg/m$^2$ subcutaneously (SC) in a 21-day cycle on days 1, 4, 8, and 11 for cycles 1-8; and
   dexamethasone is administered at 20 mg IV or PO in a 21-day cycle on days 1, 2, 4, 5, 8, 9, 11, and 12 for a total dose of 160 mg per cycle for cycles 1-8, wherein:
   the subject has one or more chromosomal abnormalities comprising:
   a) t(4;14)(p16;q32);
   b) t(14;16)(q32;q23);
   c) t(4;14)(p16;q32) and t(14;16)(q32;q23);
   d) t(4;14)(p16;q32) and del17p;
   e) t(14;16)(q32;q23) and del17p; or
   f) t(4;14)(p16;q32), t(14;16)(q32;q23) and del17p; and
   wherein the method increases progression-free survival events compared to administering dexamethasone and bortezomib without the anti-CD38 antibody.

2. The method of claim 1, wherein the subject has relapsed or refractory multiple myeloma.

3. The method of claim 1, wherein the anti-CD38 antibody comprises a heavy chain variable region comprising the amino acid sequence of SEQ ID NO: 4 and a light chain variable region comprising the amino acid sequence of SEQ ID NO: 5.

4. The method of claim 1, wherein the anti-CD38 antibody comprises a heavy chain comprising the amino acid sequence of SEQ ID NO: 12 and a light chain comprising the amino acid sequence of SEQ ID NO: 13.

5. The method of claim 1, wherein the negative minimal residual disease is detected by evaluating an amount of myeloma cells in a bone marrow aspirate sample from the subject.

6. A method of decreasing a risk of relapse and/or disease progression in a subject having high-risk multiple myeloma, comprising administering to the subject an anti-CD38 antibody, dexamethasone, and bortezomib, wherein:
   the anti-CD38 antibody comprises a heavy chain complementarity determining region (HCDR) 1, a HCDR2, a HCDR3, a light chain complementarity determining region (LCDR) 1, a LCDR2 and a LCDR3 amino acid sequences of SEQ ID NOs: 6, 7, 8, 9, 10 and 11, respectively; wherein:
   the anti-CD38 antibody is administered as an intravenous infusion at a dose of about 16 mg/kg once per week in a 21-day cycle on days 1, 8, and 15 for cycles 1-3, once every 3 weeks in a 21-day cycle on day 1 for cycles 4-8, and once every 4 weeks thereafter; and
   bortezomib is administered at a dose of about 1.3 mg/m$^2$ subcutaneously (SC) in a 21-day cycle on days 1, 4, 8, and 11 for cycles 1-8; and dexamethasone is administered at 20 mg IV or PO in a 21-day cycle on days 1, 2, 4, 5, 8, 9, 11, and 12 for a total dose of 160 mg per cycle for cycles 1-8, wherein:

the subject has one or more chromosomal abnormalities comprising:
a) t(4;14)(p16;q32);
b) t(14;16)(q32;q23);
c) t(4;14)(p16;q32) and t(14;16)(q32;q23);
d) t(4;14)(p16;q32) and del17p;
e) t(14;16)(q32;q23) and del17p; or
f) t(4;14)(p16;q32), t(14;16)(q32;q23) and del17p; and wherein the method increases progression-free survival events compared to administering dexamethasone and bortezomib without the anti-CD38 antibody.

7. A method of treating a subject having high-risk multiple myeloma, comprising administering to the subject an anti-CD38 antibody, dexamethasone, and bortezomib, wherein:

the anti-CD38 antibody comprises a heavy chain complementarity determining region (HCDR) 1, a HCDR2, a HCDR3, a light chain complementarity determining region (LCDR) 1, a LCDR2 and a LCDR3 amino acid sequences of SEQ ID NOs: 6, 7, 8, 9, 10 and 11, respectively; wherein:

the anti-CD38 antibody is administered as an intravenous infusion at a dose of about 16 mg/kg once per week in a 21-day cycle on days 1, 8, and 15 for cycles 1-3, once every 3 weeks in a 21-day cycle on day 1 for cycles 4-8, and once every 4 weeks thereafter; and bortezomib is administered at a dose of about 1.3 mg/m$^2$ subcutaneously (SC) in a 21-day cycle on days 1, 4, 8, and 11 for cycles 1-8; and dexamethasone is administered at 20 mg IV or PO in a 21-day cycle on days 1, 2, 4, 5, 8, 9, 11, and 12 for a total dose of 160 mg per cycle for cycles 1-8, wherein:

the subject has one or more chromosomal abnormalities comprising:
a) t(4;14)(p16;q32);
b) t(14;16)(q32;q23);
c) t(4;14)(p16;q32) and t(14;16)(q32;q23);
d) t(4;14)(p16;q32) and del17p;
e) t(14;16)(q32;q23) and del17p; or
f) t(4;14)(p16;q32), t(14;16)(q32;q23) and del17p; and wherein the method increases progression-free survival events compared to administering dexamethasone and bortezomib without the anti-CD38 antibody.

8. The method of claim 7, wherein the anti-CD38 antibody comprises a heavy chain variable region comprising the amino acid sequence of SEQ ID NO: 4 and a light chain variable region comprising the amino acid sequence of SEQ ID NO: 5.

9. The method of claim 7, wherein the anti-CD38 antibody comprises a heavy chain comprising the amino acid sequence of SEQ ID NO: 12 and a light chain comprising the amino acid sequence of SEQ ID NO: 13.

10. The method of claim 7, wherein the subject has high risk refractory or relapsed multiple myeloma.

11. The method of claim 7, wherein the method further improves one or more outcome measurements of the subject compared to a subject receiving dexamethasone and bortezomib.

12. The method of claim 7, wherein the method achieves minimal residual disease-negativity in the subject.

* * * * *